United States Patent
Wu et al.

(10) Patent No.: US 11,180,497 B2
(45) Date of Patent: Nov. 23, 2021

(54) CYCLIC COMPOUNDS AS IMMUNOMODULATING AGENTS

(71) Applicant: ANGEX PHARMACEUTICAL, INC., North Brunswick, NJ (US)

(72) Inventors: Wen-Lian Wu, Green Brook, NJ (US); Zhiqiang Yang, Westfield, NJ (US); Francis Lee, Yardley, PA (US); John Qiang Tan, North Brunswick, NJ (US)

(73) Assignee: ANGEX PHARMACEUTICAL, INC., North Brunswick, NJ (US)

( * ) Notice: Subject to any disclaimer, the term of this patent is extended or adjusted under 35 U.S.C. 154(b) by 0 days.

(21) Appl. No.: 16/648,213

(22) PCT Filed: Sep. 5, 2018

(86) PCT No.: PCT/US2018/049528
§ 371 (c)(1),
(2) Date: Mar. 17, 2020

(87) PCT Pub. No.: WO2019/078968
PCT Pub. Date: Apr. 25, 2019

(65) Prior Publication Data
US 2020/0239464 A1 Jul. 30, 2020

Related U.S. Application Data

(60) Provisional application No. 62/624,296, filed on Jan. 31, 2018, provisional application No. 62/574,054, filed on Oct. 18, 2017.

(51) Int. Cl.
| | | |
|---|---|---|
| C07D 471/04 | (2006.01) |
| C07D 215/14 | (2006.01) |
| C07D 401/04 | (2006.01) |
| C07D 401/08 | (2006.01) |
| C07D 401/12 | (2006.01) |

(52) U.S. Cl.
CPC ......... *C07D 471/04* (2013.01); *C07D 215/14* (2013.01); *C07D 401/04* (2013.01); *C07D 401/08* (2013.01); *C07D 401/12* (2013.01)

(58) Field of Classification Search
CPC .. C07D 471/04; C07D 401/04; C07D 401/08; C07D 401/12; C07D 215/14
See application file for complete search history.

(56) References Cited

U.S. PATENT DOCUMENTS

| | | | | |
|---|---|---|---|---|
| 2020/0239420 A1* | 7/2020 | Kazmierski | ............. | A61P 31/18 |
| 2020/0276180 A1* | 9/2020 | Zhang | .................. | C07D 403/02 |
| 2020/0331887 A1* | 10/2020 | Li | ......................... | C07D 409/12 |
| 2021/0047290 A1* | 2/2021 | Wang | .................. | C07D 215/14 |

FOREIGN PATENT DOCUMENTS

| | | |
|---|---|---|
| WO | 2016073738 A2 | 5/2016 |
| WO | 2016073770 A1 | 5/2016 |
| WO | 2016073774 A2 | 5/2016 |
| WO | 2018039512 A1 | 3/2018 |
| WO | 2018039518 A1 | 3/2018 |

OTHER PUBLICATIONS

Opitz, PLOS One, May 2011, vol. 6(1), e19823, pp. 1-11. (Year: 2011).*

* cited by examiner

*Primary Examiner* — D Margaret M Seaman
(74) *Attorney, Agent, or Firm* — Maschoff Brennan; Brent A. Johnson; Yuefen Zhou

(57) ABSTRACT

The present disclosure describes novel IDO inhibitors and methods for preparing them. The pharmaceutical compositions comprising such IDO inhibitors and methods of using them for treating cancer, infectious diseases, and other disorders are also described.

25 Claims, No Drawings

U.S. 11,180,497 B2

CYCLIC COMPOUNDS AS IMMUNOMODULATING AGENTS

CROSS-REFERENCE TO RELATED APPLICATIONS

This application is a national phase of PCT/US2018/049528, filed Sep. 5, 2018; which claims the benefit of U.S. Provisional Application Nos. 62/574,054, filed Oct. 18, 2017, and 62/624,296, filed Jan. 31, 2018; all of which are incorporated by reference by their entirety.

FIELD

The present disclosure relates to cyclic compounds, including spirocyclic compounds, such as spiro[2.5]octane and 6-azaspiro[2.5]octane analogs, and cycloalkyl substituted amide compounds, such as (1$\lambda^3$-cyclopropyl)-4$\lambda^3$-cyclohexane and 4-(1$\lambda^3$-cyclopropyl)-1$\lambda^3$-piperidine analogs, as IDO inhibitors, and pharmaceutical compositions containing such compounds. The present disclosure also relates to the use of the compounds and pharmaceutical compositions to treat cancer, infectious diseases and other disorders.

BACKGROUND

The initial and rate-limiting step of kynurenine pathway is known to be the conversion of the essential amino acid L-tryptophan into N-formylkynurenine by indoleamine 2,3-dioxygenase (IDO). Overexpression of IDO has been found in several types of tumors. The catabolism of L-tryptophan mediated by IDO is thought to be an important immune effector pathway for the tumor cells to escape immune response. In addition, IDO has been associated with diseases other than cancer including infectious diseases, inflammatory diseases, autoimmune diseases and CNS disorders. Accordingly, the identification and development of small-molecules that specifically inhibit IDO activity can potentially provide a new therapeutic approach for successful treatment of a variety of IDO-related diseases or disorders, such as cancers.

SUMMARY

This disclosure relates to certain optionally substituted spiro[2.5]octanyl compounds, optionally substituted 6-azaspiro[2.5]octanyl compounds, optionally substituted spiro[3.5]nonanyl compounds, optionally substituted 7-azaspiro[3.5]nonanyl compounds, optionally substituted spiro[4.5]decanyl compounds, optionally substituted 8-azaspiro[4.5]decanyl compounds, optionally substituted (1$\lambda^3$-cyclopropyl)-4$\lambda^3$-cyclohexanes, or optionally substituted 4-(1$\lambda^3$-cyclopropyl)-1$\lambda^3$-piperidines. For example, some embodiments include a compound, or a pharmaceutically acceptable salt thereof, wherein the compound is: optionally substituted N-phenyl-6-(quinolin-4-yl)spiro[2.5]octane-1-carboxamide, optionally substituted N-(6-(quinolin-4-yl)spiro[2.5]octan-1-yl)benzamide, optionally substituted N-phenyl-6-(quinolin-4-yl)-6-azaspiro[2.5]octane-1-carboxamide, optionally substituted N-(6-(quinolin-4-yl)-6-azaspiro[2.5]octan-1-yl)benzamide, optionally substituted N-(1-(4-(quinolin-4-yl)cyclohexyl)cyclopropyl)benzamide, optionally substituted N-phenyl-1-(4-(quinolin-4-yl)cyclohexyl)cyclopropane-1-carboxamide, or any optionally substituted compound represented in Table A and Table B below.

Some embodiments include a compound represented by Formula 1:

 (Formula 1)

or a pharmaceutically acceptable salt thereof; wherein A is an optionally substituted $C_{4-10}$ cyclic moiety which attaches at a ring atom; D is optionally substituted spiro[2.5]octanyl or optionally substituted 6-azaspiro[2.5]octanyl, which attaches at the 1 and 6 positions; spiro[3.5]nonanyl or 7-azaspiro[3.5]nonanyl, which attaches at the 1 and 7 or 2 and 7 positions; or spiro[4.5]decanyl or 8-azaspiro[4.5]decanyl, which attaches at the 1 and 8 positions; E is optionally substituted $C_{6-10}$ aryl or optionally substituted $C_{3-9}$ heteroaryl; and L is $L^1$-$L^2$-$L^3$, wherein $L^1$, $L^2$, and $L^3$ are independently a covalent bond, $C(R^A)(R^B)$, $C(R^A)(CF_3)$, O, $NR^A$, C(O), or $S(O)_2$, wherein $R^A$ and $R^B$ are independently H or $C_{1-12}$ hydrocarbyl, and a C atom or an N atom of L directly attaches to D at position 1, or at position 1 or 2 when D is spiro[3.5]nonanyl or 7-azaspiro[3.5]nonanyl. In some embodiments, L is not a covalent bond. In some embodiments, L is not O. In some embodiments, L is not C(O). In some embodiments, L is not $S(O)_2$.

Some embodiments include a compound represented by Formula 2:

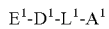 (Formula 2)

or a pharmaceutically acceptable salt thereof; wherein $A^1$ is an optionally substituted $C_{4-10}$ cyclic moiety which attaches at a ring atom; $D^1$ is optionally substituted (1$\lambda^3$-cyclopropyl)-4$\lambda^3$-cyclohexane, or 4-(1$\lambda^3$-cyclopropyl)-1$\lambda^3$-piperidine; $E^1$ is optionally substituted $C_{6-10}$ aryl or optionally substituted $C_{3-9}$ heteroaryl; and $L^1$ is —C(O)—NH— or —NH—C(O)—, wherein $L^1$ is directly attached to the cyclopropyl ring of $D^1$.

Some embodiments include a method of treating cancer, infectious diseases and other IDO associated disorders comprising administering a compound described herein, such as a compound of Formula 1 or 2, optionally substituted N-phenyl-6-(quinolin-4-yl)spiro[2.5]octane-1-carboxamide, optionally substituted N-(6-(quinolin-4-yl)spiro[2.5]octan-1-yl)benzamide, optionally substituted N-phenyl-6-(quinolin-4-yl)-6-azaspiro[2.5]octane-1-carboxamide, or optionally substituted N-(6-(quinolin-4-yl)-6-azaspiro[2.5]octan-1-yl)benzamide, optionally substituted N-(1-(4-(quinolin-4-yl)cyclohexyl)cyclopropyl)benzamide, optionally substituted N-phenyl-1-(4-(quinolin-4-yl)cyclohexyl)cyclopropane-1-carboxamide, or any optionally substituted compound represented in Table A or Table B below, or a pharmaceutically acceptable salt thereof (referred to collectively herein as a "subject compound"), to a patient in need thereof.

Some embodiments include use of a compound described herein, such as a compound of Formula 1 or 2, a subject compound described herein in the manufacture of a medicament for the treatment of cancer, infectious diseases and other IDO associated disorders.

Some embodiments include a pharmaceutical composition comprising a therapeutically effective amount of a subject compound described herein in combination with at least one pharmaceutically acceptable carrier.

Some embodiments include a process for making a pharmaceutical composition comprising combining a subject compound described herein and at least one pharmaceutically acceptable carrier.

DETAILED DESCRIPTION

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described herein.

If stereochemistry is not indicated, a name or structural depiction includes any stereoisomer or any mixture of stereoisomers.

In some embodiments, a compound of Formula 1 is an R-enantiomer. In some embodiments, a compound of Formula 1 is an S-enantiomer.

In some embodiments, a compound of Formula 2 is a cis-isomer. In some embodiments, a compound of Formula 2 is a trans-isomer.

Unless otherwise indicated, when a compound or chemical structural feature such as aryl is referred to as being "optionally substituted," it includes a feature that has no substituents (i.e. unsubstituted), or a feature that is "substituted," meaning that the feature has one or more substituents. The term "substituent" is broad, and includes a moiety that occupies a position normally occupied by one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, P, Si, F, Cl, Br, or I; provided that the substituent includes at least one C, N, O, S, P, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, N-oxide, silyl, sulfenyl, sulfinyl, sulfonyl, sulfoxide, haloalkyl, haloalkoxyl, trihalomethanesulfonyl, trihalomethanesulfonamido, amino, phosphonic acid, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or substituted with a substituent that may independently be in any position normally occupied by a hydrogen atom when the structure is unsubstituted. Unless a point of attachment is indicated by ─│, attachment may occur at any position normally occupied by a hydrogen atom.

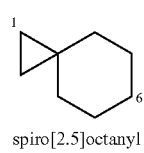
spiro[2.5]octanyl

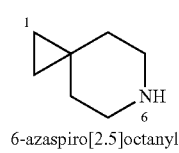
6-azaspiro[2.5]octanyl

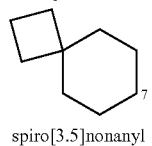
spiro[3.5]nonanyl

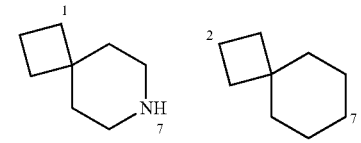
7-azaspiro[3.5]nonanyl     spiro[3.5]nonane

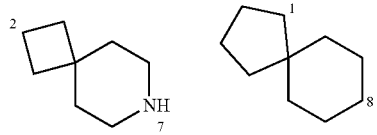
7-azaspiro[3.5]nonane     spiro[4.5]decanyl

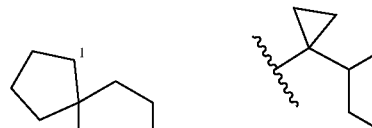
8-azaspiro[4.5]decanyl     (1λ³-cyclopropyl)-4λ³-cyclohexane

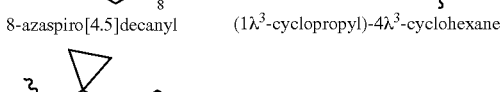
4-(1λ³-cyclopropyl)-1λ²-piperidine

With respect to Formula 1, A is an optionally substituted $C_{4-10}$ cyclic moiety, such as a cyclic hydrocarbyl or a cyclic heterocycle (e.g. cycloalkyl, cycloalkenyl, cycloalkynyl, aryl, heteroaryl, etc.) which attaches at a ring atom. Potential substituents of A may include halo, such as F, Cl, Br, I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; $C_6N_{0-1}O_{0-3}F_{0-13}H_{0-14}$; $C_{1-9}$ heterocycles; etc. In some embodiments, A is optionally substituted phenyl having 0, 1, 2, 3, 4, or 5 substituents, such as phenyl substituted with F, Cl, Br, $C_{1-6}$ alkyl, —$CO_2H$, —CN, —CO—$C_{1-6}$-alkyl, —C(O)O—$C_{1-6}$-alkyl, $C_{1-6}$ alkyl-OH, OH, $NH_2$, etc. In some embodiments, A is unsubstituted phenyl. In some embodiments, A is phenyl having 2 substituents. In some embodiments, A is phenyl having 1 substituent.

With respect to Formula 1, in some embodiments, A is represented by Formula A1, A2, A3, A4, or A5:

Formula A1

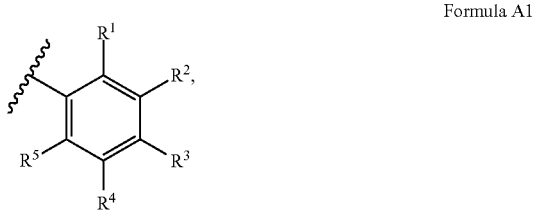

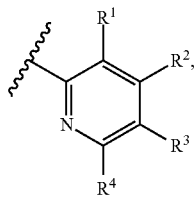

Formula A2

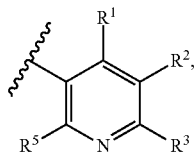

Formula A3

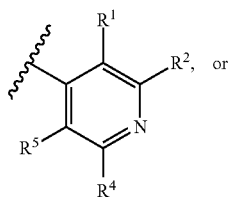

Formula A4

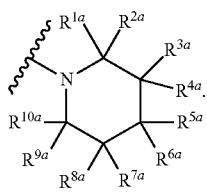

Formula A5

With respect to Formula A1, A2, A3, or A4, $R^1$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. Some of the structures of the substituents with attachment points are shown below. In some embodiments, $R^1$ may be H; F; Cl; CN; $CF_3$; OH; $NH_2$; $C_{1-6}$ alkyl, such as methyl, ethyl, a propyl isomer (e.g. n-propyl or isopropyl), cyclopropyl, a butyl isomer, a cyclobutyl isomer (e.g. cyclobutyl or methylcyclopropyl), a pentyl isomer, a cyclopentyl isomer, a hexyl isomer, a cyclohexyl isomer, etc.; or $C_{1-6}$ alkoxy, such as —O-methyl, —O-ethyl, an isomer of —O-propyl, —O-cyclopropyl, an isomer of —O-butyl, an isomer of —O-cyclobutyl, an isomer of —O-pentyl, an isomer of —O-cyclopentyl, an isomer of —O-hexyl, an isomer of —O-cyclohexyl, etc. In some embodiments, $R^1$ may be H, F, or Cl. In some embodiments, $R^1$ may be H.

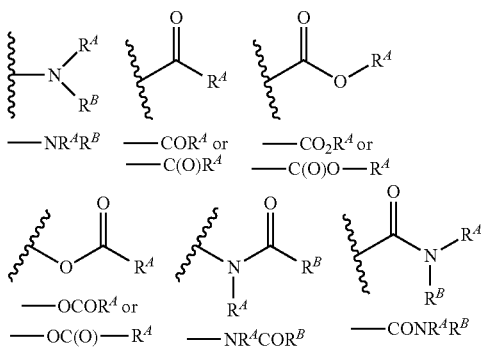

With respect to any relevant structural representation, each $R^A$ may independently be H, or $C_{1-12}$ hydrocarbyl, such as $C_{1-12}$ alkyl, $C_{1-12}$ alkenyl, $C_{1-12}$ alkynyl, phenyl, etc., including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl with a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl with a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

With respect to any relevant structural representation, each $R^B$ may independently be H, or $C_{1-12}$ hydrocarbyl, such as $C_{1-12}$ alkyl, $C_{1-12}$ alkenyl, $C_{1-12}$ alkynyl, phenyl, etc., including: linear or branched alkyl having a formula $C_aH_{2a+1}$, or cycloalkyl having a formula $C_aH_{2a-1}$, wherein a is 1, 2, 3, 4, 5, 6, 7, 8, 9, 10, 11, or 12, such as linear or branched alkyl with a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl with a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to Formula A1, A2, A3, or A4, $R^2$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^2$ may be H, F, Cl, CN, $CF_3$, OH, $NH_2$, $C_{1-6}$ alkyl, or $C_{1-6}$ alkoxy. In some embodiments, $R^2$ may be H, F, or Cl. In some embodiments, $R^2$ may be H.

With respect to Formula A1, A2, A3, or A4, $R^3$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^3$ may be H, F, Cl, CN, $CF_3$, OH, $NH_2$, $C_{1-6}$ alkyl, or $C_{1-6}$ alkoxy. In some embodiments, $R^3$ may be H, F, or Cl. In some embodiments, $R^3$ may be Cl. In some embodiments, $R^3$ may be H.

With respect to Formula A1, A2, A3, or A4, $R^4$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^4$ may be H, F, Cl, CN, $CF_3$, OH, $NH_2$, $C_{1-6}$ alkyl, or $C_{1-6}$ alkoxy. In some embodiments, $R^4$ may be H.

With respect to Formula A1, A2, A3, or A4, $R^5$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^5$ may be H, F, Cl, CN, $CF_3$, OH, $NH_2$, $C_{1-6}$ alkyl, or $C_{1-6}$ alkoxy. In some embodiments, $R^5$ may be H. In some embodiments, $R^5$ may be Cl.

With respect to Formula A1, A2, A3, or A4, in some embodiments $R^1$ is H and $R^3$ is Cl. In some embodiments, $R^2$ is H and $R^3$ is Cl. In some embodiments, $R^1$ and $R^2$ are H and $R^3$ is Cl. In some embodiments, $R^1$, $R^2$, and $R^4$ are H, and $R^3$ is Cl. In some embodiments, $R^1$, $R^2$, $R^4$, and $R^5$ are H, and $R^3$ is Cl. In some embodiments, $R^1$, $R^2$, $R^4$, and $R^5$ are H, and $R^3$ is Br. In some embodiments, $R^1$, $R^2$, $R^4$, and $R^5$ is H, and $R^3$ is F. In some embodiments, $R^1$, $R^2$, $R^4$, and $R^5$ are H.

With respect to Formula A5, $R^{1a}$, $R^{2a}$, $R^{3a}$, $R^{4a}$, $R^{5a}$, $R^{6a}$, $R^{7a}$, $R^{8a}$, $R^{9a}$, and $R^{10a}$ are independently H or any substituent, such as $R^A$, F, Cl, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{1a}$, $R^{2a}$, $R^{3a}$, $R^{4a}$, $R^{5a}$, $R^{6a}$, $R^{7a}$, $R^{8a}$, $R^{9a}$, and $R^{10a}$ may be independently H; F; Cl; $CF_3$; OH;

NH$_2$; C$_{1-6}$ alkyl, such as methyl, ethyl, a propyl isomer (e.g. n-propyl or isopropyl), cyclopropyl, a butyl isomer, a cyclobutyl isomer (e.g. cyclobutyl or methylcyclopropyl), a pentyl isomer, a cyclopentyl isomer, a hexyl isomer, and one of cyclohexyl isomer, etc.; or C$_{1-6}$ alkoxy, such as —O—methyl, —O-ethyl, an isomer of —O-propyl, —O-cyclopropyl, an isomer of —O-butyl, an isomer of —O-cyclobutyl, an isomer of —O-pentyl, an isomer of —O-cyclopentyl, an isomer of —O-hexyl, an isomer of —O-cyclohexyl, etc. In some embodiments, R$^{1a}$, R$^{2a}$, R$^{3a}$, R$^{4a}$, R$^{5a}$, R$^{6a}$, R$^{7a}$, R$^{8a}$, R$^{9a}$, and R$^{10a}$ may be independently H, F, Cl, or CF$_3$. In some embodiments, R$^{1a}$, R$^{2a}$, R$^{3a}$, R$^{4a}$, R$^{5a}$, R$^{6a}$, R$^{7a}$, R$^{8a}$, R$^{9a}$, and R$^{10a}$ may be independently CF$_3$. In some embodiments, R$^{1a}$, R$^{2a}$, R$^{3a}$, R$^{4a}$, R$^{5a}$, R$^{6a}$, R$^{7a}$, R$^{8a}$, R$^{9a}$, and R$^{10a}$ may be independently H.

With respect to Formula 1, L is a linking group represented by an empirical formula: C$_{1-12}$H$_{0-23}$N$_{0-2}$O$_{1-2}$S$_{0-1}$. In some embodiments, L is L$^1$-L$^2$-L$^3$.

With respect to L, L$^1$ is a covalent bond, C(R$^A$)(R$^B$), O, NR$^A$, C(O), or S(O)$_2$, wherein R$^A$ and R$^B$ are independently H or C$_{1-12}$ hydrocarbyl. In some embodiments, L$^1$ is a covalent bond. In some embodiments, L$^1$ is NR$^A$. In some embodiments, L$^1$ is C(O). In some embodiments, L$^1$ is C(R$^A$)(R$^B$).

With respect to L, L$^2$ is a covalent bond, C(R$^A$)(R$^B$), O, NR$^A$, C(O), or S(O)$_2$, wherein R$^A$ and R$^B$ are independently H or C$_{1-12}$ hydrocarbyl. In some embodiments, L$^2$ is a covalent bond. In some embodiments, L$^2$ is C(O). In some embodiments, L$^2$ is S(O)$_2$.

With respect to L, L$^3$ is a covalent bond, C(R$^A$)(R$^B$), O, NR$^A$, C(O), or S(O)$_2$, —wherein R$^A$ and R$^B$ are independently H or C$_{1-12}$ hydrocarbyl. In some embodiments, L$^3$ is a covalent bond. In some embodiments, L$^3$ is NR$^A$. In some embodiments, L$^3$ is O. In some embodiments, L$^3$ is C(R$^A$)(R$^B$).

With respect to Formula 1, in some embodiments, L is —C(O)—, —OC(O)—, —C(O)O—, —C(O)N(R$^A$)—, —N(R$^A$)C(O)—, —N(R$^A$)C(O)N(R$^B$)—, —OC(O)N(R$^A$)—, —N(R$^A$)C(O)O—, —S(O)$_2$—, —OS(O)$_2$—, —S(O)$_2$O—, —S(O)$_2$N(R$^A$)—, —N(R$^A$)S(O)$_2$—, —N(R$^A$)S(O)$_2$N(R$^B$)—, —OS(O)$_2$N(R$^A$)—, or —N(R$^A$)S(O)$_2$—. In some embodiments, L is —C(R$^A$)(CF$_3$)(NR$^A$)—, —C(O)N(R$^A$)—, —N(R$^A$)C(O)—, —NR$^A$—C(O)N(R$^B$)—, —C(O)NR$^A$—C(R$^B$)(R$^C$)—, —NR$^A$—C(R$^B$)(R$^C$)C(O)—, —NR$^A$—C(O)O—, —NR$^A$—S(O)$_2$—, or —NR$^A$—S(O)$_2$N(R$^B$)—, wherein R$^A$, R$^B$, and R$^C$ are independently H or C$_{1-12}$ hydrocarbyl. In some embodiments, L is —CH(CF$_3$)(NH)—, —C(O)NH—, —NH—C(O)—, —NH—C(O)N(R$^A$)—, —C(O)NH—C(R$^A$)(R$^B$)—, —NH—C(R$^A$)(R$^B$)C(O)—, —NH—C(O)O—, —NH—S(O)$_2$—, or —NH—S(O)$_2$N(R$^A$)—. In some embodiments, L is —N(R$^A$)C(O)—. In some embodiments, L is —NHC(O)—. In some embodiments, L is —C(O)N(R$^A$)—. In some embodiments, L is —C(O)NH—.

With respect to Formula 1, D is optionally substituted spiro[2.5]octanyl or optionally substituted 6-azaspiro[2.5]octanyl, which attaches at the 1 and 6 positions; or optionally substituted spiro[3.5]nonanyl, or optionally substituted 7-azaspiro[3.5]nonanyl, which attaches at the 1 and 7 or 2 and 7 positions; or optionally substituted spiro[4.5]decanyl, or optionally substituted 8-azaspiro[4.5]decanyl compounds, which attaches at the 1 and 8-positions. Potential substituents of D may include halo, such as F, Cl, Br, or I; hydrocarbyl, such as methyl, C$_2$ alkyl, C$_2$ alkenyl, C$_2$ alkynyl, C$_3$ alkyl, C$_3$ cycloalkyl, C$_3$ alkenyl, C$_3$ alkynyl, C$_4$ alkyl, C$_4$ cycloalkyl, C$_4$ alkenyl, C$_4$ alkynyl, C$_5$ alkyl, C$_5$ cycloalkyl, C$_5$ alkenyl, C$_5$ alkynyl, C$_6$ alkyl, C$_6$ cycloalkyl, C$_6$ alkenyl, C$_6$ alkynyl, or phenyl, etc.; CN$_{0-1}$O$_{0-2}$F$_{0-3}$H$_{0-4}$; C$_2$N$_{0-1}$O$_{0-3}$F$_{0-5}$H$_{0-6}$; C$_3$N$_{0-1}$O$_{0-3}$F$_{0-7}$H$_{0-8}$; C$_4$N$_{0-1}$O$_{0-3}$F$_{0-9}$H$_{0-10}$; C$_5$N$_{0-1}$O$_{0-3}$F$_{0-11}$H$_{0-12}$; or C$_6$N$_{0-1}$O$_{0-3}$F$_{0-13}$H$_{0-14}$; etc.

With respect to Formula 1, in some embodiments, D is unsubstituted spiro[2.5]octanyl. In some embodiments, D is substituted spiro[2.5]octanyl having 1, 2, 3, 4, 5, 6, 7, 8, 9, 10, 11, or 12 substituents, such as F, Cl, Br, C$_{1-6}$ alkyl, —CO$_2$H, —CHO, CN, CO—C$_{1-6}$ alkyl, —C(O)O—C$_{1-6}$ alkyl, C$_{1-6}$ alkyl-OH, OH, NH$_2$, etc.

With respect to Formula 1, in some embodiments, D is unsubstituted azaspiro[2.5]octanyl. In some embodiments, D is substituted azaspiro[2.5]octanyl. In some embodiments, D is unsubstituted 6-azaspiro[2.5]octanyl. In some embodiments, D is substituted 6-azaspiro[2.5]octanyl having 1, 2, 3, 4, 5, 6, 7, 8, 9, 10, 11, or 12 substituents, such as F, Cl, Br, C$_{1-6}$ alkyl, —CO$_2$H, —CHO, CN, —CO—C$_{1-6}$ alkyl, —C(O)O—C$_{1-6}$ alkyl, C$_{1-6}$ alkyl-OH, OH, NH$_2$, etc.

With respect to Formula 1, in some embodiments, D is unsubstituted spiro[3.5]nonanyl. In some embodiments, D is substituted spiro[3.5]nonanyl having 1, 2, 3, 4, 5, 6, 7, 8, 9, 10, 11, 12, 13, or 14 substituents, such as F, Cl, Br, C$_{1-6}$ alkyl, —CO$_2$H, —CHO, CN, CO—C$_{1-6}$ alkyl, —C(O)O—C$_{1-6}$ alkyl, C$_{1-6}$ alkyl-OH, OH, NH$_2$, etc. In some embodiments, D is unsubstituted 7-azaspiro[3.5]nonanyl. In some embodiments, D is substituted 7-azaspiro[3.5]nonanyl having 1, 2, 3, 4, 5, 6, 7, 8, 9, 10, 11, 12, 13, or 14 substituents, such as F, Cl, Br, C$_{1-6}$ alkyl, —CO$_2$H, —CHO, CN, —CO—C$_{1-6}$ alkyl, —C(O)O—C$_{1-6}$ alkyl, C$_{1-6}$ alkyl-OH, OH, NH$_2$, etc.

With respect to Formula 1, in some embodiments, D is unsubstituted spiro[4.5]decanyl. In some embodiments, D is substituted spiro[4.5]decanyl having 1, 2, 3, 4, 5, 6, 7, 8, 9, 10, 11, 12, 13, 14, 15, or 16 substituents, such as F, Cl, Br, C$_{1-6}$ alkyl, —CO$_2$H, —CHO, CN, CO—C$_{1-6}$ alkyl, —C(O)O—C$_{1-6}$ alkyl, C$_{1-6}$ alkyl-OH, OH, NH$_2$, etc. In some embodiments, D is unsubstituted 8-azaspiro[4.5]decanyl. In some embodiments, D is substituted 8-azaspiro[4.5]decanyl having 1, 2, 3, 4, 5, 6, 7, 8, 9, 10, 11, 12, 13, 14, 15, or 16 substituents, such as F, Cl, Br, C$_{1-6}$ alkyl, —CO$_2$H, —CHO, CN, CO—C$_{1-6}$ alkyl, —C(O)O—C$_{1-6}$ alkyl, C$_{1-6}$ alkyl-OH, OH, NH$_2$, etc.

In some embodiments, D is represented by formula D1, D2, D3, D4, D5, D6, D7, D8, D9, or D10:

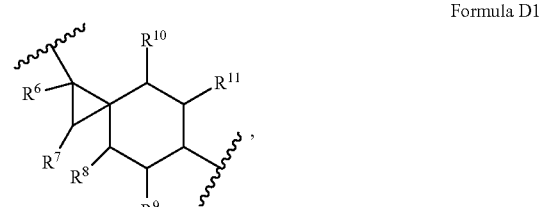

Formula D1

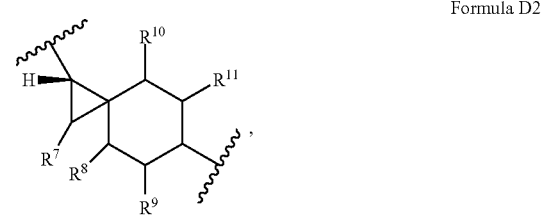

Formula D2

-continued

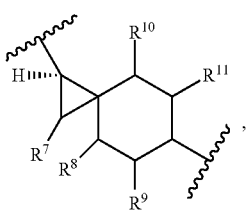

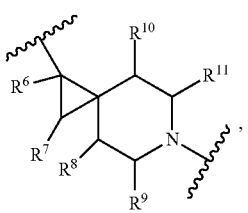

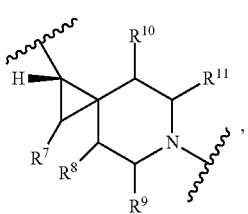

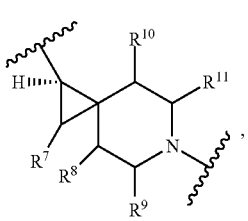

Formula D7-1

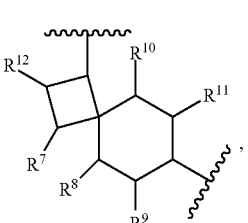

Formula D7-2

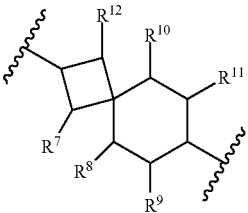

Formula D8-1

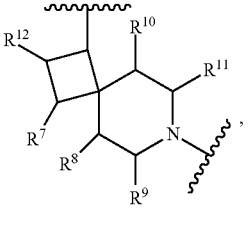

-continued

Formula D3

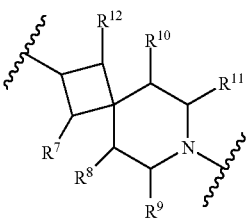

Formula D4

Formula D5

Formula D6

Formula D8-2

Formula D9

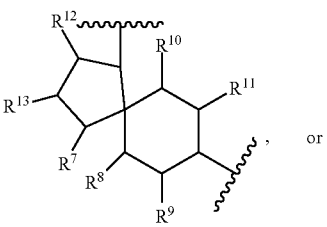

Formula D10

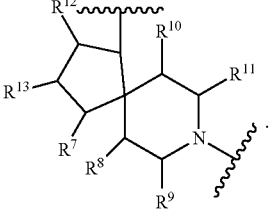

With respect to Formula D1 or D4, $R^6$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^6$ may be H, F, Cl, CN, $CF_3$, OH, $NH_2$, $C_{1-6}$ alkyl, or $C_{1-6}$ alkoxy. In some embodiments, $R^6$ may be H. In some embodiments, $R^6$ may be F. In some embodiments, $R^6$ may be $CH_3$.

With respect to Formula D1, D2, D3, D4, D5, D6, D7-1, D7-2, D8-1, D8-2, D9 or D10, $R^7$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^7$ may be H, F, Cl, CN, $CF_3$, OH, $NH_2$, $C_{1-6}$ alkyl, or $C_{1-6}$ alkoxy. In some embodiments, $R^7$ may be H.

With respect to Formula D1, D2, D3, D4, D5, D6, D7-1, D7-2, D8-1, D8-2, D9 or D10, $R^8$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^8$ may be H, F, Cl, CN, $CF_3$, OH, $NH_2$, $C_{1-6}$ alkyl, or $C_{1-6}$ alkoxy. In some embodiments, $R^8$ may be H.

With respect to Formula D1, D2, D3, D4, D5, D6, D7-1, D7-2, D8-1, D8-2, D9 or D10, $R^9$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^9$ may be H, F, Cl, CN, $CF_3$, OH, $NH_2$, $C_{1-6}$ alkyl, or $C_{1-6}$ alkoxy. In some embodiments, $R^9$ may be H.

With respect to Formula D1, D2, D3, D4, D5, D6, D7-1, D7-2, D8-1, D8-2, D9 or D10, $R^{10}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^{10}$ may be H, F, Cl, CN, $CF_3$, OH, $NH_2$, $C_{1-6}$ alkyl, or $C_{1-6}$ alkoxy. In some embodiments, $R^{10}$ may be H.

With respect to Formula D1, D2, D3, D4, D5, D6, D7-1, D7-2, D8-1, D8-2, D9 or D10, $R^{11}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^{11}$ may be H, F, Cl, CN, $CF_3$, OH, $NH_2$, $C_{1-6}$ alkyl, or $C_{1-6}$ alkoxy. In some embodiments, $R^{11}$ may be H.

With respect to Formula D1, D2, D3, D4, D5, D6, D7-1, D7-2, D8-1, D8-2, D9 or D10, $R^{12}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^{12}$ may be H, F, Cl, CN, $CF_3$, OH, $NH_2$, $C_{1-6}$ alkyl, or $C_{1-6}$ alkoxy. In some embodiments, $R^{12}$ may be H.

With respect to Formula D1, D2, D3, D4, D5, D6, D7-1, D7-2, D8-1, D8-2, D9 or D10, $R^{13}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^{13}$ may be H, F, Cl, CN, $CF_3$, OH, $NH_2$, $C_{1-6}$ alkyl, or $C_{1-6}$ alkoxy. In some embodiments, $R^{13}$ may be H.

With respect to Formula 1, E is optionally substituted $C_{6-10}$ aryl or optionally substituted $C_{3-9}$ heteroaryl. In some embodiments, E is optionally substituted quinolinyl, such as optionally substituted quinolin-4-yl. Potential substituents of E may include halo, such as F, Cl, Br, I; hydrocarbyl, such as methyl, $C_2$ alkyl, $C_2$ alkenyl, $C_2$ alkynyl, $O_3$ alkyl, $O_3$ cycloalkyl, $O_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; $C_6N_{0-1}O_{0-3}F_{0-13}H_{0-14}$; etc. In some embodiments, E is optionally substituted quinolinyl, such as optionally substituted quinolin-4-yl having 0, 1, 2, 3, 4, 5, or 6 substituents, such as quinolinyl or quinolin-4-yl, having substituents such as F, Cl, Br, $C_{1-6}$ alkyl, —$CO_2H$, —CHO, CN, CO—$C_{1-6}$ alkyl, —C(O)O—$C_{1-6}$ alkyl, $C_{1-6}$ alkyl-OH, OH, $NH_2$, etc. In some embodiments, E is unsubstituted quinolin-4-yl. In some embodiments, E is optionally substituted 6-fluoroquinolin-4-yl.

With respect to Formula 1, in some embodiments, E is represented by Formula E1, E2, E3, or E4:

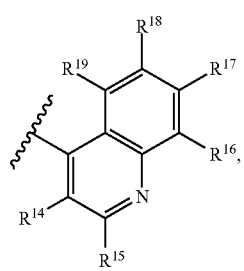

Formula E1

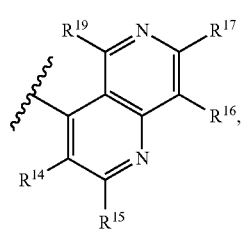

Formula E2

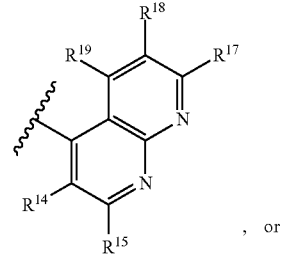

Formula E3

, or

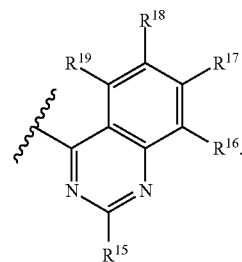

Formula E4

With respect to Formula E1, E2, or E3, $R^{14}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, —$CONR^AR^B$, etc. In some embodiments, $R^{14}$ may be H, F, Cl, CN, $CF_3$, OH, $NH_2$, $C_{1-6}$ alkyl, or $C_{1-6}$ alkoxy. In some embodiments, $R^{14}$ may be H.

With respect to Formula E1, E2, E3, or E4, $R^{15}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, —$CONR^AR^B$, etc. In some embodiments, $R^{15}$ may be H, F, Cl, CN, $CF_3$, OH, $NH_2$, $C_{1-6}$ alkyl, or $C_{1-6}$ alkoxy. In some embodiments, $R^{15}$ may be F.

With respect to Formula E1, E2, or E4, $R^{16}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, —$CONR^AR^B$, etc. In some embodiments, $R^{16}$ may be H, F, Cl, CN, $CF_3$, OH, $NH_2$, $C_{1-6}$ alkyl, or $C_{1-6}$ alkoxy. In some embodiments, $R^{16}$ may be H.

With respect to Formula E1, E2, E3, or E4, $R^{17}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, —$CONR^AR^B$, etc. In some embodiments, $R^{17}$ may be H, F, Cl, CN, $CF_3$, OH, $NH_2$, $C_{1-6}$ alkyl, or $C_{1-6}$ alkoxy. In some embodiments, $R^{17}$ may be H.

With respect to Formula E1, E3, or E4, $R^{18}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, —$CONR^AR^B$, etc. In some embodiments, $R^{18}$ may be H, F, Cl, CN, $CF_3$, OH, $NH_2$, $C_{1-6}$ alkyl, or $C_{1-6}$ alkoxy. In some embodiments, $R^{18}$ may be H.

With respect to Formula E1, E2, E3, or E4, $R^{19}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, —$CONR^AR^B$, etc. In some embodiments, $R^{19}$ may be H, F, Cl, CN, $CF_3$, OH, $NH_2$, $C_{1-6}$ alkyl, or $C_{1-6}$ alkoxy. In some embodiments, $R^{19}$ may be H.

With respect to Formula 2, in some embodiments, $A^1$ is represented by Formula A1, A2, A3, A4, or A5:

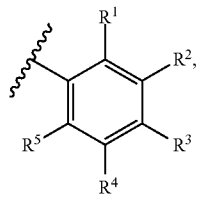

Formula A1

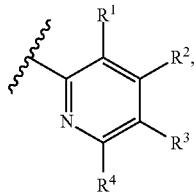

Formula A2

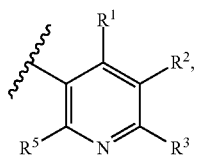

Formula A3

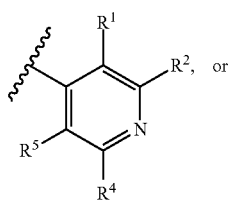

Formula A4 or

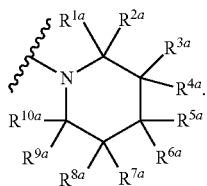

Formula A5

With respect to Formula A1, A2, A3, or A4, $R^1$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^1$ may be H; F; Cl; CN; $CF_3$; OH; $NH_2$; $C_{1-6}$ alkyl, such as methyl, ethyl, a propyl isomer (e.g. n-propyl or isopropyl), cyclopropyl, a butyl isomer, a cyclobutyl isomer (e.g. cyclobutyl or methylcyclopropyl), a pentyl isomer, a cyclopentyl isomer, a hexyl isomer, and one of cyclohexyl isomer, etc.; or $C_{1-6}$ alkoxy, such as —O-methyl, —O-ethyl, an isomer of —O-propyl, —O-cyclopropyl, an isomer of —O-butyl, an isomer of —O-cyclobutyl, an isomer of —O-pentyl, an isomer of —O-cyclopentyl, an isomer of —O-hexyl, an isomer of —O-cyclohexyl, etc. In some embodiments, $R^1$ may be H, F, or Cl. In some embodiments, $R^1$ may be H.

With respect to any relevant structural representation, $R^A$ and $R^B$ are the same as that defined in Formula A1, A2, A3, or A4 for Formula 1.

With respect to Formula A1, A2, A3, or A4, $R^2$, $R^3$, $R^4$, or $R^5$ is the same as that defined above, in Formula 1.

With respect to Formula A1, A2, A3, or A4, in some embodiments $R^1$ is H and $R^3$ is Cl. In some embodiments, $R^2$ is H and $R^3$ is Cl. In some embodiments, $R^1$ and $R^2$ are H and $R^3$ is Cl. In some embodiments, $R^1$, $R^2$, and $R^4$ are H, and $R^3$ is Cl. In some embodiments, $R^1$, $R^2$, $R^4$, and $R^5$ are H, and $R^3$ is Cl.

With respect to Formula A5, $R^{1a}$, $R^{2a}$, $R^{3a}$, $R^{4a}$, $R^{5a}$, R6a, $R^{7a}$, $R^{8a}$, $R^{9a}$, and $R^{10a}$ are independently H or any substituent, such as $R^A$, F, Cl, —$OR^A$, $CF_3$, —$NR^AR^B$, —$COR^A$, —$CO_2R^A$, —$OCOR^A$, —$NR^ACOR^B$, or —$CONR^AR^B$, etc. In some embodiments, $R^{1a}$, $R^{2a}$, $R^{3a}$, $R^{4a}$, $R^{5a}$, $R^{6a}$, $R^{7a}$, $R^{8a}$, $R^{9a}$, and $R^{10a}$ may be independently H; F; Cl; $CF_3$; OH; $NH_2$; $C_{1-6}$ alkyl, such as methyl, ethyl, a propyl isomer (e.g. n-propyl or isopropyl), cyclopropyl, a butyl isomer, a cyclobutyl isomer (e.g. cyclobutyl or methylcyclopropyl), a pentyl isomer, a cyclopentyl isomer, a hexyl isomer, a cyclohexyl isomer, etc.; or $C_{1-6}$ alkoxy, such as —O-methyl, —O-ethyl, an isomer of —O-propyl, —O-cyclopropyl, an isomer of —O-butyl, an isomer of —O-cyclobutyl, an isomer of —O-pentyl, an isomer of —O-cyclopentyl, an isomer of —O-hexyl, an isomer of —O-cyclohexyl, etc. In some embodiments, $R^{1a}$, $R^{2a}$, $R^{3a}$, $R^{4a}$, $R^{5a}$, $R^{6a}$, $R^{7a}$, $R^{8a}$, $R^{9a}$, and $R^{1a}$ may be independently H, F, Cl, or $CF_3$. In some embodiments, $R^{1a}$, $R^{2a}$, $R^{3a}$, $R^{4a}$, $R^{5a}$, $R^{6a}$, $R^{7a}$, $R^{8a}$, $R^{9a}$, and $R^{10a}$ may be independently $CF_3$. In some embodiments, $R^{1a}$, $R^{2a}$, $R^{3a}$, $R^{4a}$, $R^{5a}$, $R^{6a}$, $R^{7a}$, $R^{8a}$, $R^{9a}$, and $R^{10a}$ may be independently H.

With respect to Formula 2, in some embodiments, Formula 2 is further represented by Formula 2A or Formula 2B:

$$E^1\text{-}D^1\text{-}N(H)C(O)\text{-}A^1 \qquad \text{(Formula 2A), or}$$

$$E^1\text{-}D^1\text{-}C(O)N(H)\text{-}A^1 \qquad \text{(Formula 2B).}$$

With respect to Formula 2, $L^1$ is —C(O)—NH— or —N(H)—C(O)—, wherein $L^1$ is directly attached to the cyclopropyl ring of $D^1$. In some embodiments, C(O) of $L^1$ is directly attached to the cyclohexane or piperidine ring of $D^1$. In some embodiments, N(H) of $L^1$ is directly attached to the cyclohexane or piperidine ring of $D^1$. In some embodiments, $L^1$ is —C(O)—NH—. In some embodiments, $L^1$ is —N(H)—C(O)—.

With respect to Formula 2, 2A, or 2B, $D^1$ is optionally substituted ($1\lambda^3$-cyclopropyl)-$4\lambda^3$-cyclohexane, or 4-($1\lambda^3$-cyclopropyl)-$1\lambda^3$-piperidine. Potential substituents of $D^1$ may include halo, such as F, Cl, Br, or I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, $C_6$ alkyl, $C_6$ cycloalkyl, $C_6$ alkenyl, $C_6$ alkynyl, or phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; or $C_6N_{0-1}O_{0-3}F_{0-13}H_{0-14}$; etc.

With respect to Formula 2, 2A, or 2B, in some embodiments, $D^1$ is unsubstituted ($1\lambda^3$-cyclopropyl)-$4\lambda^3$-cyclohexane. In some embodiments, $D^1$ is substituted ($1\lambda^3$-cyclopropyl)-$4\lambda^3$-cyclohexane having 1, 2, 3, 4, 5, 6, 7, 8, 9, 10, 11, 12, 13, or 14 substituents, such as F, Cl, Br, $C_{1-6}$ alkyl, —$CO_2H$, —CHO, CN, CO—$C_{1-6}$ alkyl, —C(O)O— $C_{1-6}$ alkyl, $C_{1-6}$ alkyl-OH, OH, $NH_2$, etc.

With respect to Formula 2, 2A, or 2B, in some embodiments, $D^1$ is unsubstituted 4-($1\lambda^3$-cyclopropyl)-$1\lambda^3$-piperidine. In some embodiments, $D^1$ is substituted 4-($1\lambda^3$-cyclopropyl)-$1\lambda^3$-piperidine having 1, 2, 3, 4, 5, 6, 7, 8, 9, 10, 11, 12, or 13 substituents, such as F, Cl, Br, $C_{1-6}$ alkyl, —$CO_2H$, —CHO, CN, —CO—$C_{1-6}$ alkyl, —C(O)O—$C_{1-6}$ alkyl, $C_{1-6}$ alkyl-OH, OH, $NH_2$, etc.

In some embodiments, D¹ is represented by formula D11 or D12:

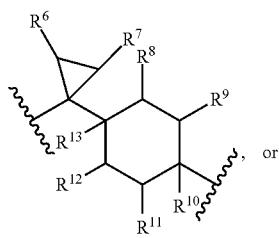

Formula D11

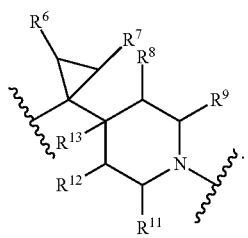

Formula D12

With respect to Formula D11 or D12, $R^6$, $R^7$, $R^8$, $R^9$, $R^{10}$, $R^{11}$, or $R^{12}$ is the same as that defined in Formula D1, D2, D3, D4, D5, D6, D7, D8, D9, or D10 for Formula 1.

With respect to Formula D11 or D12, $R^{13}$ is H or any substituent, such as $R^A$, F, Cl, CN, —$OR^A$, $CF_3$, —$NO_2$, —$NR^AR^B$, —$COR^A$, —$CO_2R^A$, —$OCOR^A$, —$NR^ACOR^B$, or —$CONR^AR^B$, etc. In some embodiments, $R^{13}$ may be H, F, Cl, CN, $CF_3$, OH, $NH_2$, $C_{1-6}$ alkyl, or $C_{1-6}$ alkoxy. In some embodiments, $R^{13}$ may be H.

With respect to Formula 2, 2A, or 2B, E¹ is optionally substituted $C_{6-10}$ aryl or optionally substituted $C_{3-9}$ heteroaryl. In some embodiments, E¹ is optionally substituted $C_{6-10}$ aryl. In some embodiments, E¹ is optionally substituted $C_{3-9}$ heteroaryl. In some embodiments, E¹ is optionally substituted quinolinyl, such as optionally substituted quinolin-4-yl. Potential substituents of E¹ may include halo, such as F, Cl, Br, I; hydrocarbyl, such as methyl, $C_2$ alkyl, $C_2$ alkenyl, $C_2$ alkynyl, $C_3$ alkyl, $C_3$ cycloalkyl, $C_3$ alkenyl, $C_3$ alkynyl, $C_4$ alkyl, $C_4$ cycloalkyl, $C_4$ alkenyl, $C_4$ alkynyl, $C_5$ alkyl, $C_5$ cycloalkyl, $C_5$ alkenyl, $C_5$ alkynyl, 06 alkyl, 06 cycloalkyl, 06 alkenyl, $C_6$ alkynyl, phenyl, etc.; $CN_{0-1}O_{0-2}F_{0-3}H_{0-4}$; $C_2N_{0-1}O_{0-3}F_{0-5}H_{0-6}$; $C_3N_{0-1}O_{0-3}F_{0-7}H_{0-8}$; $C_4N_{0-1}O_{0-3}F_{0-9}H_{0-10}$; $C_5N_{0-1}O_{0-3}F_{0-11}H_{0-12}$; $C_6N_{0-1}O_{0-3}F_{0-13}H_{0-14}$; etc. In some embodiments, E¹ is optionally substituted quinolinyl, such as optionally substituted quinolin-4-yl having 0, 1, 2, 3, 4, 5, or 6 substituents, such as quinolinyl or quinolin-4-yl, having substituents such as F, Cl, Br, $C_{1-6}$ alkyl, —$CO_2H$, —CHO, CN, CO—$C_{1-6}$ alkyl, —C(O)O—$C_{1-6}$ alkyl, $C_{1-6}$ alkyl-OH, OH, $NH_2$, etc. In some embodiments, E¹ is unsubstituted quinolin-4-yl. In some embodiments, E¹ is optionally substituted 6-fluoroquinolin-4-yl.

With respect to Formula 2, 2A, or 2B, in some embodiments, E¹ is represented by Formula E1, E2, E3, or E4:

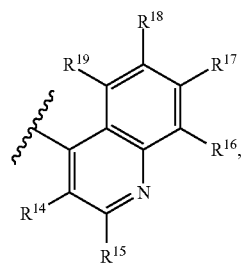

Formula E1

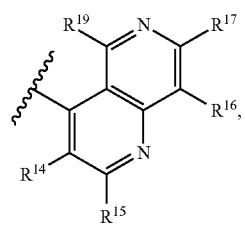

Formula E2

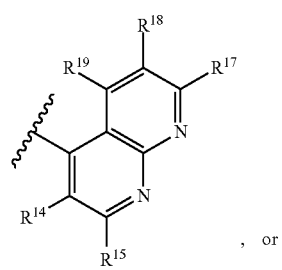

Formula E3, or

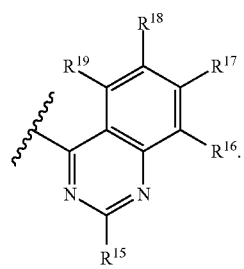

Formula E4

With respect to Formula E1, E2, E3, or E4, $R^{14}$, $R^{15}$, $R^{16}$, $R^{17}$, $R^{18}$ or $R^{19}$ is the same as that defined above in Formula E1, E2, E3, or E4 for Formula 1.

Some embodiments include a compound which is an optionally substituted core structure of any of the compounds prepared (their structures are shown in the Experimental Section) as represented by a compound identification (ID) number in Table A or Table B. The term "core structure" described herein refers to a compound with the structure without any substituent, for example, compound 1-9 (its structure is shown in the Experimental Section) has core structure C-1-9, compound 1-10 has core structure C-1-10; compound 1-11 has core structure C-1-11, compound 23-5A has core structure C-23-5A, or compound 23-5B has core structure C-23-5B, and their structures and names are shown below.

1-9

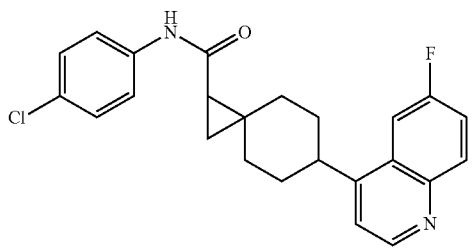

N-(4-chlorophenyl)-6-(6-fluoroquinolin-4-yl)
spiro[2.5]octane-1-carboxamide

C-1-9

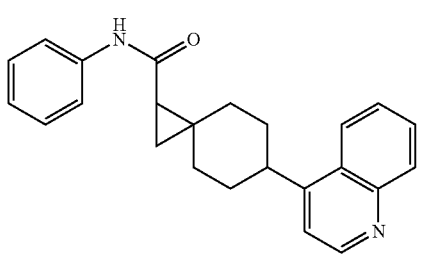

N-phenyl-6-(quinolin-4-yl)
spiro[2.5]octane-1-carboxamide 1-10

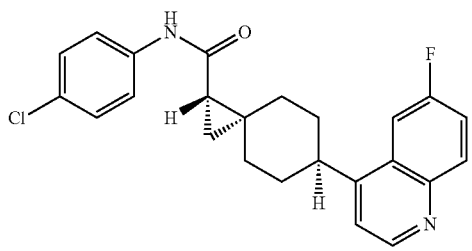

(1S,3s,6R)-N-(4-chlorophenyl)-6-(6-fluoroquinolin-4-yl)
spiro[2.5]octane-1-carboxamide

C-1-10

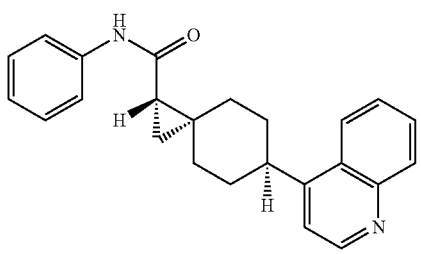

(1S,3s,6R)-N-phenyl-6-(quinolin-4-yl)
spiro[2.5]octane-1-carboxamide 1-11

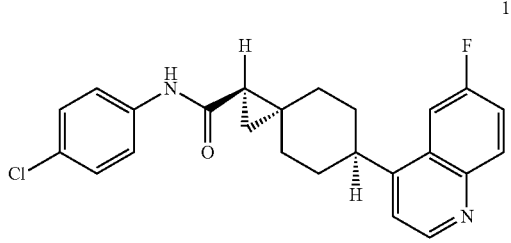

(1R,3s,6S)-N-(4-chlorophenyl)-6-(6-fluoroquinolin-4-yl)
spiro[2.5]octane-1-carboxamide

C-1-11

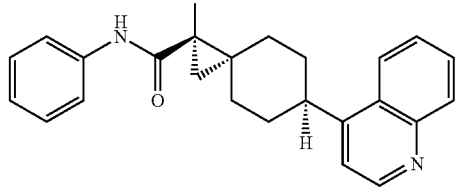

(1R,3s,6S)-N-phenyl-6-(quinolin-4-yl)
spiro[2.5]octane-1-carboxamide 23-5A

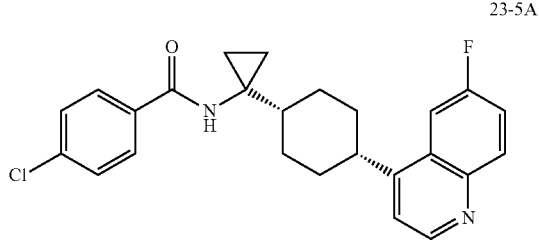

4-chloro-N-(1-((1s,4s)-4-(6-fluoroquinolin-4-yl)
cyclohexyl)cyclopropyl)benzamide

C-23-5A

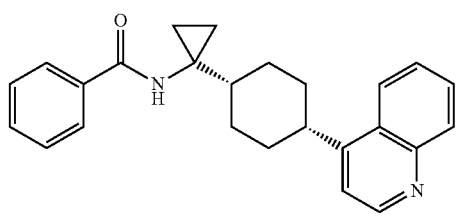

N-(1-((1s,4s)-4-(quinolin-4-yl)cyclohexyl)
cyclopropyl)benzamide 23-5B

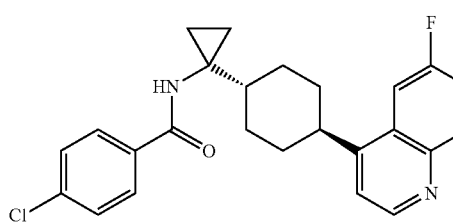

4-chloro-N-(1-((1r,4r)-4-(6-fluoroquinolin-4-yl)
cyclohexyl)cyclopropyl)benzamide

C-23-5B

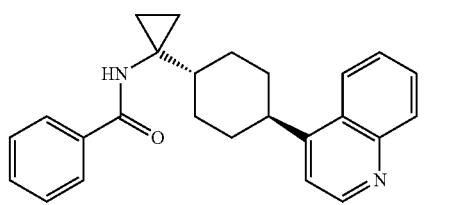

N-(1-((1r,4r)-4-(quinolin-4-yl)cyclohexyl)
cyclopropyl)benzamide

Similarly, other compounds with the corresponding core structures of the compounds prepared are represented in Table A and Table B below.

TABLE A

Compound identification numbers for the compounds prepared and the compounds with their corresponding core structures represented by Formula 1.

| Compound Prepared | Compound with Core Structure | Compound Prepared | Compound With Core Structure |
|---|---|---|---|
| 1-9 | C-1-9 | 1-10 | C-1-10 |
| 1-11 | C-1-11 | 1-12 | C-1-12 |
| 1-13 | C-1-13 | 1-14 | C-1-14 |
| 1-15 | C-1-15 | 1-16 | C-1-16 |
| 1-17 | C-1-17 | 1-18 | C-1-18 |
| 1-19 | C-1-19 | 1-20 | C-1-20 |
| 1-21 | C-1-21 | 1-22 | C-1-22 |
| 1-23 | C-1-23 | 2-1 | C-2-1 |
| 2-2 | C-2-2 | 2-3 | C-2-3 |
| 2-4 | C-2-4 | 2-5 | C-2-5 |
| 2-6 | C-2-6 | 3-2 | C-3-2 |
| 3-3 | C-3-3 | 4-4 | C-4-4 |
| 4-5 | C-4-5 | 4-6 | C-4-6 |
| 4-7 | C-4-7 | 4-8 | C-4-8 |
| 4-9 | C-4-9 | 5-4 | C-5-4 |
| 6-9 | C-6-9 | 7-6 | C-7-6 |
| 7-7 | C-7-7 | 8-4A | C-8-4A |
| 8-4B | C-8-4B | 8-4C | C-8-4C |
| 8-4D | C-8-4D | 8-4E | C-8-4E |
| 8-4F | C-8-4F | 9-3 | C-9-3 |
| 9-4 | C-9-4 | 9-5 | C-9-5 |
| 9-6 | C-9-6 | 9-7 | C-9-7 |
| 9-8 | C-9-8 | 9-9 | C-9-9 |
| 10-4 | C-10-4 | 11-5 | C-11-5 |
| 11-6 | C-11-6 | 12-5 | C-12-5 |
| 12-6 | C-12-6 | 12-7 | C-12-7 |
| 13-3 | C-13-3 | 14-7 | C-14-7 |
| 15-3 | C-15-3 | 16-6 | C-16-6 |
| 16-7 | C-16-7 | 16-8 | C-16-8 |
| 17-6 | C-17-6 | 17-7 | C-17-7 |
| 17-8 | C-17-8 | 17-9 | C-17-9 |
| 18-5 | C-18-5 | 19-3 | C-19-3 |
| 20-8 | C-20-8 | 20-9 | C-20-9 |
| 21-4 | C-21-4 | 21-5 | C-21-5 |
| 22-5 | C-22-5 | | |

TABLE B

Compound identification numbers for the compounds prepared and the compounds with their corresponding core structures represented by Formula 2.

| Compound Prepared | Compound with Core Structure | Compound Prepared | Compound With Core Structure |
|---|---|---|---|
| 23-5A | C-23-5A | 23-5B | C-23-5B |
| 24-5A | C-24-5A | 24-5B | C-24-5B |
| 26-8 | C-26-8 | 27-3 | C-27-3 |
| 28-5 | C-28-5 | 29-6 | C-29-6 |

Some embodiments include an optionally substituted C-1-9, C-1-10, C-1-11, C-1-12, C-1-13, C-1-14, C-1-15, C-1-16, C-1-17, C-1-18, C-1-19, C-1-20, C-1-21, C-1-22, C-1-23, C-2-1, C-2-2, C-2-3, C-2-4, C-2-5, C-2-6, C-3-2, C-3-3, C-4-4, C-4-5, C-4-6, C-4-7, C-4-8, C-4-9, C-5-4, C-6-9, C-7-6, C-7-7, C-8-4A, C-8-4B, C-8-4C, C-8-4D, C-8-4E, C-8-4F, C-9-3, C-9-4, C-9-5, C-9-6, C-9-7, C-9-8, C-9-9, C-10-4, C-11-5, C-11-6, C-12-5, C-12-6, C-12-7, C-13-3, C-14-7, C-15-3, C-16-6, C-16-7, C-16-8, C-17-6, C-17-7, C-17-8, C-17-9, C-18-5, C-19-3, C-20-8, C-20-9, C-21-4, C-21-5, C-22-5, C-23-5A, C-23-5B, C-24-5A, C-24-5B, C-26-8, C-27-3, C-28-5, or C-29-6.

Some embodiments include optionally substituted N-phenyl-6-(quinolin-4-yl)spiro[2.5]octane-1-carboxamide, optionally substituted N-(6-(quinolin-4-yl)spiro[2.5]octan-1-yl)benzamide, optionally substituted N-phenyl-6-(quinolin-4-yl)-6-azaspiro[2.5]octane-1-carboxamide, optionally substituted N-(6-(quinolin-4-yl)-6-azaspiro[2.5]octan-1-yl)benzamide, or an optionally substituted core structure of any of the compounds represented in Table A.

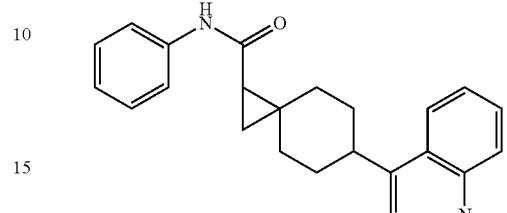

N-phenyl-6-(quinolin-4-yl)spiro[2.5]octane-1-carboxamide

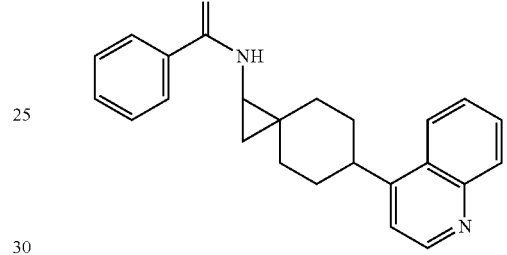

N-(6-(quinolin-4-yl)spiro[2.5]octan-1-yl)benzamide

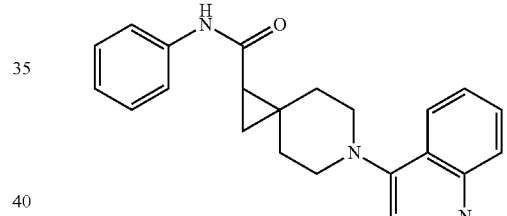

N-phenyl-6-(quinolin-4-yl)-6-azaspiro[2.5]octane-1-carboxamide

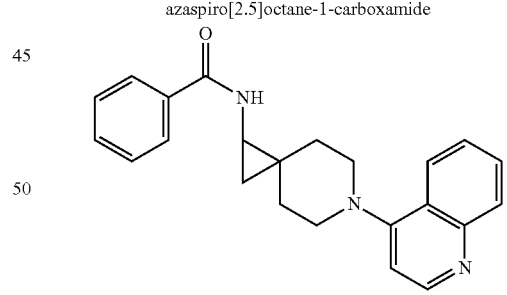

N-(6-(quinolin-4-yl)-6-azaspiro[2.5]octan-1-yl)benzamide

Some embodiments include optionally substituted N-(1-(4-(quinolin-4-yl)cyclohexyl)cyclopropyl)benzamide, optionally substituted N-phenyl-1-(4-(quinolin-4-yl)cyclohexyl)cyclopropane-1-carboxamide, optionally substituted N-phenyl-1-(1-(quinolin-4-yl)piperidin-4-yl)cyclopropane-1-carboxamide, optionally substituted N-(1-(1-(quinolin-4-yl)piperidin-4-yl)cyclopropyl)benzamide, optionally substituted 1-((1s,4s)-4-(1,6-naphthyridin-4-yl)cyclohexyl)-N-phenylcyclopropane-1-carboxamide, or optionally substituted 1-((1r,4r)-4-(1,6-naphthyridin-4-yl)cyclohexyl)-N-phenylcyclopropane-1-carboxamide.

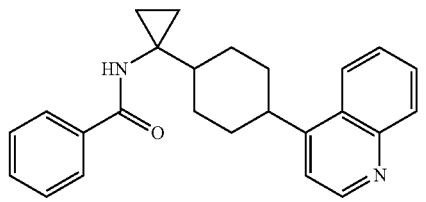

N-(1-(4-(quinolin-4-yl)cyclohexyl)cyclopropyl)benzamide

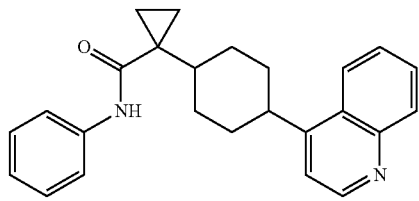

N-phenyl-1-(4-(quinolin-4-yl)cyclohexyl)cyclopropane-1-carboxamide

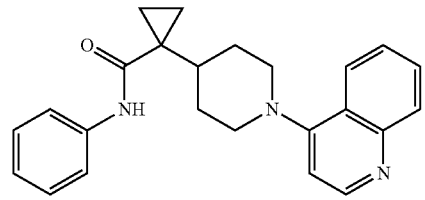

N-phenyl-1-(1-(quinolin-4-yl)piperidin-4-yl)cyclopropane-1-carboxamide

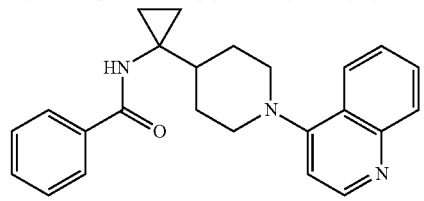

N-(1-(1-(quinolin-4-yl)piperidin-4-yl)cyclopropyl)benzamide

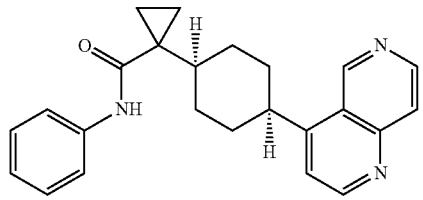

1-((1s,4s)-4-(1,6-naphthyridin-4-yl)cyclohexyl)-N-phenylcyclopropane-1-carboxamide

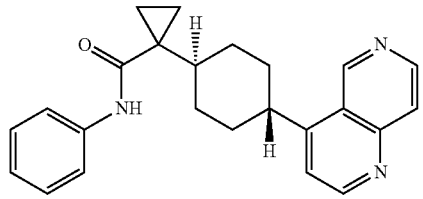

1-((1r,4r)-4-(1,6-naphthyridin-4-yl)cyclohexyl)-N-phenylcyclopropane-1-carboxamide Some embodiments include optionally substituted (R)—N-phenyl-6-(quinolin-4-yl)spiro[2.5]octane-1-carboxamide, optionally substituted (R)—N-(6-(quinolin-4-yl)spiro[2.5]octan-1-yl)benzamide, optionally substituted (R)—N-phenyl-6-(quinolin-4-yl)-6-azaspiro[2.5]octane-1-carboxamide, or optionally substituted (R)—N-(6-(quinolin-4-yl)-6-azaspiro[2.5]octan-1-yl)benzamide.

Some embodiments include optionally substituted (S)—N-phenyl-6-(quinolin-4-yl)spiro[2.5]octane-1-carboxamide, optionally substituted (S)—N-(6-(quinolin-4-yl)spiro[2.5]octan-1-yl)benzamide, optionally substituted (S)—N-phenyl-6-(quinolin-4-yl)-6-azaspiro[2.5]octane-1-carboxamide, or optionally substituted (S)—N-(6-(quinolin-4-yl)-6-azaspiro[2.5]octan-1-yl)benzamide.

Some embodiments include optionally substituted (cis)-N-(1-(4-(quinolin-4-yl)cyclohexyl)cyclopropyl)benzamide, optionally substituted (cis)-N-phenyl-1-(4-(quinolin-4-yl)cyclohexyl)cyclopropane-1-carboxamide, or optionally substituted (cis)-1-(4-(1,6-naphthyridin-4-yl)cyclohexyl)-N-phenylcyclopropane-1-carboxamide.

Some embodiments include optionally substituted (trans)-N-(1-(4-(quinolin-4-yl)cyclohexyl)cyclopropyl)benzamide, optionally substituted (trans)-N-phenyl-1-(4-(quinolin-4-yl)cyclohexyl)cyclopropane-1-carboxamide, or optionally substituted (trans)-1-(4-(1,6-naphthyridin-4-yl)cyclohexyl)-N-phenylcyclopropane-1-carboxamide.

Some embodiments include one of the optionally substituted compounds: 1-9, 1-10, 1-11, 1-12, 1-13, 1-14, 1-15, 1-16, 1-17, 1-18, 1-19, 1-20, 1-21, 1-22, 1-23, 2-1, 2-2, 2-3, 2-4, 2-5, 2-6, 3-2, 3-3, 4-4, 4-5, 4-6, 4-7, 4-8, 4-9, 5-4, 6-9, 7-6, 7-7, 8-4A, 8-4B, 8-4C, 8-4D, 8-4E, 8-4F, 9-3, 9-4, 9-5, 9-6, 9-7, 9-8, 9-9, 10-4, 11-5, 11-6, 12-5, 12-6, 12-7, 13-3, 14-7, 15-3, 16-6, 16-7, 16-8, 17-6, 17-7, 17-8, 17-9, 18-5, 19-3, 20-8, 20-9, 21-4, 21-5, 22-5, 23-5A, 23-5B, 24-5A, 24-5B, 26-8, 27-3, 28-5, or 29-6. Their structures are shown in the Experimental section below.

Some embodiments include one of the compounds below:

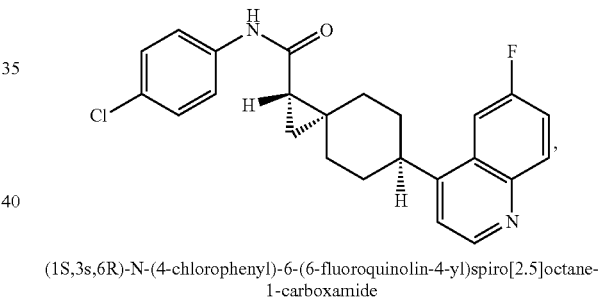

(1S,3s,6R)-N-(4-chlorophenyl)-6-(6-fluoroquinolin-4-yl)spiro[2.5]octane-1-carboxamide

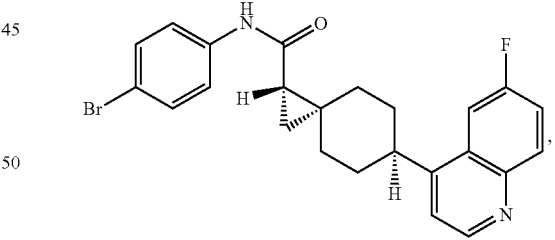

(1S,3s,6R)-N-(4-bromophenyl)-6-(6-fluoroquinolin-4-yl)spiro[2.5]octane-1-carboxamide

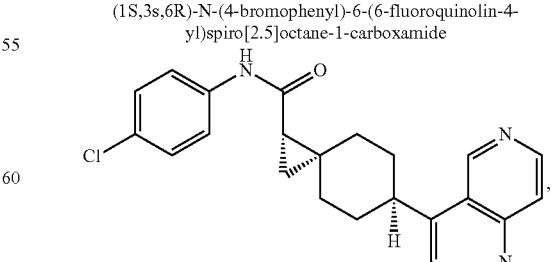

(1S,3s,6R)-N-(4-chlorophenyl)-6-(1,6-naphthyridin-4-yl)spiro[2.5]octane-1-carboxamide

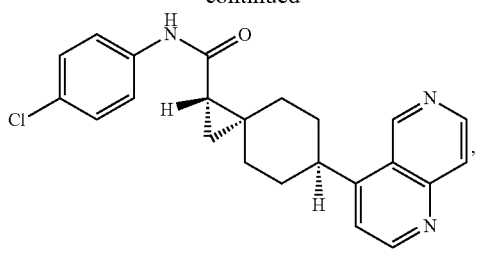

(1S,3s,6R)-N-(4-chlorophenyl)-6-(1,6-naphthyridin-4-yl)spiro[2.5]octane-1-carboxamide

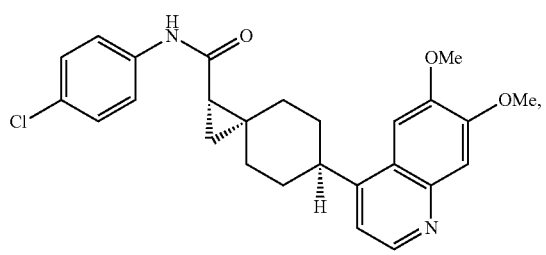

(1S,3s,6R)-N-(4-chlorophenyl)-6-(6,7-dimethoxyquinolin-4-yl)spiro[2.5]octane-1-carboxamide

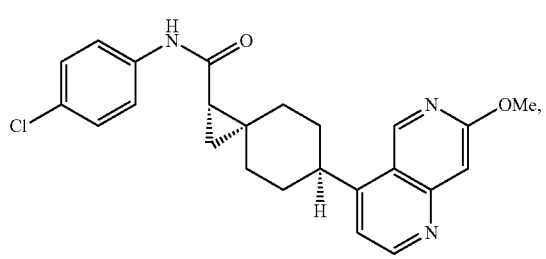

(1S,3s,6R)-N-(4-chlorophenyl)-6-(7-methoxy-1,6-naphthyridin-4-yl)spiro[2.5]octane-1-carboxamide

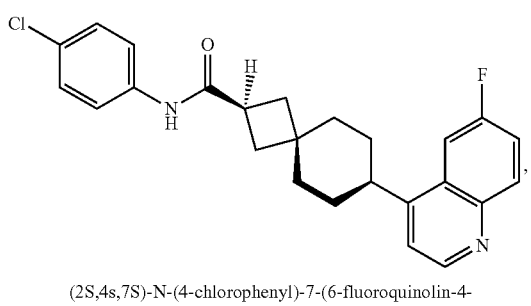

(2S,4s,7S)-N-(4-chlorophenyl)-7-(6-fluoroquinolin-4-yl)spiro[3.5]nonane-2-carboxamide

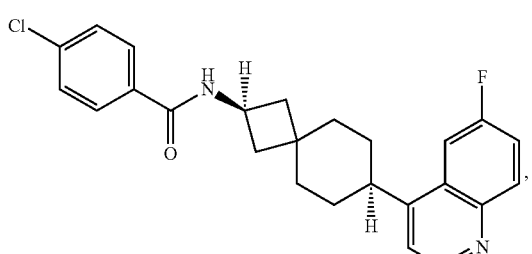

4-chloro-N-(7-(6-fluoroquinolin-4-yl)spiro[3.5]nonan-2-yl)benzamide

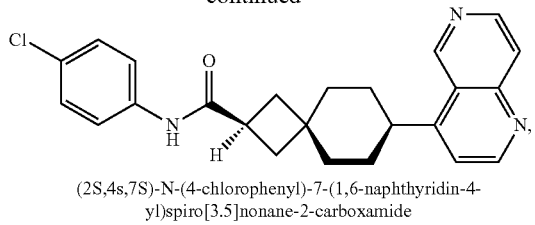

(2S,4s,7S)-N-(4-chlorophenyl)-7-(1,6-naphthyridin-4-yl)spiro[3.5]nonane-2-carboxamide

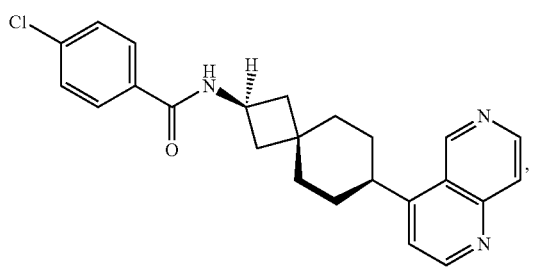

N-((2S,4s,7S)-7-(1,6-naphthyridin-4-yl)spiro[3.5]nonan-2-yl)-4-chlorobenzamide

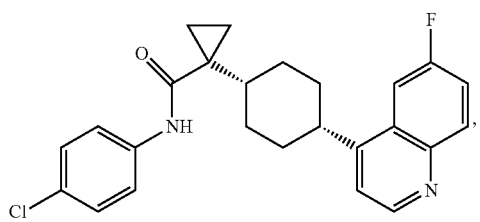

N-(4-chlorophenyl)-1-((1s,4s)-4-(6-fluoroquinolin-4-yl)cyclohexyl)cyclopropane-1-carboxamide

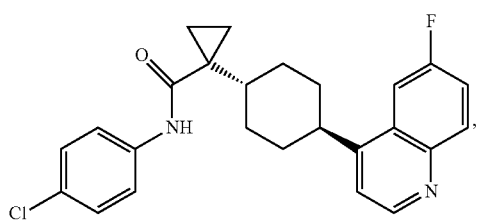

N-(4-chlorophenyl)-1-((1r,4r)-4-(6-fluoroquinolin-4-yl)cyclohexyl)cyclopropane-1-carboxamide

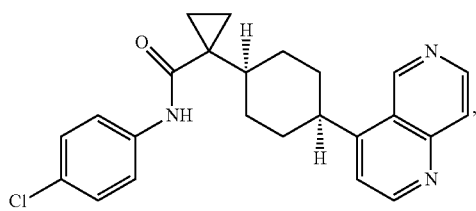

1-((1s,4s)-4-(1,6-naphthyridin-4-yl)cyclohexyl)-N-(4-chlorophenyl)cyclopropane-1-carboxamide

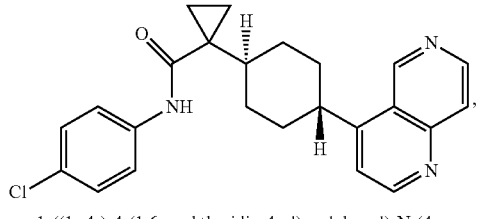

1-((1r,4r)-4-(1,6-naphthyridin-4-yl)cyclohexyl)-N-(4-chlorophenyl)cyclopropane-1-carboxamide

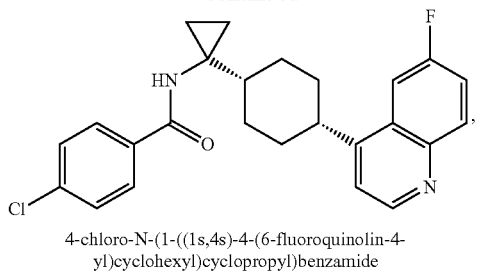

4-chloro-N-(1-((1s,4s)-4-(6-fluoroquinolin-4-yl)cyclohexyl)cyclopropyl)benzamide

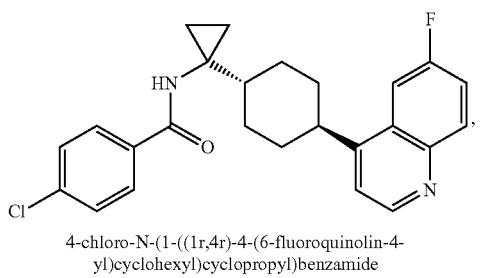

4-chloro-N-(1-((1r,4r)-4-(6-fluoroquinolin-4-yl)cyclohexyl)cyclopropyl)benzamide

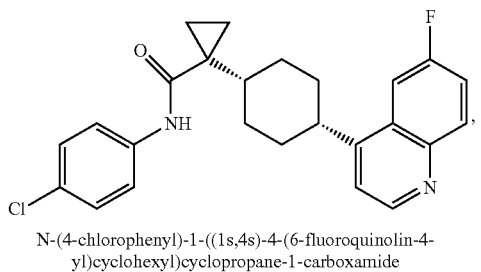

N-(4-chlorophenyl)-1-((1s,4s)-4-(6-fluoroquinolin-4-yl)cyclohexyl)cyclopropane-1-carboxamide

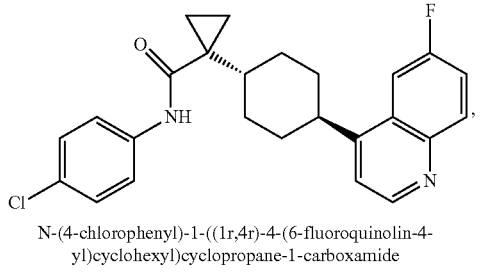

N-(4-chlorophenyl)-1-((1r,4r)-4-(6-fluoroquinolin-4-yl)cyclohexyl)cyclopropane-1-carboxamide

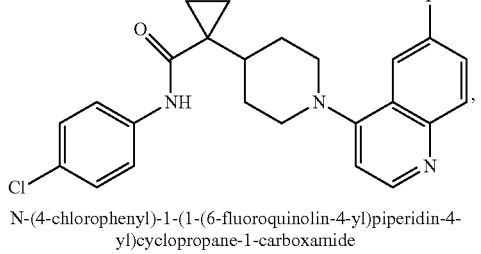

N-(4-chlorophenyl)-1-(1-(6-fluoroquinolin-4-yl)piperidin-4-yl)cyclopropane-1-carboxamide

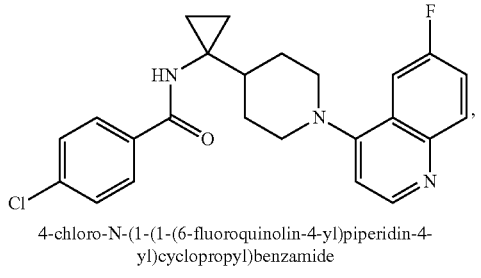

4-chloro-N-(1-(1-(6-fluoroquinolin-4-yl)piperidin-4-yl)cyclopropyl)benzamide

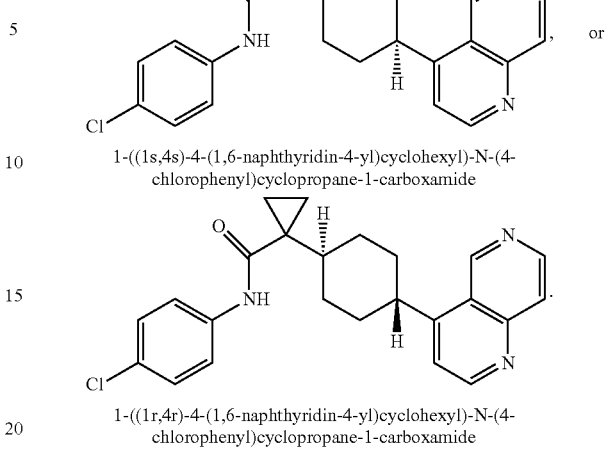

1-((1s,4s)-4-(1,6-naphthyridin-4-yl)cyclohexyl)-N-(4-chlorophenyl)cyclopropane-1-carboxamide 1-((1r,4r)-4-(1,6-naphthyridin-4-yl)cyclohexyl)-N-(4-chlorophenyl)cyclopropane-1-carboxamide A hydrogen atom in any position of a compound of Formula 1 or 2 may be replaced by a deuterium. In some embodiments, a compound of Formula 1 or 2 contains a deuterium atom or multiple deuterium atoms.

A pharmaceutical composition comprising a compound of Formula 1 or 2 may be adapted for oral, or parental, such as intravenous, intramuscular, topical, intraperitoneal, nasal, buccal, sublingual, or subcutaneous administration, or for administration via respiratory tract in the form of, for example, an aerosol or an air-suspended fine powder. The dosage of a compound of Formula 1 or 2 may vary depending on the route of administration, body weight, age, the type and condition of the disease being treated. A pharmaceutical composition provided herein may optionally comprise two or more compounds of the Formula 1 or 2 without an additional therapeutic agent, or may comprise an additional therapeutic agent (i.e., a therapeutic agent other than a compound provided herein). For example, the subject compounds can be used in combination with at least one other therapeutic agent. Therapeutic agents include, but are not limited to antibiotics, antiemetic agents, antidepressants, and antifungal agents, antiinflammatory agents, antiviral agents, and anticancer agents that are known in the art. The pharmaceutical composition may be used for the treatment of cancer, infectious diseases, and other IDO associated disorders in patients. The term "patient" herein means a mammal (e.g., a human or an animal). In some embodiments, the patient has cancer.

The pharmaceutical composition described herein can be prepared by combining a compound of Formula 1 or 2 with at least one pharmaceutical acceptable inert ingredient, such as a carrier, excipient, filler, lubricant, flavoring agent, buffer, etc., selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

An example, not as an attempt to limit the scope of the disclosure, of a useful composition for a dosage form containing about 20-1000 mg of 23-5A is shown in Table C below:

TABLE C

Example of dosage form of 23-5A

| Component | Amount (wt/wt) |
|---|---|
| Compound 1-5A | 30-70% |
| lubricant | 1-10% |
| diluent | 20-70% |
| disintegrant | 1-10% |

Some embodiments include a method of treating a disease or disorder associated with IDO comprising administering a therapeutically effective amount of a compound of Formula 1 or 2, or a pharmaceutical composition comprising a compound of Formula 1 or 2 to a patient in need thereof. The term a "therapeutically effective amount" herein refers to an amount of a subject compound, or a pharmaceutical composition containing a subject compound, sufficient to be effective in inhibiting IDO enzyme and thus providing a benefit in the treatment of cancer, infectious diseases and other IDO associated disorders, to delay or minimize symptoms associated with cancer, infectious diseases and other IDO associated disorders, or to ameliorate a disease or infection or cause thereof. The term "treatment" refers to causing a therapeutically beneficial effect, such as ameliorating existing symptoms, ameliorating the underlying causes of symptoms, postponing, preventing the further development of a disorder, or reducing the severity of symptoms that are otherwise expected to develop without treatment.

EXPERIMENTAL SECTION

Preparation of Compounds

The compounds of the disclosure can be made using procedures known in the art. The following reaction schemes show typical procedures, but those skilled in the art will recognize that other procedures can also be suitable for using to prepare these compounds. For examples in Formula I and II, wherein $R^1$ is not hydrogen, those skilled in the art will recognize that changes to the requisite reagents can be made at the appropriate steps in the synthetic methods outlined below. Reactions may involve monitoring for consumption of starting materials, and there are many methods for the monitoring, including but not limited to thin layer chromatography (TLC) and liquid chromatography mass spectrometry (LCMS). Those skilled in the art will recognize that any synthetic method specified in the examples shown below can be substituted by other non-limiting methods when suitable.

Some of the techniques, solvents and reagents can be referred to by their abbreviations as follows:
Acetonitrile: MeCN or ACN
Aqueous: aq.
Benzyl: Bn
1-[Bis(dimethylamino)methylene]-1H-1,2,3-triazolo[4,5-b]pyridinium 3-oxid hexafluorophosphate: HATU
[1,1'-Bis(diphenylphosphino)ferrocene]-dichloropalladium (II): Pd(dppf)Cl$_2$
Dimethylaminopyridine: DMAP
Dichloroethane: DCE
Dichloromethane: DCM
Diisobutylaluminum hydride: DIBAL or DIBAL-H
Diisopropylethylamine: DIPEA, DIEA or iPr$_2$NEt
Dimethylformamide: DMF
Dimethylsulfoxide: DMSO
Diphenylphosphoryl azide: DPPA
N-(3-Dimethylaminopropyl)-N'-ethylcarbodiimide hydrochloride: ECDI
Equivalents: equiv.
Ether or diethyl ether: Et$_2$O
Ethyl acetate: AcOEt or EtOAc
Ethyl magnesium bromide: EtMgBr
Gram(s): g
High performance liquid chromatography: HPLC
Inhibition: Inh.
Liquid chromatography mass spectrometry: LCMS
Lithium diisopropylamide: LDA
Lithium hexamethyldisilazide: LiHMDS
Methansulfonyl chloride: MeSO$_2$Cl
Methyl iodide: MeI
Methanol: MeOH
Microliter: ml
Micrometer: μm
Milligram: mg
Milliliter: mL
Millimole: mmol
n-Butyllithium: n-BuLi
Nuclear magnetic resonance spectroscopy: NMR
Palladium (II) acetate: Pd(OAc)$_2$
Palladium on activated carbon: Pd/C
Tris(dibenzylideneacetone)dipalladium(0): Pd$_2$(dba)$_3$
Palladium tetra-triphenylphosphine: Pd(PPh$_3$)$_4$
Petroleum ether: PE
N-Phenyl-bis(trifluoromethanesulfonimide): PhNTf$_2$
Retentional time: t$_R$
Room temperature (ambient, ~25° C.): rt or RT
Potassium tert-butoxide: t-BuOK
Potassium hexamethyldisilazide: KHMDS
Preparative HPLC: Prep-HPLC
Supercritical Fluid Chromatography: SFC
Sodium hexamethyldisilazide: NaHMDS
Temperature: temp.
Tetrahydrofuran: THF
Thin layer chromatography: TLC
p-Toluenesulfonic acid: TsOH
p-Toluenesulfonylmethyl isocyanide: TOSMIC
p-Toluenesulfonyl hydrazide: TsNHNH2
Triethylamine: Et$_3$N
Trifluoroacetic acid: TFA
2-Dicyclohexylphosphino-2',4',6'-triisopropylbiphenyl: X-phos In the synthetic schemes described below, unless otherwise indicated all temperatures are set forth in degrees Celsius and all parts and percentages are by weight. Reagents and solvents were purchased from commercial suppliers such as Aldrich Chemical Company and were used without further purification unless otherwise indicated. Tetrahydrofuran (THF) and N,N-dimethylformamide (DMF) were purchased from commercial sources in Sure Seal bottles and used as received.

The reactions set forth below were done generally under a positive pressure of argon or nitrogen at an ambient temperature (unless otherwise stated) in anhydrous solvents. Glassware was oven dried and/or heat dried. The reactions were assayed by TLC and/or analyzed by LC-MS and terminated as judged by the consumption of starting material. Analytical thin layer chromatography (TLC) was performed on glass plates pre-coated with silica gel 60 F254 0.25 mm plates (EM Science), and visualized with UV light (254 nm) and/or heating with commercial ethanolic phosphomolybdic acid. preparative thin layer chromatography (TLC) was performed on glass-plates pre-coated with silica gel 60 F254 0.5 mm plates (20×20 cm, from commercial sources) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Column chromatography was completed under positive pressure using 230-400 mesh silica gel.

$^1$H-NMR spectra and $^{13}$C-NMR were recorded on a Varian Mercury-VX400 instrument operating at 400 MHZ. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed.

Some of the typical synthetic methods are described in the examples shown below.

Method 1

Example 1: Synthesis of N-(4-chlorophenyl)-6-(6-fluoroquinolin-4-yl)spiro[2.5]octane-1-carboxamide (Compounds 1-10 and 1-11)

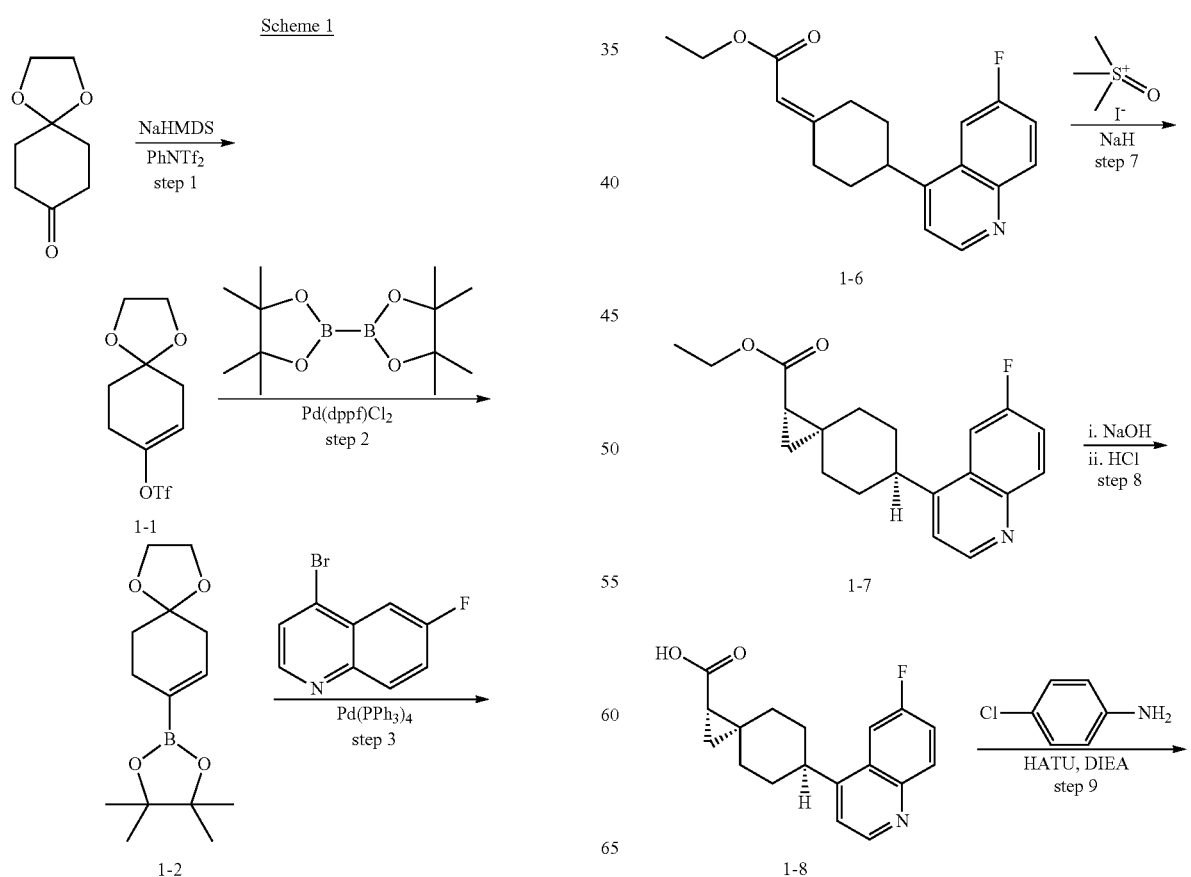

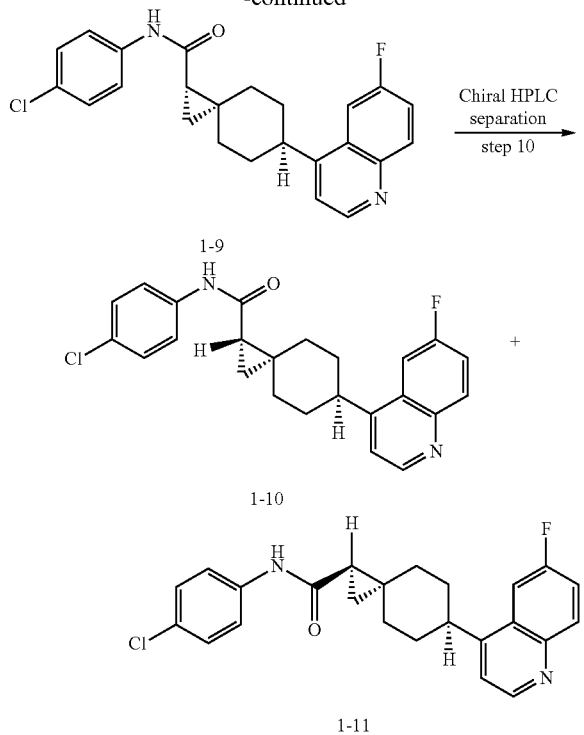

Step 1: Synthesis of 1,4-dioxaspiro[4.5]dec-7-en-8-yl trifluoromethanesulfonate

To a stirred solution of 62.5 mL of NaHMDS (2 M in THF, 125 mmol) in 400 mL of THF was added 15.0 g (96.2 mmol) of 1,4-dioxaspiro[4.5]decan-8-one dropwise at −78° C. under $N_2$ atmosphere. The reaction mixture was stirred at −78° C. for 30 minutes, then 44.6 g (125 mmol) of N-phenyl bis(trifluoromethanesulfoneimide) was added to the above mixture. After stirring at −78° C. for 1 h, the mixture was warmed to rt and stirred for additional 2 h. The reaction was quenched with slow addition of water, and extracted with three 100 mL portions of ethyl acetate. The combined organic extracts were washed with 100 mL of 5% $NaHCO_3$, 100 mL of 15% $NaHSO_4$, and 200 mL of brine, dried over anhydrous $Na_2SO_4$ and filtered. The filtrate was concentrated to afford a residue, which was purified by chromatography on silica gel column eluting with 3% ethyl acetate in petroleum ether to furnish compound 1-1. $^1$H NMR (400 MHz, $CDCl_3$) b 5.69 (t, J=5.4 Hz, 1H), 4.02-3.99 (m, 4H), 2.59-2.53 (m, 2H), 2.44-2.41 (m, 2H), 1.93 (t, J=8.8 Hz, 2H).

Step 2:

To a solution of 13.9 g (52.1 mmol) of 4,4,5,5-tetramethyl-2-(tetramethyl-1,3,2-dioxaborolan-2-yl)-1,3,2-dioxaborolane in 60 mL of dioxane was added 2.83 g (3.5 mmol) of $Pd(dppf)Cl_2.CH_2Cl_2$, 10.2 g (104.2 mmol) of KOAc, and 10.0 g (34.7 mmol) of 1-1 at room temperature under Ar atmosphere. The mixture was stirred at 100° C. overnight. The reaction mixture was cooled to room temperature and diluted with 50 mL of ethyl acetate. The mixture was filtered through Celite; the filter cake was washed with 30 mL of ethyl acetate. The filtrate was concentrated under reduced pressure. The residue was purified by silica gel column chromatography eluting with 25% ethyl acetate in petroleum ether to afford compound 1-2. LC-MS: m/e=267 [M+H]$^+$.

Step 3:

To a stirred solution of 3.92 g (17.4 mmol) of 4-bromo-6-fluoroquinoline in 65 mL of 1,4-dioxane was added 7.2 g (52.2 mmol) of $K_2CO_3$, 1.0 g (0.87 mmol) of $Pd(PPh_3)_4$, and 6.0 g (22.6 mmol) of compound 1-2 at room temperature under Ar atmosphere. After addition of 13 mL of water, the reaction mixture was stirred at 100° C. overnight under Ar atmosphere, and then cooled to room temperature. The mixture was concentrated under reduced pressure and the residue was diluted with 40 mL of ethyl acetate and filtered through Celite. The filter cake was washed with 30 mL of ethyl acetate, and the filtrate was concentrated to give a residue, which was purified by silica gel column chromatography eluting with 16% ethyl acetate in petroleum ether to afford compound 1-3. LC-MS: m/e=286 [M+H]$^+$.

Step 4:

To a stirred solution of 4.0 g (14.0 mmol) of compound 1-3 in 60 mL of i-PrOH was added 2.0 g of wet 10% Pd/C. The mixture was stirred at room temperature under $H_2$ atmosphere for 4 h and filtered through a short pad of Celite. The filter cake was washed with 50 mL of ethyl acetate. The combined filtrates were concentrated under reduced pressure to afford compound 1-4. LC-MS: m/e=288 [M+H]$^+$.

Step 5:

To a stirred solution of 4.5 g (15.7 mmol) of compound 1-4 in 70 mL of acetone was added 15 mL of 4 N HCl. The mixture was stirred at 45° C. overnight and basified to pH 9 with 6 N NaOH. The mixture was diluted with 50 mL of $H_2O$ and extracted with three 20 mL portions of ethyl acetate. The combined organic extracts were dried over anhydrous $Na_2SO_4$ and filtered. The filtrate was concentrated to give a residue, which was purified by silica gel column chromatography eluting with 16% ethyl acetate in petroleum ether to afford compound 1-5. LC-MS: m/e=244 [M+H]$^+$.

Step 6:

To a stirred solution of 2.8 g (12.4 mmol) of ethyl-2-(diethoxyphosphoryl) acetate in 90 mL of $CH_2Cl_2$ was added 1.4 g (12.4 mmol) of t-BuOK at −70° C. The mixture was stirred at −70° C. for 1 h. After addition of 2.0 g (8.2 mmol) of compound 1-5, the mixture was stirred at room temperature overnight, then quenched with ice water, separated to two layers. The aqueous layer was extracted with two 20 mL portions of $CH_2Cl_2$. The combined organic extracts were dried over anhydrous $Na_2SO_4$ and filtered. The filtrate was concentrated under vacuum to generate a residue, which was purified by silica gel column chromatography eluting with 16% ethyl acetate in petroleum ether to afford compound 1-6. LC-MS: m/e=314 [M+H]$^+$.

Step 7:

To a solution of 0.28 g (1.3 mmol) of trimethanesulfinylidene iodane in 13 mL of DMF was added 0.077 g (1.9 mmol) of NaH (60% in mineral oil) at room temperature. The mixture was stirred at room temperature under Ar atmosphere for 3 h. After addition of a solution of 0.2 g (0.6 mmol) of compound 1-6 in 1 mL of DMF dropwise, the mixture was stirred at room temperature overnight, quenched with 15 mL of water, and extracted with three 15 mL portions of ethyl acetate. The combined organic extracts were washed with brine, dried over $Na_2SO_4$, and concentrated under vacuum. The residue was purified by silica gel column chromatography eluting with 0% to 25% gradient of ethyl acetate in petroleum ether to afford crude product 1-7. LC-MS: m/e=328 [M+H]$^+$.

Step 8:

To a stirred solution of 0.2 g of crude 1-7 in EtOH—$H_2O$ (4:1, 20 mL) was added 0.12 g (3.0 mmol) of NaOH at room temperature. The mixture was stirred at 50° C. overnight and cooled to room temperature. The mixture was adjusted to pH 6 with 2 N HCl, concentrated under vacuum to generate a residue, which was extracted with three 10 mL portions of ethyl acetate. The combined organic extracts were dried over $Na_2SO_4$ and filtered. The filtrate was concentrated under vacuum to obtain crude product 1-8, which was used in the next step without further purification. LC-MS: m/e=300 $[M+H]^+$.

Step 9:

To a stirred solution of 0.15 g (0.5 mmol) of crude 1-8 and 0.077 g (0.6 mmol) of 4-chloroaniline in 1 mL of DMF was added 0.13 g (1.0 mmol) of DIEA and 0.23 g (0.6 mmol) of HATU at room temperature. The mixture was stirred at room temperature overnight, and filtered. The filter cake was washed with MeOH. The filtrate was purified by Prep-HPLC [SHIMADZU: Column, XBridge Prep $C_{18}$ OBD Column, 5 μm, 19*150 mm; Mobile phase, water (10 mmol/L $NH_4HCO_3$) and ACN (55% Phase B up to 69% in 8 min); Detector, UV] to give the desired product 1-9. LC-MS: m/e=409 $[M+H]^+$.

Step 10:

Compound 1-9 (0.035 g) was resolved by Chiral-HPLC separation (Column: CHIRAL ATR cellulose-SB, 2*25 cm, 5 μm; Mobile phase A: Hexane; Mobile phase B: EtOH; flow rate: 20 mL/min; Gradient: Isograd 10% phase B in 15 min; 220/254 nm, UV) to yield 1-10 (Peak 1) and 1-11 (Peak 2). LC-MS for 1-10: m/e=409 $[M+H]^+$. LC-MS for 1-11: m/e=409 $[M+H]^+$.

The following analogs listed in Table 1 were prepared from racemic intermediate 1-8 by the procedure described in Method 1, step 9.

TABLE 1

Compound structures, their identification numbers and LCMS data

| Compound Structure | LCMS $[M + H]^+$ |
|---|---|
| 1-12 | 393 |
| 1-13 | 415 |
| 1-14 | 389 |
| 1-15 | 409 |
| 1-16 | 393 |
| 1-17 | 443 |
| 1-18 | 382 |

TABLE 1-continued

Compound structures, their identification numbers and LCMS data

| Compound Structure | LCMS [M + H]+ |
|---|---|
| 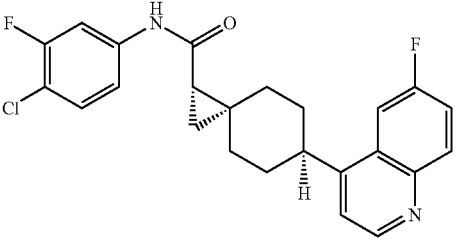 1-19 | 427 |
| 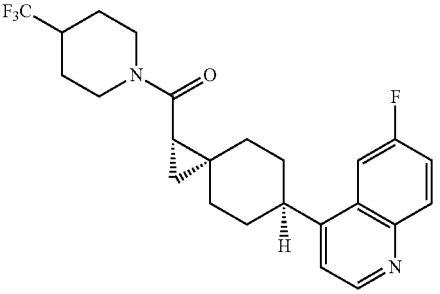 1-20 | 435 |
| 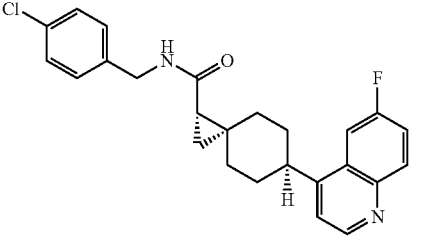 1-21 | 423 |
| 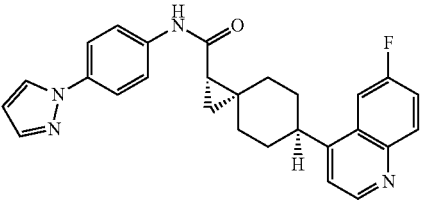 1-22 | 441 |
| 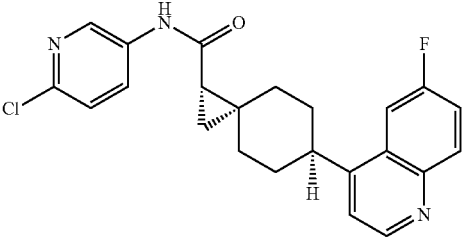 1-23 | 410 |

Method 2

Example 2: Synthesis of N-(4-cyanophenyl)-6-(6-fluoroquinolin-4-yl)spiro[2.5]octane-1-carboxamide (Compound 2-1)

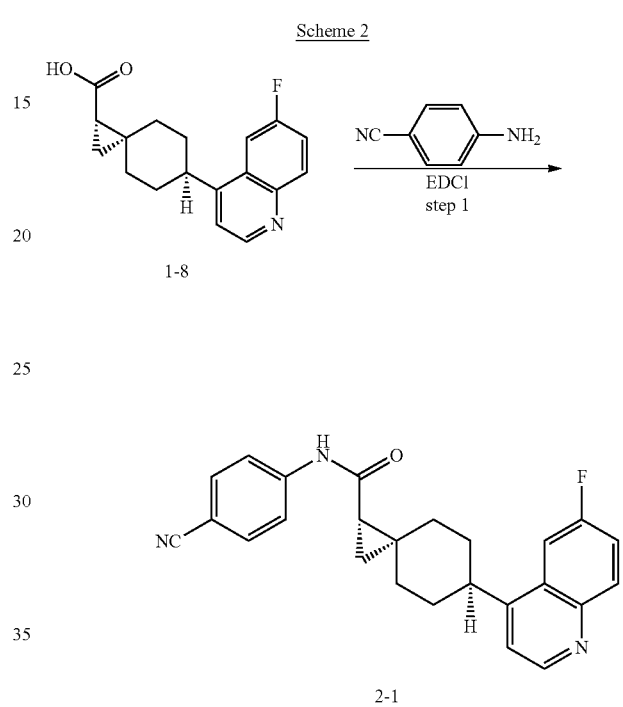

Scheme 2

Step 1:

To a stirred mixture of 80 mg (0.27 mmol) of intermediate 1-8 in 3 mL of pyridine were added 67 mg (0.35 mmol) of EDCI and 63 mg (0.53 mmol) of 4-aminobenzonitril at RT. The mixture was stirred at RT for 3 h, quenched with 10 mL of water, and extracted with three 15 mL portions of ethyl acetate. The combined organic extracts were washed with three 10 mL portions of brine and dried over anhydrous $Na_2SO_4$. After filtration, the filtrate was concentrated under reduced pressure to afford a residue, which was purified by Prep-HPLC with the following conditions (SHIMADZU: Column, XBridge Prep C18 OBD Column, 19×150 mm 5 um; mobile phase, Water (10 mM $NH_4HCO_3$) and CAN (52% PhaseB up to 65% in 8 min); Detector, UV. Flow rate: 20 mL/min) to afford compound 2-1. LC-MS: m/e=400 [M+H]+.

The following analogs listed in Table 2 were prepared from racemic intermediate 1-8 by the procedure described in Method 2, step 1.

TABLE 2

Compound structures, their identification numbers and LCMS data.

| Compound Structure | LCMS [M + H]+ |
|---|---|
| 2-2 | 409 |
| 2-3 | 410 |
| 2-4 | 443 |
| 2-5 | 427 |
| 2-6 | 394 |

Method 3

Example 3: Synthesis of 6-(6-fluoroquinolin-4-yl)-N-(5-(trifluoromethyl)pyridin-2-yl)spiro[2.5]octane-1-carboxamide (Compound 3-2)

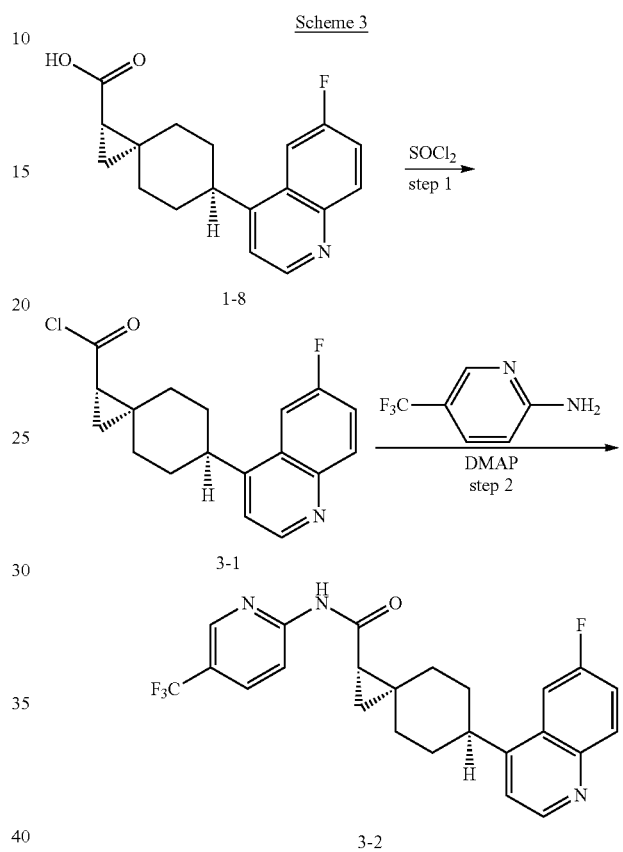

Step 1:

To a solution of 25 mL of SOCl$_2$ was added 500 mg (1.67 mmol) of compound 1-8 in several portions at 0° C. The reaction mixture was stirred for 2 h at 0° C. under nitrogen atmosphere. The resulting mixture was concentrated under vacuum to afford intermediate 3-1, which was used in the next step directly without further purification.

Step 2:

To a stirred solution of 153 mg (0.94 mmol) of 5-(trifluoromethyl)pyridin-2-amine in 8 mL of DCM were added 305 mg (2.36 mmol) of DIEA, 6.0 mg (0.049 mmol) of DMAP, and 150 mg of the above 3-1 in 2 mL of DCM at 0° C. The reaction mixture was stirred at RT overnight, then diluted with 10 mL water, and extracted with three 15 mL portions of DCM. The combined organic layers were washed with brine and dried over anhydrous Na$_2$SO$_4$. It was filtered and the filtrate was concentrated to give a residue, which was purified by Prep-HPLC (Column, XBridge Prep OBD C18 Column, 30×150 mm 5 μm; mobile phase, Water (10 mM NH$_4$HCO$_3$) and ACN (52% Phase B up to 70% in 8 min); Detector, UV 254 nm) to compound 3-2. LC MS: m/e=444 [M+H]+.

Compound 3-3 in Table 3 was prepared from acid 1-8 similarly using the above procedures.

TABLE 3

Compound structure, identification number and LCMS data

| Compound Structure | LCMS [M + H]+ |
|---|---|
| 3-2 | 444 |
| 3-3 | 401 |

Method 4

Example 4: Alternative synthesis of N-(4-chlorophenyl)-6-(6-fluoroquinolin-4-yl)spiro[2.5]octane-1-carboxamide (Compound 1-10)

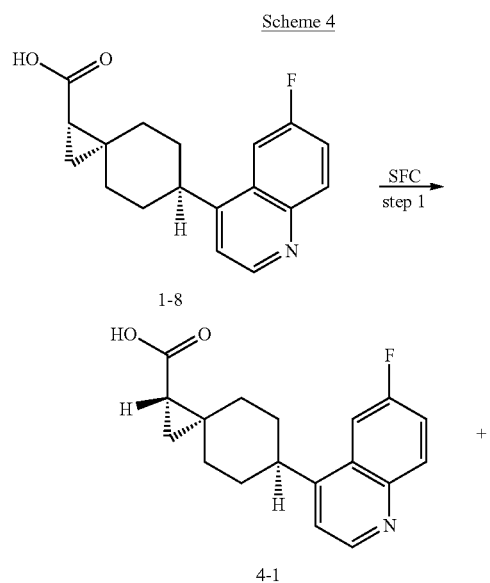

Scheme 4

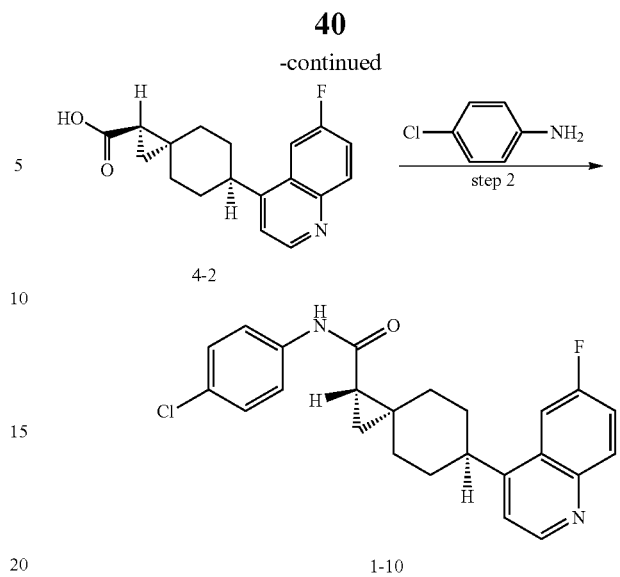

Step 1

Compound 1-8 (10 g) was separated by Chiral-SFC (Column: CHIRALPAK AD-H SFC, 5*25 cm, 5 μm; Mobile Phase A: C02:65%, Mobile Phase B: MeOH—Preparative: 35%; Flow rate: 160 mL/min; 220 nm) to give enantiomer 4-1 (4.3 g, Peak 1) and enantiomer 4-2 (4.2 g, Peak 2).

Step 2:

The (S)-enantiomer 4-1 was converted to compound 1-10 by the similar procedure described in Method 1, step 9. LC-MS: m/e=409 [M+H]+.

The following analogs shown in Table 4 were prepared from enantiomer 4-1 similarly.

TABLE 4

Compound structures, their identification numbers and LCMS data

| Compound Structure | LCMS [M + F]+ |
|---|---|
| 4-4 | 453 |
| 4-5 | 501 |

TABLE 4-continued
Compound structures, their identification numbers and LCMS data
| Compound Structure | LCMS [M + F]+ |
|---|---|
| 4-6 | 400 |
| 4-7 | 427 |
| 4-8 | 471, 473 |
| 4-9 | 519 |
Method 5
Example 5: Synthesis of N-(4-chlorophenyl)-6-(6-fluoroquinolin-4-yl)spiro[2.5]octane-1-carboxamide (Compound 5-4)
Scheme 5
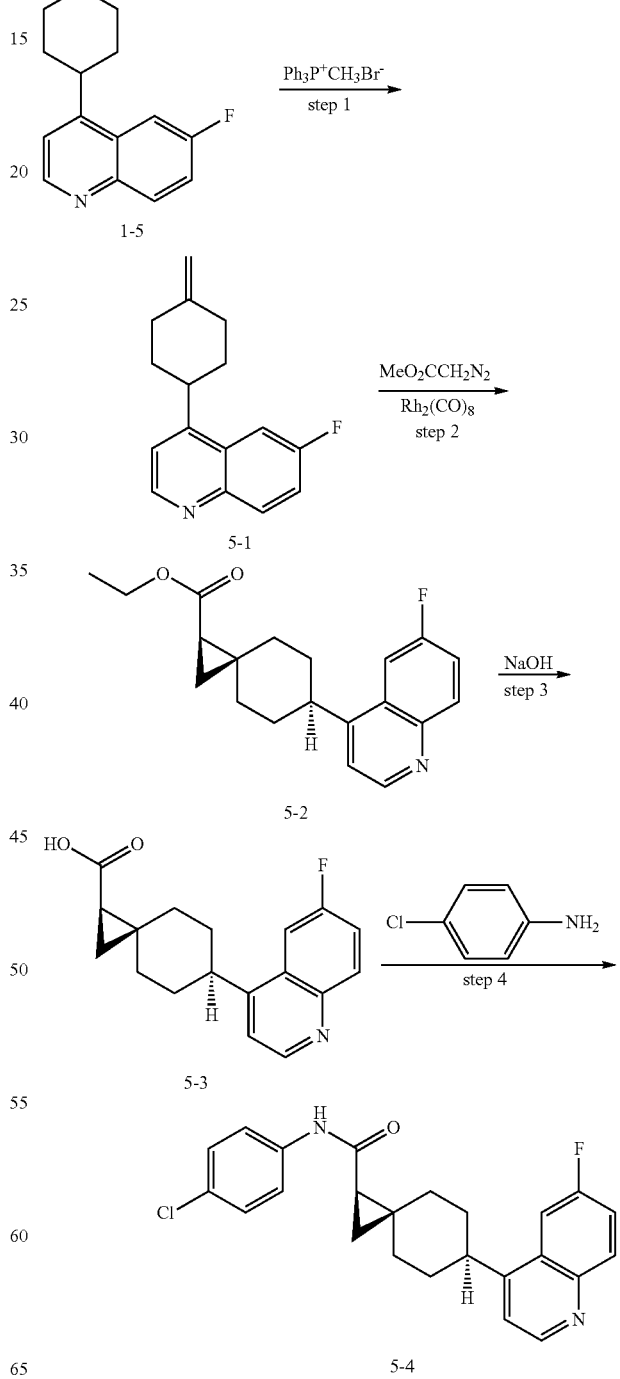

Step 1

To a stirred solution of 3.20 g (9.04 mmol) of methyltriphenylphosphonium bromide in 40 mL of THF was added 3.75 mL (2.5 M in n-Hexane, 9.37 mmol) of n-BuLi dropwise at −5° C. under $N_2$ atmosphere. The mixture was stirred at 0° C. for 1 h under $N_2$ atmosphere. To the above mixture was added a solution of 2.0 g (8.22 mmol) of compound 1-5 in 10 mL of THF dropwise over 30 min at 0° C. The mixture was stirred at RT overnight, then quenched with 150 ml of aqueous $NH_4Cl$ at 0° C., and extracted with three 100 mL portions of ethyl acetate. The combined organic extracts were washed with 200 mL of brine and dried over anhydrous $Na_2SO_4$. After filtration, the filtrate was concentrated to afford a residue, which was purified by silica gel column eluting with 0 to 20% gradient of ethyl acetate in petroleum ether to afford compound 5-1. LC-MS: m/e=242 [M+H]$^+$.

Step 2:

To a stirred solution 530 mg (2.20 mmol) of compound 5-1 and 971 mg (2.20 mmol) of $Rh_2(OAc)_4$ in 10 mL of DCM was added 1003 mg (8.79 mmol) of ethyl 2-diazoacetate in 20 mL of DCM dropwise slowly over 15 min under argon atmosphere. The mixture was stirred at RT for 2 days and then filtered. The filtrate was concentrated under reduced pressure to afford a residue, which was purified by Prep-TLC (PE/EtOAc 3:1) to afford compound 5-2. LC-MS: m/e=328 [M+H]$^+$.

Step 3:

Compound 5-2 was converted to compound 5-3 by the procedure described in Method 1, step 8. LC-MS: m/e=300 [M+H]$^+$.

Step 4:

Compound 5-3 was converted to compound 5-4 by the procedure described in Method 2, step 1. LCMS: m/e=409 [M+H]$^+$.

Method 6

Example 6: Synthesis of N-(4-chlorophenyl)-6-(1,6-naphthyridin-4-yl)spiro[2.5]octane-1-carboxamide (Compound 6-9)

Scheme 6

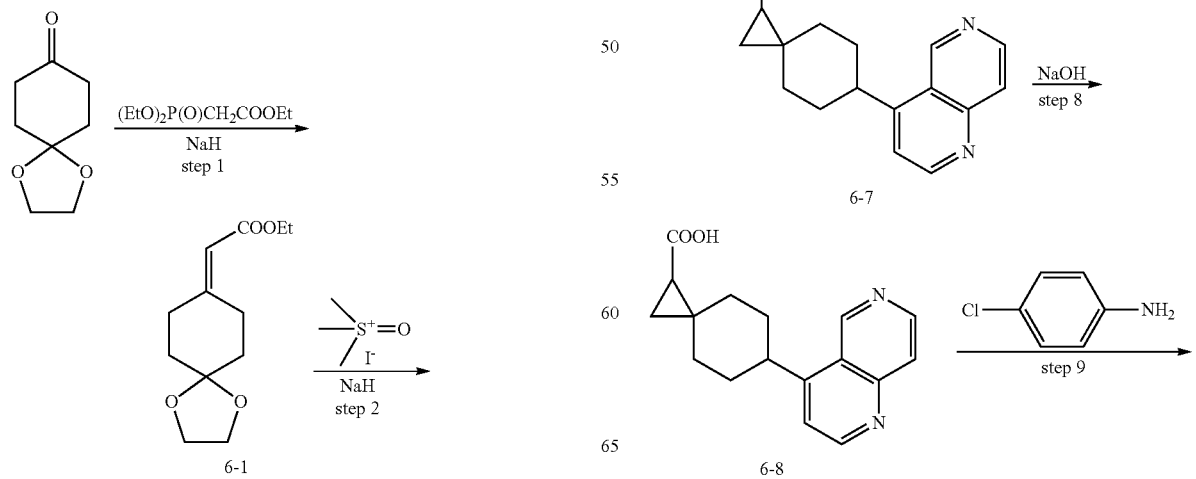

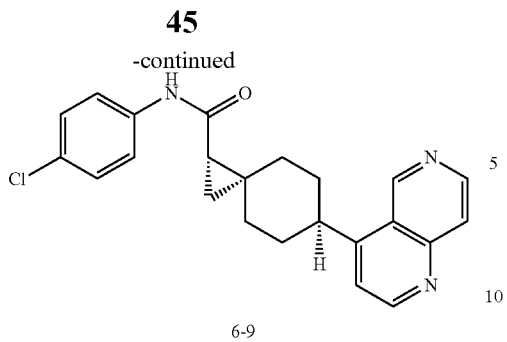

6-9

Step 1

To a stirred solution of 10.8 g (48.2 mmol) of ethyl 2-(diethoxyphosphoryl) acetate in 130 mL of THF was added 1.90 g (79.1 mmol) of NaH (60% in coal oil) at 0° C. under argon atmosphere. The mixture was stirred at 0° C. for 1 h. After addition of a solution of 5.0 g (32.0 mmol) of 1,4-dioxaspiro[4.5]decan-8-one in THF dropwise at 0° C., the mixture was stirred at 0° C. for 30 min and at RT for 5 h, and then quenched with 150 mL NH$_4$Cl aqueous solution. The mixture was extracted with three 150 mL portions of ethyl acetate and washed with 150 mL of brine. The combined organic extracts were dried over anhydrous Na$_2$SO$_4$ and filtered. The filtrate was concentrated to give a residue, which was purified by silica gel column chromatography eluting with 0 to 10% gradient of ethyl acetate in petroleum ether to afford compound 6-1. LC-MS: m/e=227 [M+H]$^+$.

Step 2:

Compound 6-2 was prepared from 6-1 using the procedure described in Method 1, step 7. LC-MS: m/e=241 [M+H]$^+$.

Step 3:

Compound 6-3 was prepared from 6-2 using the procedure described in Method 1, step 5. LC-MS: m/e=197 [M+H]$^+$.

Step 4:

Compound 6-4 was prepared from 6-3 using the procedure described in Method 1, step 1. LC-MS: m/e=329 [M+H]$^+$.

Step 5:

Compound 6-5 was prepared from 6-4 using the procedure described in Method 1, step 2. LC-MS: m/e=307 [M+H]$^+$.

Step 6:

Compound 6-6 was prepared from 6-5 using the procedure described in Method 1, step 3. LC-MS: m/e=309 [M+H]$^+$.

Step 7:

Compound 6-7 was prepared from 6-6 using the procedure described in Method 1, step 4. LC-MS: m/e=311 [M+H]$^+$.

Step 8:

Compound 6-8 was prepared from 6-7 using the procedure described in Method 1, step 8. LC-MS: m/e=283 [M+H]$^+$.

Step 9:

Compound 6-9 was prepared from 6-8 using the procedure described in Method 1, step 9. LC-MS: m/e=392 [M+H]$^+$.

Method 7

Example 7: Synthesis of N-(4-chlorophenyl)-6-(1,6-naphthyridin-4-yl)spiro[2.5]octane-1-carboxamide (Compounds 7-6 and 7-7)

Scheme 7

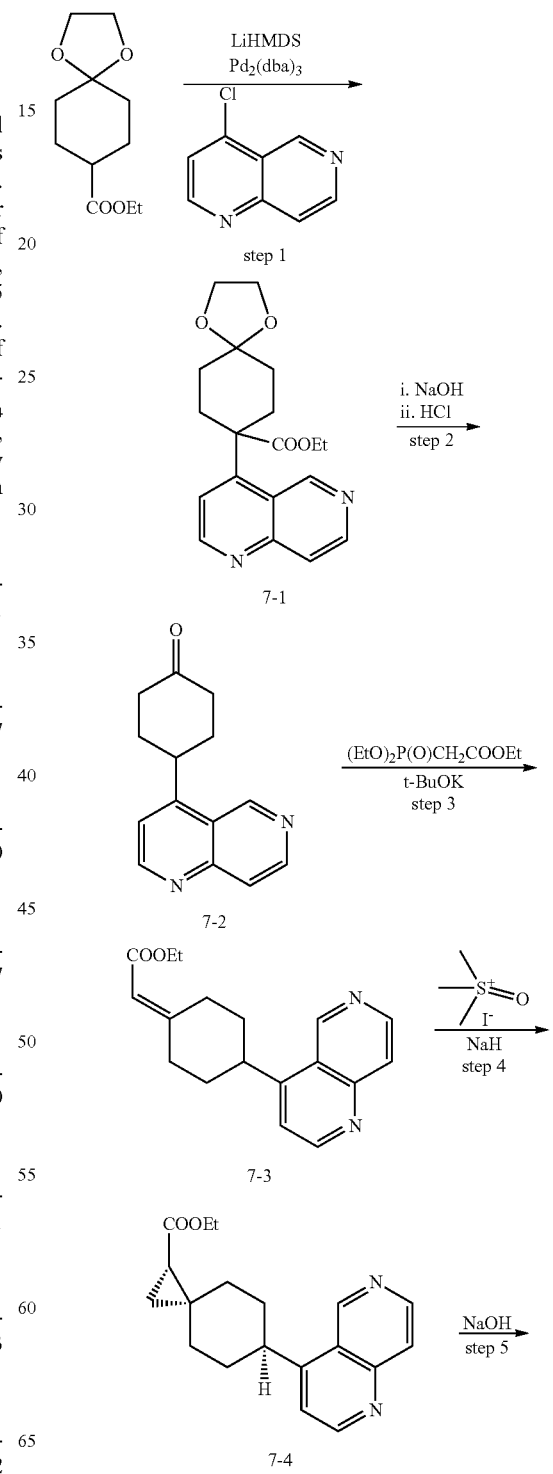

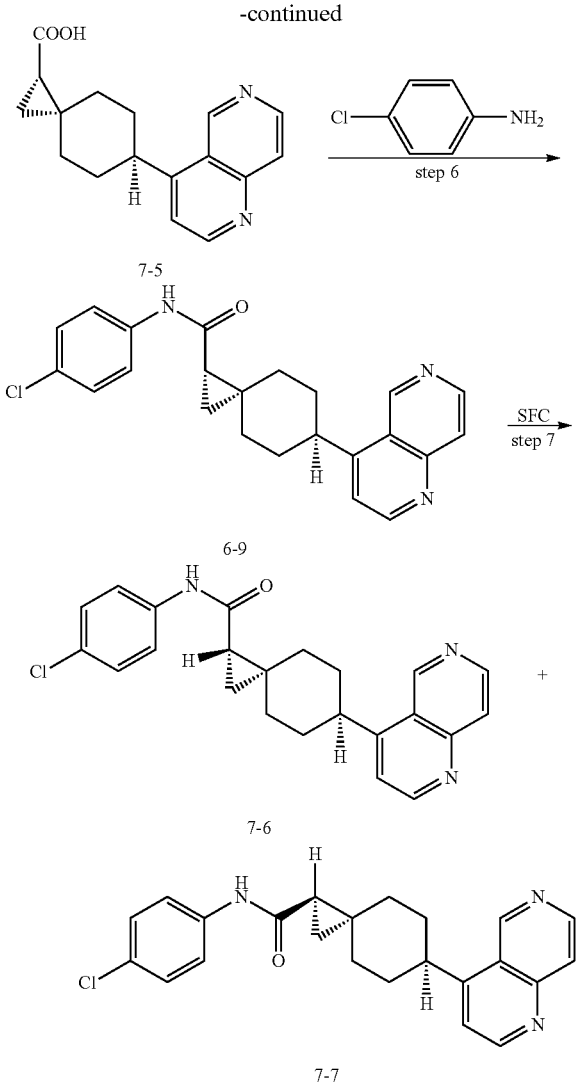

Step 1

To a solution of 0.353 g (1.22 mmol) of t-Bu₃P-HBF₄ in 20 mL of toluene was added 0.633 g (2.88 mmol) of Pd₂(dba)₃ at rt and stirred for 20 min under Ar atmosphere.

To a stirred solution of 10.0 g (60.8 mmol) of 4-chloro-1,6-naphthyridine and 15.6 g (72.9 mmol) of ethyl 1,4-dioxaspiro[4.5]decane-8-carboxylate in 50 mL of toluene were added 122 mL (122 mmol) of LiHMDS (1 M in THF) at RT and followed by the above catalyst dropwise under argon atmosphere. The mixture was stirred at RT overnight and quenched by addition of 50 mL of ice water. It was extracted with three 50 mL portions of ethyl acetate, the combined organic extracts were washed with 100 mL of brine and dried over anhydrous Na₂SO₄. After filtration, the filtrate was concentrated to afford a residue, which was purified by chromatography on silica gel column eluting with 0 to 50% gradient of ethyl acetate in petroleum ether to afford compound 7-1. LC-MS: m/e=343 [M+H]⁺.

Step 2:

To a stirred solution of 5.0 g (14.6 mmol) of compound 7-1 in 60 mL of EtOH—H₂O (2:1) was added 3.5 g (87.7 mmol) of NaOH at RT. The mixture was stirred at 70° C. for 4 h under N₂ atmosphere and then cooled to RT. It was adjusted to pH 2 with 6 N HCl and stirred at 70° C. for additional 4 h under N₂ atmosphere. It was neutralized to pH 8 with saturated Na₂CO₃ (aq.) and extracted with three 50 mL portions of ethyl acetate. The combined organic extracts were washed with 100 mL of brine and dried over anhydrous Na₂SO₄. After filtration, the filtrate was concentrated to afford a residue, which was purified by chromatography on silica gel column eluting with 0 to 25% gradient of ethyl acetate in petroleum ether to afford compound 7-2. LC-MS: m/e=227 [M+H]⁺.

Step 3:

Compound 7-3 was prepared from intermediate 7-2 by the procedure described in Method 1, step 1. LC-MS: m/e=297 [M+H]⁺.

Step 4:

Compound 7-4 was prepared from intermediate 7-3 by the procedure described in Method 1, step 7. LC-MS: m/e=311 [M+H]⁺.

Step 5:

Compound 7-5 was prepared from intermediate 7-4 by the procedure described in Method 1, step 8. LC-MS: m/e=283 [M+H]⁺.

Step 6:

Compound 6-9 was prepared from intermediate 7-5 by the procedure described in Method 1, step 9. LC-MS: m/e=392 [M+H]⁺.

Step 7:

The racemic compound 6-9 was separated by Chiral-HPLC (Column: CHIRALPAK IG-03, 2.0 cm I.D*25 cm, 5 µm; Mobile Phase A: CO₂:50, Mobile Phase B: MeOH: DCM=1:1:50; Flow rate: 40 mL/min; 254 nm) to yield compound 7-6 (Peak 1), LC-MS: m/e=392 [M+H]⁺ and compound 7-7 (Peak 2) LC-MS: m/e=392 [M+H]⁺.

The following analogs shown in Table 5 were prepared from intermediate 6-5 using the reaction sequence described in Method 6, step 6 through step 9. General scheme is depicted in Scheme 8.

Method 8

Scheme 8

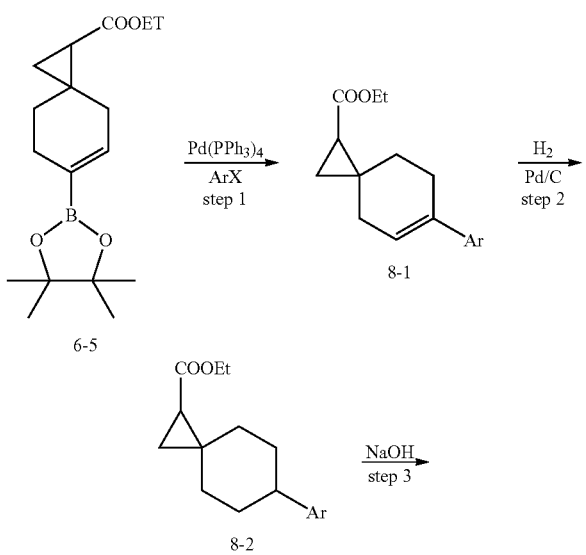

49
-continued
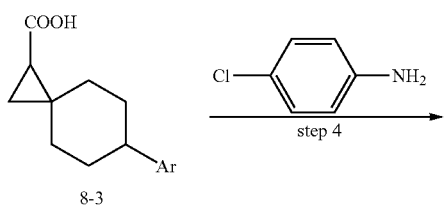
50
-continued
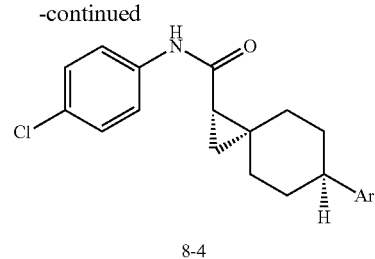
TABLE 5
Compound structures, their identification numbers and LCMS data
| ArX Structure | Example Structure | LCMS [M + H]+ |
|---|---|---|
| 4-bromo-6-chloroquinoline | 8-4A | 425 |
| 4-bromoquinoline-6-carbonitrile | 8-4B | 416 |
| 4-bromo-6,7-dimethoxyquinoline | 8-4C | 451 |

TABLE 5-continued
Compound structures, their identification numbers and LCMS data
| ArX Structure | Example Structure | LCMS [M + H]+ |
|---|---|---|
| 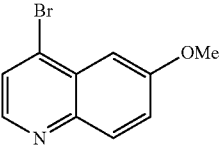 [SMILES: COc1ccc2nccc(Br)c2c1] | 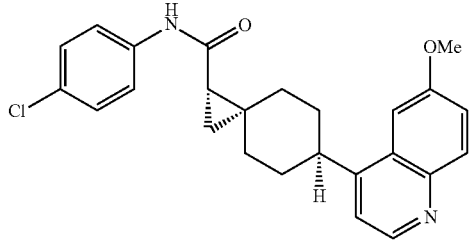<br>8-4D | 421 |
| 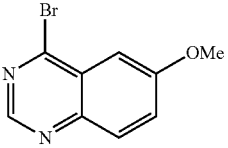 [SMILES: COc1ccc2ncnc(Br)c2c1] | 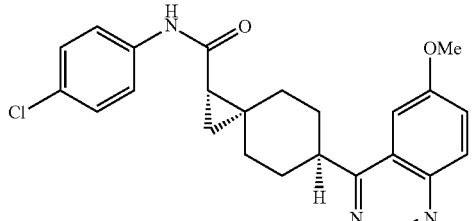<br>8-4E | 422 |
| 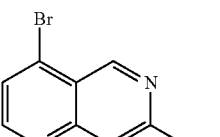 | 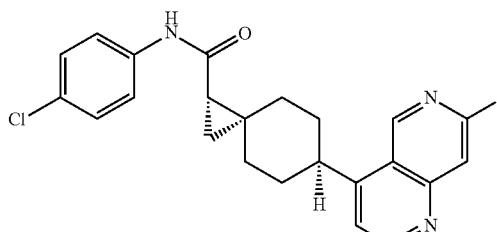<br>8-4F | 422 |
| 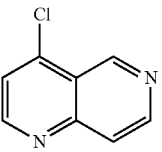 | 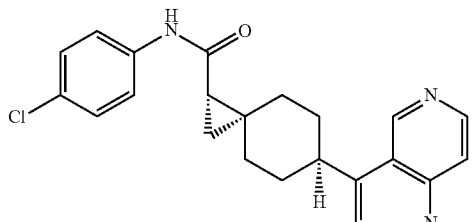<br>6-9 | 392 |

Method 9

Example 9: Synthesis of 4-chloro-N-(6-(6-fluoro-quinolin-4-yl)spiro[2.5]octan-1-yl)benzamide

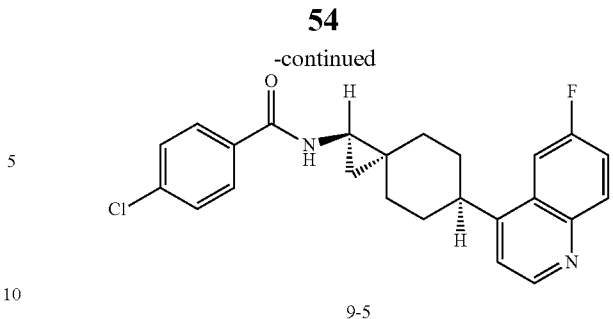

9-5

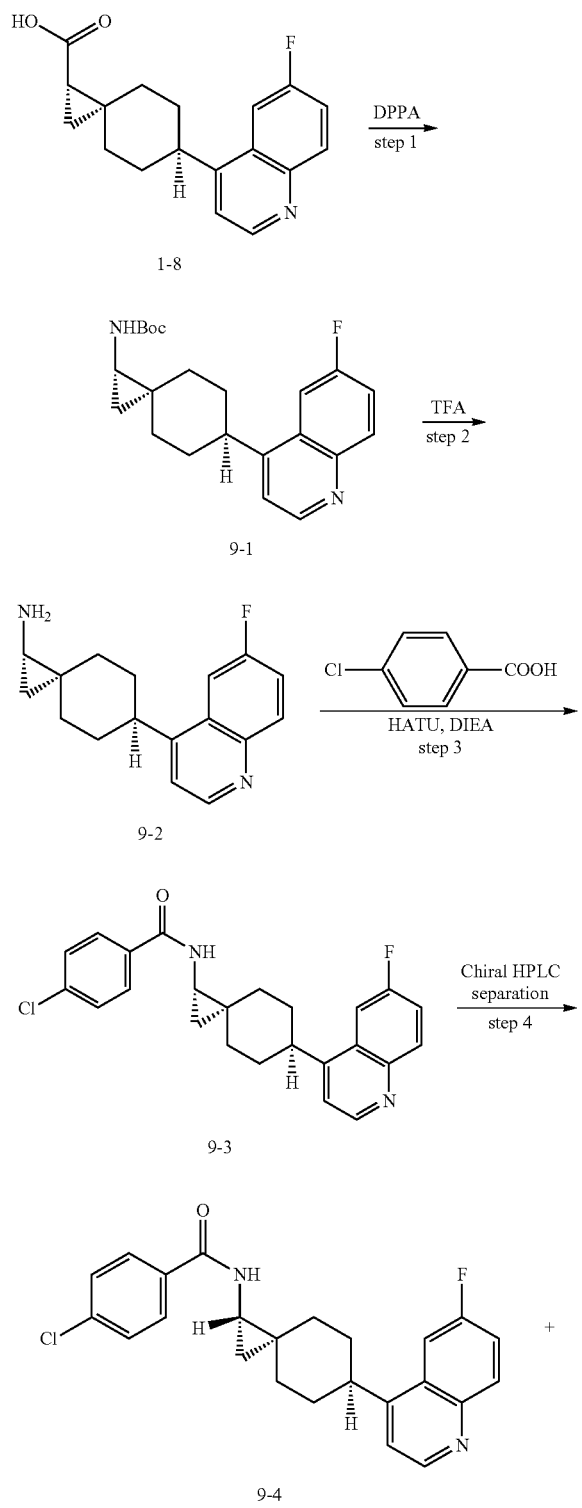

Step 1

To a stirred solution of 0.16 g (0.54 mmol) of compound 1-8 in 15 mL of toluene/t-BuOH (8:1) were added 0.108 g (1.07 mmol) of Et$_3$N, and 0.22 g (0.80 mmol) of diphenylphosphonic azide. The mixture was heated at reflux for 4 h under Ar atmosphere, concentrated under reduced pressure, then quenched with 10 mL of water, and extracted with three 15 mL portions of ethyl acetate. The combined organic extracts were washed with brine and dried over Na$_2$SO$_4$. After filtration, the filtrate was concentrated to afford a crude, which was purified by chromatography on silica gel column eluting with 0% to 35% gradient of ethyl acetate in petroleum ether to afford compound 9-1. LC-MS: m/e=371 [M+H]$^+$.

Step 2:

To a stirred solution of 0.03 g (0.08 mmol) of compound 9-1 in 3 mL of CH$_2$Cl$_2$ was added 0.32 g (2.8 mmol) of CF$_3$COOH at RT. The mixture was stirred at room temperature for 2 h and concentrated under vacuum to obtain compound 9-2, which was used in the next step without further purification. LC-MS: m/e=271 [M+H]$^+$.

Step 3:

To a stirred solution of 0.03 g of compound 9-2 and 0.03 g (0.19 mmol) of 4-chlorobenzoic acid in 3 mL of DMF were added 0.04 g (0.31 mmol) of DIEA and 0.04 g (0.11 mmol) of HATU at room temperature. The mixture was stirred at room temperature overnight and filtered, and the filter cake was washed with ACN. The filtrate was purified by Prep-HPLC [SHIMADZU: Column, XBridge Prep C18 OBD Column, 5 μm, 19*150 mm; mobile phase, A: water (10 mmol/L NH$_4$HCO$_3$+0.1% NH$_3$.H$_2$O) and B: ACN, (Gradient: Phase B 43% to 70% in 8 min.); Flow rate: 20 mL/min, Detector, 254 nm UV] to give 9-3. LC-MS: m/e=409 [M+H]$^+$.

Step 4:

Compound 9-3 was resolved by chiral HPLC separation (Column: Chiralpak IA-3, 3.0*100 mm, 3.0 μm; Mobile phase: A: CO$_2$, B: 20 mmol/L NH$_3$ in MeOH, gradient: 90:10 to 50:50 (A:B) over 3.0 min., 50:50 (A:B) for 3.0 min.; UV detection: 220 nm.) to yield 9-4 (Peak 1) and 9-5 (Peak 2).

The following racemic analogs shown in Table 6 were prepared from intermediate 9-3 by coupling with appropriate carboxylic acid, as described in Method 9, step 3

TABLE 6

Compound structures, their identification numbers and LCMS data

| Compound Structure | LCMS [M + H]+ |
|---|---|
| 9-6 | 389 |
| 9-7 | 400 |
| 9-8 | 443 |
| 9-9 | 459 |

Method 10

Example 10: Synthesis of N-(4-chlorophenyl)-1-fluoro-6-(6-fluoroquinolin-4-yl)spiro[2.5]octane-1-carboxamide (Compound 10-4)

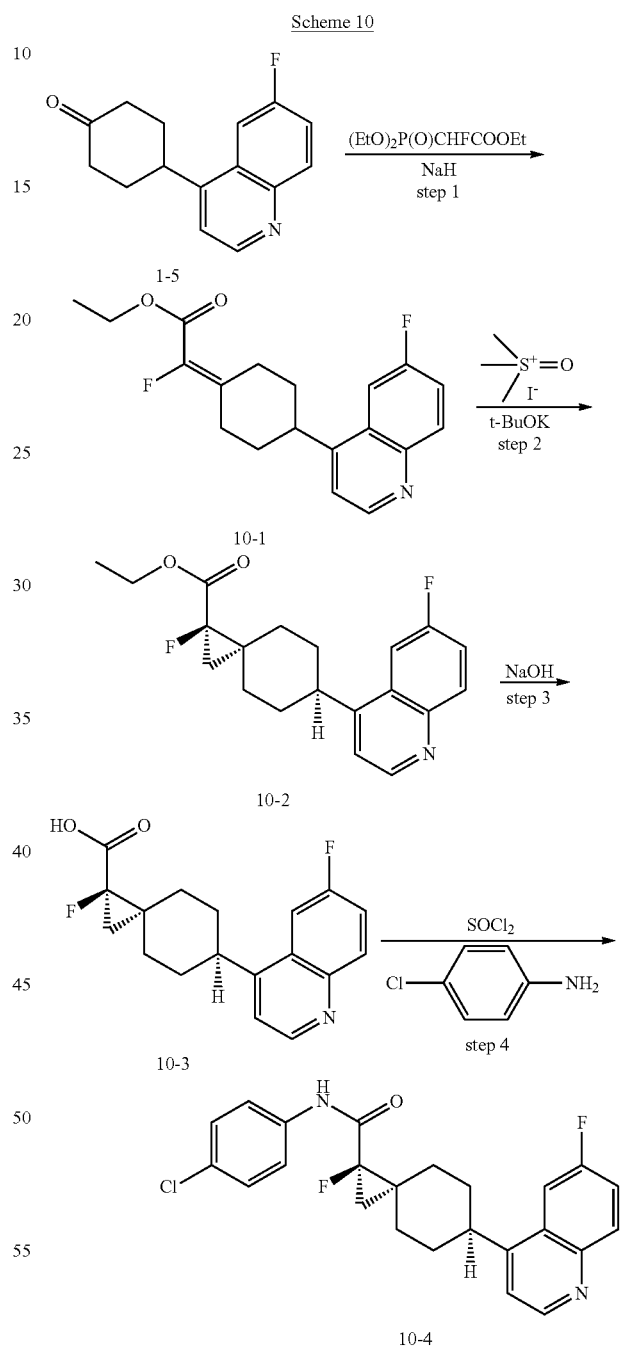

Scheme 10

Step 1

To a stirred solution of 1190 mg (4.93 mmol) of ethyl 2-(diethoxyphosphoryl)-2-fluoroacetate in 5 mL of THF at 0° C. was added 197 mg (4.93 mmol) of NaH (60% in mineral oil) in portions at 0° C. The mixture was stirred at RT for 30 min, 600 mg (2.47 mmol) of 4-(6-fluoroquinolin-4-yl)cyclohexan-1-one in 10 mL THF was added dropwise.

The mixture was stirred at RT for additional 16 h, then quenched with 10 mL of saturated NH₄Cl solution, and extracted with three 10 mL portions of EtOAc. The combined organic layers were washed with 20 mL of brine and dried over anhydrous Na₂SO₄. After filtration, the filtrate was concentrated to afford a residue, which was purified by silica gel column eluting with 0 to 30% gradient of ethyl acetate in petroleum ether to afford compound 10-1.

Step 2:

To a stirred solution of 1.05 g of t-BuOK (9.35 mmol) in 20 mL of DMSO was added 2.16 g of trimethyl(oxo)-lambda6-sulfanylium iodide (9.81 mmol). The mixture was stirred at 60° C. for 1 h, a solution of 0.82 g (2.46 mmol) of compound 10-1 in 3 mL of DMSO was added dropwise. The solution was stirred 60° C. for 50 h, cooled to RT and then quenched with 40 mL of water. The mixture was extracted with three 20 mL portions of ethyl acetate. The combined organic layers were washed with 40 mL of brine and dried over anhydrous sodium sulfate. After filtration, the filtrate was concentrated to afford a residue, which was purified by silica gel column eluting with 0 to 20% gradient of ethyl acetate in petroleum ether to give compound 10-2.

Step 3:

Compound 10-2 was converted to acid 10-3 by the procedure described in Method 1, step 8.

Step 4:

Compound 10-4 was prepared from the acid 10-3 using the procedures described in Method 3, step 1 and 2. LC-MS: m/e=427 [M+H]⁺.

Method 11

Example 10: Synthesis of N-(4-chlorophenyl)-6-(6-fluoroquinolin-4-yl)-1-methylspiro[2.5]octane-1-carboxamide (Compounds 11-5 and 11-6)

Scheme 11

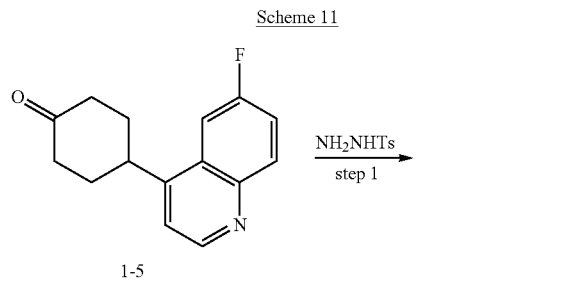

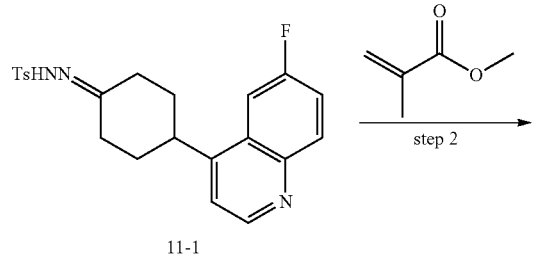

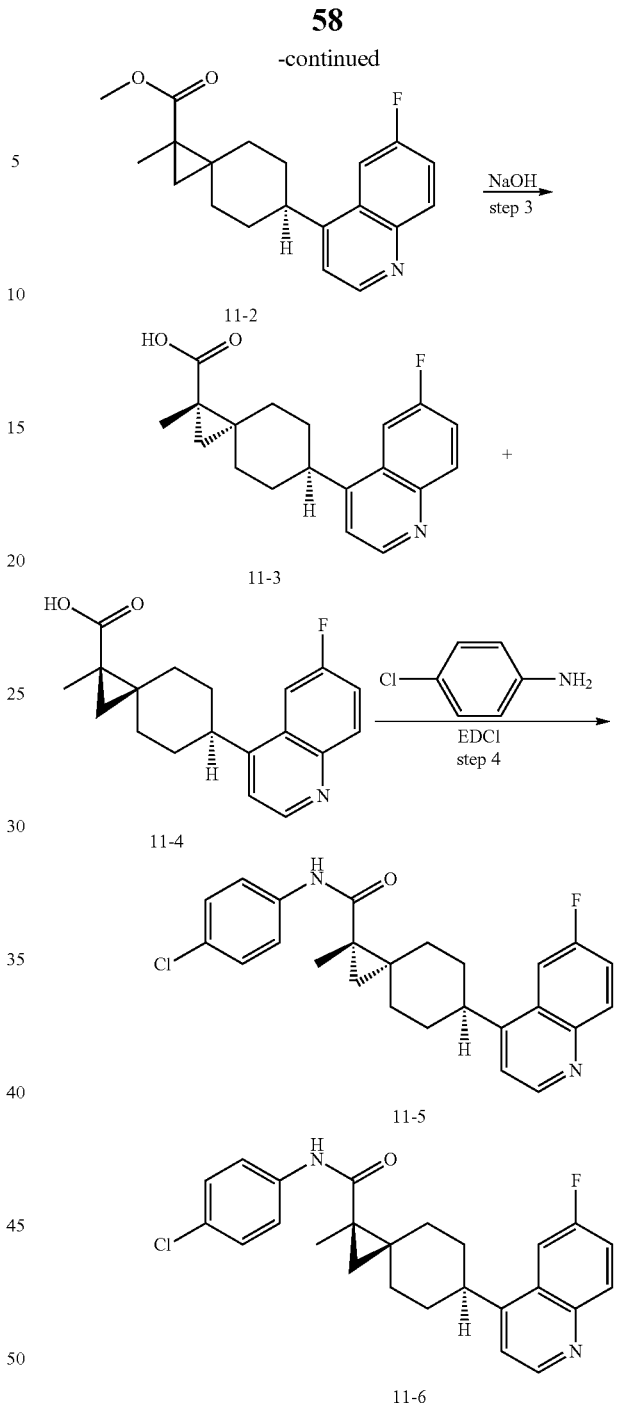

Step 1

A solution of 400 mg (1.64 mmol) of 4-(6-fluoroquinolin-4-yl)cyclohexan-1-one and 306 mg (1.64 mmol) of TsNHNH₂ in 12 mL of EtOH was stirred at 80° C. for 2 h and cooled to 0° C. The precipitates were collected by filtration and washed with three 10 mL portions of EtOH to give compound 11-1. LC-MS: m/e=412 [M+H]⁺.

Step 2:

To a stirred solution of 200 mg (0.49 mmol) of compound 11-1 and 336 mg (2.43 mmol) of K₂CO₃ in 10 mL of 1,4-dioxane was added 244 mg (2.43 mmol) of methyl 2-methylprop-2-enoate dropwise at RT under nitrogen atmosphere. The mixture was stirred at 100° C. overnight and cooled to RT. It was diluted with 30 mL of EtOAc, washed with 20 mL of brine, and dried over anhydrous Na$_2$SO$_4$. After filtration, the filtrate was concentrated to afford a residue, which was purified by chromatography on silica gel column eluting with 0 to 50% gradient of ethyl acetate in petroleum ether to afford compound 11-2. LC-MS: m/e=328 [M+H]$^+$.

Step 3:

Compound 11-2 was hydrolyzed by the procedure described in Method 1, step 8. The residue was purified by Prep-HPLC (Column: XBridge Prep OBD C18 Column 30×150 mm 5 um; Mobile Phase A: Water (10 mM NH$_4$HCO$_3$), Mobile Phase B: ACN; Flow rate: 60 mL/min; Gradient: 21% B to 34% B in 8 min; 220 nm; Rt: 5.32, 7.68 min) to give compound 11-3 (peak 1) and 11-4 (Peak 2). 11-3, LC-MS: m/e=314 [M+H]$^+$. 11-4, LC-MS: m/e=314 [M+H]$^+$.

Step 4:

Compound 11-3 and 11-4 were converted to compound 11-5 and 11-6 respectively, using the procedure described in Method 2, step 1. Compound, 11-5, LC-MS: m/e=423 [M+H]$^+$. Compound, 11-6, LC-MS: m/e=423 [M+H]$^+$.

Method 12

Example 12: Synthesis of N-(4-chlorophenyl)-6-(6-fluoroquinolin-4-yl)-6-azaspiro[2.5]octane-1-carboxamide (Compounds 12-6 and 12-7)

Scheme 12

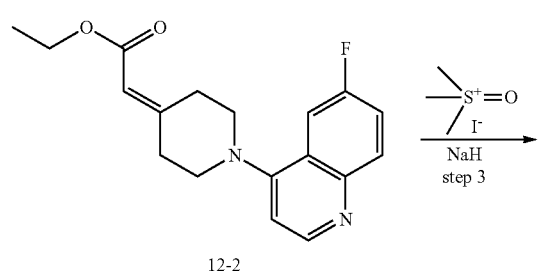

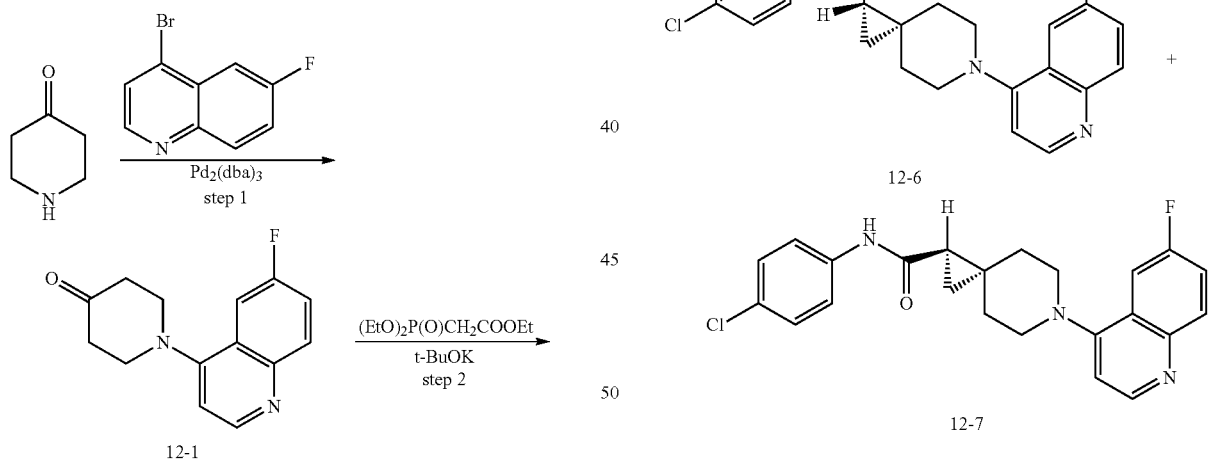

Step 1

To a stirred solution of 1.0 g (4.5 mmol) of 4-bromo-6-fluoroquinoline and 1.82 g (13.4 mmol) of piperidin-4-one hydrochloride in 25 mL of toluene was added 0.23 g (0.22 mmol) of Pd$_2$(dba)$_3$CHCl$_3$, 0.11 g (0.22 mmol) of X-Phos and 5.8 g (17.8 mmol) of Cs$_2$CO$_3$ under Ar atmosphere. The reaction mixture was stirred at 100° C. overnight. The mixture was cooled to rt and filtered through Celite. The filter cake was washed with 20 mL of ethyl acetate. The filtrate was concentrated to afford a crude, which was purified by chromatography on silica gel eluting with 50% ethyl acetate in petroleum ether to afford compound 12-1. LC-MS: m/e=245 [M+H]$^+$.

Step 2:

Compound 12-2 was prepared from 12-1 using the procedure described in Method 1, Step 6. LC-MS: m/e=315 [M+H]+.

Step 3:

Compound 12-3 was prepared from 12-2 using the procedure described in Method 1, Step 7. LC-MS: m/e=329 [M+H]+.

Step 4:

Compound 12-4 was prepared from 12-3 using the procedure described in Method 1, Step 8. LC-MS: m/e=301 [M+H]+.

Step 5:

Compound 12-5 was prepared from 12-4 using the procedure described in Method 1, Step 9. LC-MS: m/e=410 [M+H]+.

Step 6:

Compound 12-5 was resolved by chiral HPLC separation (Column: CHIRALPAK OD-3 4.6*100 mm 3 μm; Mobile phase: A: $CO_2$, B: 20 mmol/L $NH_3$ in MeOH, gradient: 90:10 to 50:50 (A:B) over 3.0 min, 50:50 (A: B) for 3.0 min; UV detection: 220 nm) to yield compound 12-6 (Peak 1), LC-MS: m/e=410 [M+H]+; and compound 12-7 (Peak 2), LC-MS: m/e=410 [M+H]+.

Method 13

Example 13: Synthesis of 4-chloro-N-(6-(6-fluoro-quinolin-4-yl)-6-azaspiro[2.5]octan-1-yl)benzamide (Compound 13-3)

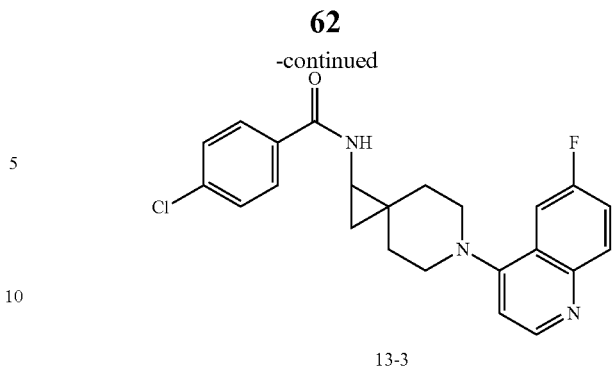

13-3

Step 1

Compound 12-1 was prepared from 12-4 using the procedure described in Method 9, Step 1. LC-MS: m/e=372 [M+H]+.

Step 2:

Compound 13-2 is prepared from 13-1 using the procedure described in Method 9, Step 2. LC-MS: m/e=272 [M+H]+.

Step 3:

Compound 13-3 is prepared from 13-2 using the procedure described in Method 1, Step 9. LC-MS: m/e=410 [M+H]+.

Method 14

Example 14: Synthesis of 4-chloro-N-(7-(6-fluoro-quinolin-4-yl)spiro[3.5]nonan-1-yl)benzamide (Compound 14-7)

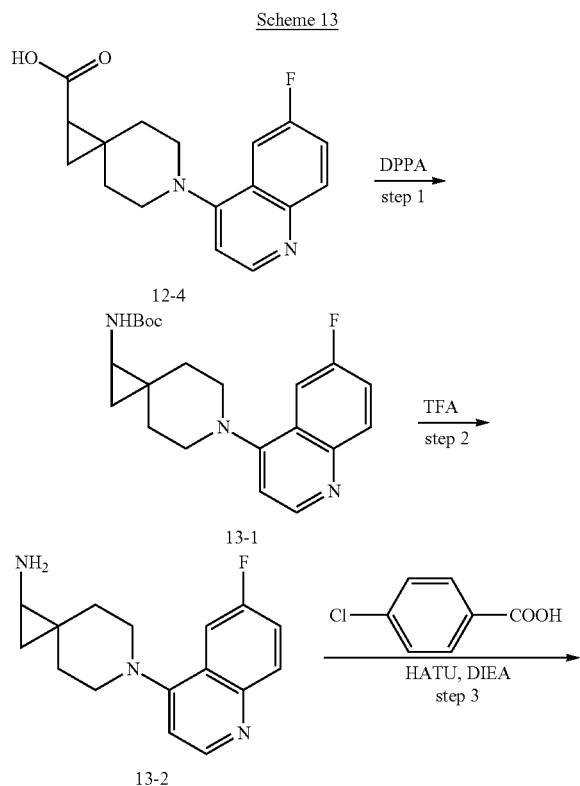

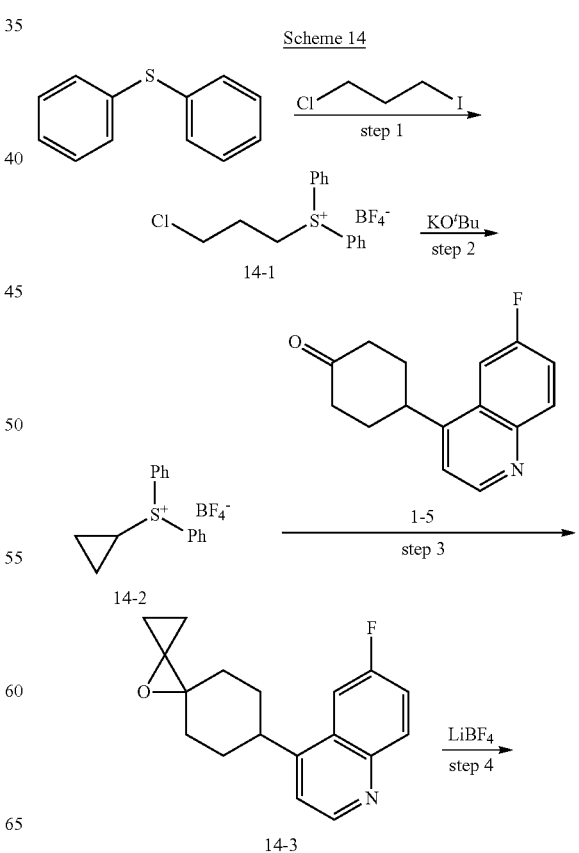

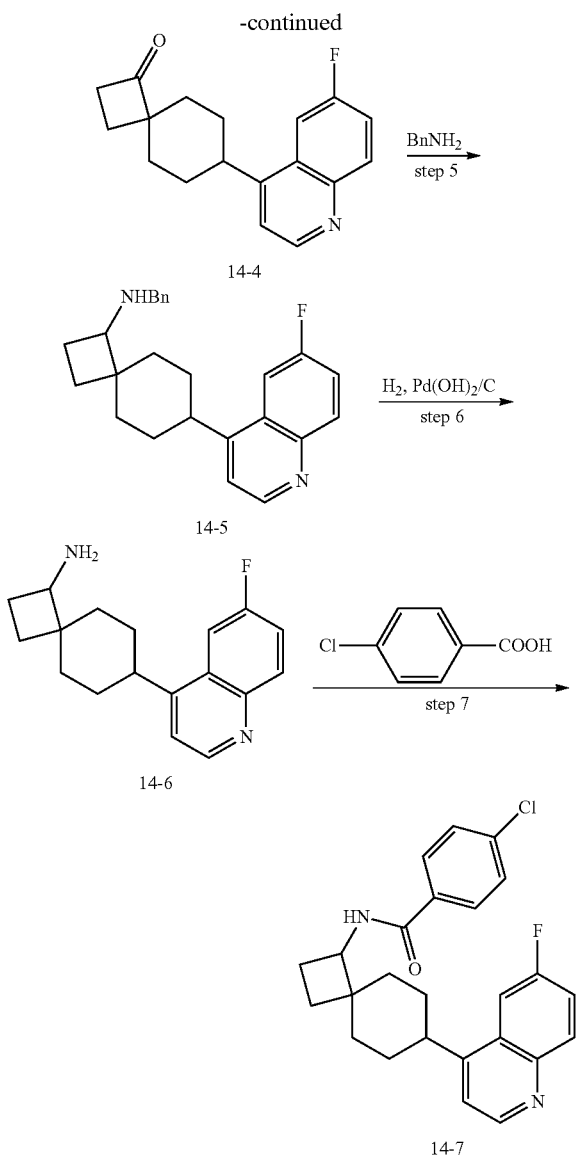

Step 1

To a stirred solution of 1.00 g (5.37 mmol) of phenylsulfanylbenzene and 3.30 g (20.0 mmol) of 1-chloro-3-iodopropane in 3 mL of CH$_3$NO$_2$ was added 1.00 g (5.14 mmol) of AgBF$_4$ at RT under argon atmosphere. The mixture was stirred at RT for 20 h and diluted with 5 mL of DCM. It was filtered through a pad of Celite; the filter cake was washed with three 5 mL portions of DCM. The combined filtrates were concentrated to give a residue, which was triturated with 30 mL of diethyl ether for 2 h, and then filtered to afford salt 14-1. LC-MS: m/e=263 [M]$^+$.

Step 2:

To a stirred solution of 1.30 g (3.71 mol) of compound 14-1 in 15 mL of THF was added a solution of 0.40 g (3.56 mmol) of t-BuOK in 2.8 mL of DMSO dropwise at RT over a period of 1 h. The mixture was diluted with 10 mL of DCM and stirred for 10 min. The mixture was extracted with two 5 mL portions of DCM. The combined organic extracts were washed with 10 mL of brine and dried over anhydrous Na$_2$SO$_4$. The mixture was concentrated to give a residue, which was stirred in 100 mL of diethyl ether for 1 h. The precipitates were collected by filtration and washed with two 10 mL portions of diethyl ether to afford compound 14-2. LC-MS: m/e=227 [M]$^+$.

Step 3:

To a stirred mixture of 775 mg (2.47 mmol) of compound 14-2 in 6 mL of THF were added 5.9 mL (5.9 mmol, 1 M in THF) of KHMDS at −40° C. under argon atmosphere. The resulting yellow solution was stirred at −40° C. for 10 min, then a solution of 500 mg (2.06 mmol) of compound 1-5 in 6 mL of THF was added in one portion. The solution was stirred at −40° C. for 30 min, allowed to warm to room temperature for additional 2 h. The reaction was quenched with water at RT and extracted with three 20 mL portions of ethyl acetate. The combined organic extracts were washed with two 20 mL portions of brine and dried over anhydrous Na$_2$SO$_4$. The mixture was concentrated to give a residue, which was purified by C18 silica gel column eluting with ACN: H$_2$O (0.05% FA)=40% to afford compound 14-3. LC-MS: m/e=284 [M+H]$^+$.

Step 4:

To a stirred solution of 410 mg (1.45 mmol) of compound 14-3 in 5 mL of toluene was added 41 mg (0.43 mmol) of lithium tetrafluoroboranide at RT. The mixture was stirred at 80° C. for 2 h under nitrogen atmosphere and quenched with 10 mL of water at RT. It was extracted with three 10 mL portions of ethyl acetate; the combined organic extracts were washed with 10 mL of brine and dried over anhydrous Na$_2$SO$_4$. It was filtered and the filtrate was concentrated to give a residue, which was purified by Prep-TLC (petroleum ether/ethyl acetate=1:1) to afford compound 14-4. LC-MS: m/e=284 [M+H]$^+$.

Step 5:

To a stirred solution of 300 mg (1.06 mmol) of compound 14-4 in 7 mL of DCE were added 340 mg (3.18 mmol) of benzylamine, 31.8 mg (0.53 mmol) of AcOH and 99.8 mg (1.59 mmol) of NaBH$_3$CN. The reaction mixture was irradiated in microwave at 130° C. for 1 h and cooled to RT. It was quenched by 20 mL of water; the aqueous layer was extracted with three 10 mL portions of ethyl acetate. The combined organic extracts were washed with 10 mL of brine and dried over anhydrous Na$_2$SO$_4$. The resulting mixture was concentrated to give a residue, which was purified by reverse flash chromatography (120 g of C18 silica gel; ACN, 0.05% NH$_4$HCO$_3$ in water, 50% to 100% gradient in 20 min; 220 nm, UV 254 nm) to afford compound 14-5. LC-MS: m/e=375 [M+H]$^+$.

Step 6:

To a solution of 50 mg (0.13 mmol) of compound 14-5 in 5 mL of THF was added 50 mg (0.36 mmol) of 20% wet Pd(OH)$_2$/C. The mixture was stirred at 50° C. overnight under hydrogen atmosphere and filtered; the filter cake was washed with two 5 mL portions of THF. The combined filtrates were concentrated to give a residue, which was purified by Prep-TLC (DCM: MeOH 3:1) to afford compound 14-6. LC-MS: m/e=285 [M+H]$^+$.

Step 7:

Compound 14-6 was converted to compound 14-7 using the procedure described in Method 1, step 9. LC-MS: m/e=423 [M+H]$^+$.

Method 15

Example 15: Synthesis of N-(4-chlorophenyl)-7-(6-fluoroquinolin-4-yl)spiro[3.5]nonane-1-carboxamide (Compound 15-3)

Scheme 15

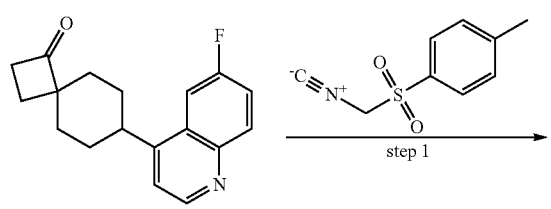

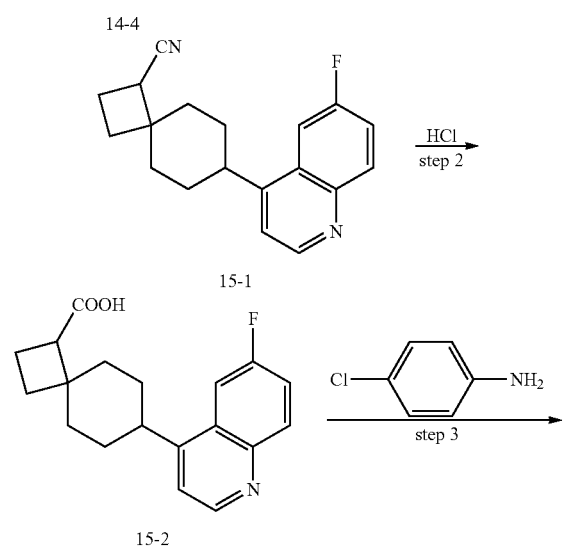

Step 1

To a solution of 200 mg (0.71 mmol) of compound 14-4 were added a solution of 166 mg (0.85 mmol) of TOSMIC in 3 mL of DME and a solution of 158.4 mg (1.41 mmol) of t-BuOK in 0.5 mL of DME and 0.5 mL of t-BuOH via syringe at 0° C. The mixture was stirred at 0° C. for 30 min and at RT for 2 h. It was diluted with 20 mL of water and extracted with three 30 mL portions of ethyl acetate. The combined organic extracts were washed with 20 mL of brine and dried over anhydrous $Na_2SO_4$. After filtration, the filtrate was concentrated to afford a residue, which was purified by silica gel column chromatography eluting with 0 to 50% of ethyl acetate in petroleum ether to afford compound 15-1. LC-MS: m/e=295 [M+H]$^+$.

Step 2:

A solution of 50 mg (170 mmol) of compound 15-1 in 1 mL of 12 N HCl was stirred at 100° C. overnight and cooled to RT. It was concentrated under reduced pressure and diluted with 10 mL of DCM. The mixture was filtered; the filter cake was washed with DCM. The filtrate was concentrated under reduced pressure to afford compound 15-2. LC-MS: m/e=314 [M+H]$^+$.

Step 3:

Compound 15-2 was converted to compound 15-3 using the procedure described in Method 2, step 1. LC-MS: m/e=423 [M+H]$^+$.

Method 16

Example 16: Synthesis of N-(4-chlorophenyl)-7-(6-fluoroquinolin-4-yl)spiro[3.5]nonane-2-carboxamide (Compounds 16-7 and 16-8)

Scheme 16

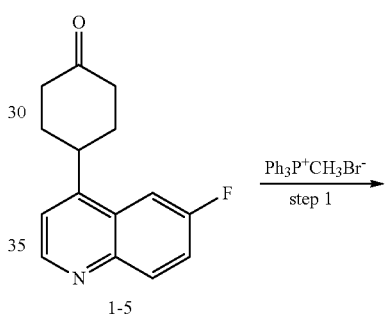

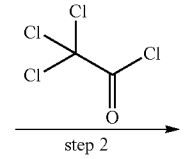

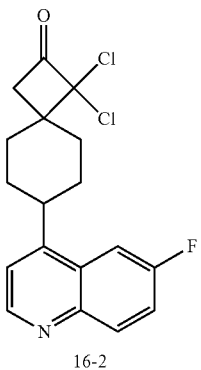

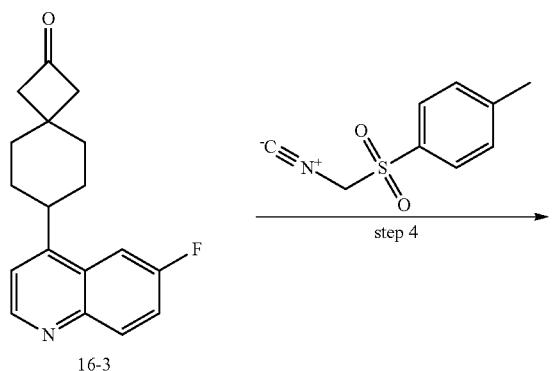

16-3

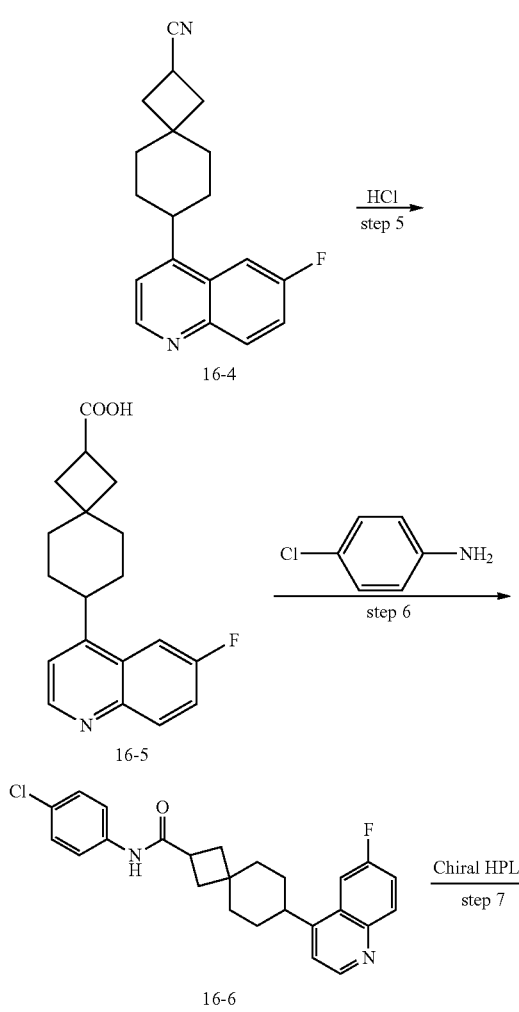

16-4

16-5

16-6

16-7*

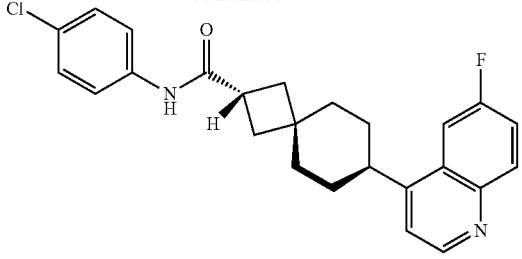

16-8*

*The configurations were arbitrarily assigned and not determined

Step 1

To a stirred solution of 8.1 g (22.7 mmol) of methyltriphenylphosphonium bromide in 80 mL of THF was added 9.0 mL (2.5 M in hexanes, 22.5 mmol) of n-BuLi dropwise at −5° C. under argon atmosphere. The solution was stirred at 0° C. for 1 h. To the above mixture was added 5.0 g (20.6 mmol) of compound 1-5 dropwise at 0° C. The mixture was stirred overnight at RT and quenched by addition 50 mL of NH$_4$Cl solution. It was extracted with three 100 mL portions of ethyl acetate; the combined organic layers were washed with 100 mL of brine and dried over anhydrous Na$_2$SO$_4$. After filtration, the filtrate was concentrated to give a residue, which was purified by silica gel column chromatography eluting with 0 to 14% gradient of ethyl acetate in petroleum ether to afford compound 16-1. LC-MS: m/e=242 [M+H]$^+$.

Step 2:

To a stirred solution of 3.0 g (12.4 mmol) of compound 16-1 in 100 mL of Et$_2$O was added 8.1 g (124 mmol) of zinc-copper couple in portions at RT under Ar atmosphere. To the above mixture was added a solution of 11.3 g (62.2 mmol) of trichloroacetyl chloride in 100 mL of Et$_2$O dropwise over a period of 10 h. The mixture was stirred overnight at RT and quenched with aqueous NaHCO$_3$. The mixture was filtered; the filter cake was washed with ethyl acetate (3×50 mL). The combined filtrates were concentrated under reduced pressure; the residue was extracted with three 100 mL portions of ethyl acetate. The combined organic layers were washed with 100 mL of brine and dried over anhydrous Na$_2$SO$_4$. After filtration, the filtrate was concentrated to afford compound 16-2, which was used in the next step directly without further purification. LC-MS: m/e=352 [M+H]$^+$.

Step 3:

To a stirred solution of 6.0 g (23.7 mmol) of compound 16-2 in 60 mL of AcOH was added 15.4 g (237 mmol) of Zn in portions at RT. The mixture was stirred overnight at RT and filtered; the filter cake was washed with three 100 mL portions of ethyl acetate. The filtrate was concentrated under reduced pressure; the residue was extracted with three 100 mL portions of ethyl acetate. The combined organic layers were washed with 100 mL of brine and dried over anhydrous Na$_2$SO$_4$. After filtration, the filtrate was concentrated under reduced pressure. The residue was purified by reverse C18 silica gel flash chromatography to give compound 16-3. LC-MS: m/e=284 [M+H]$^+$.

Step 4:

Compound 16-3 was converted to compound 16-4 using the procedure described in Method 15, step 1. LC-MS: m/e=295 [M+H]$^+$.

Step 5:

Compound 16-4 was converted to compound 16-5 using the procedure described in Method 15, step 2. LC-MS: m/e=314 [M+H]+.

Step 6:

Compound 16-5 was converted to compound 16-6 using the procedure described in Method 2, step 1. LC-MS: m/e=423 [M+H]+.

Step 7:

Compound 16-6 was resolved by Chiral-HPLC (Column: Chiralpak AD-3, 3.0*100 mm, 3.0 μm; Mobile phase: A: CO₂ gas, Mobile phase B: 0.1% DEA in MeOH, flow rate 2 mL/min. gradient: 90:10 to 50:50(A:B) over 4.0 min, 50:50 (A:B) for 2.0 min; UV detection: 220/254 nm) to afford compound 16-7 (peak 1), LC-MS: m/e=423 [M+H]+ and compound 16-8 (peak 2), LC-MS: m/e=423 [M+H]+.

Method 17

Example 17: Synthesis of 4-chloro-N-(7-(6-fluoro-quinolin-4-yl)spiro[3.5]nonan-2-yl)benzamide (Compounds 17-6 and 17-7)

Scheme 17

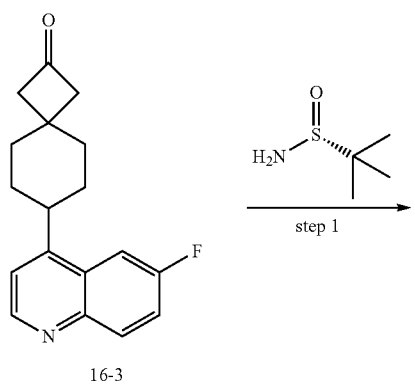

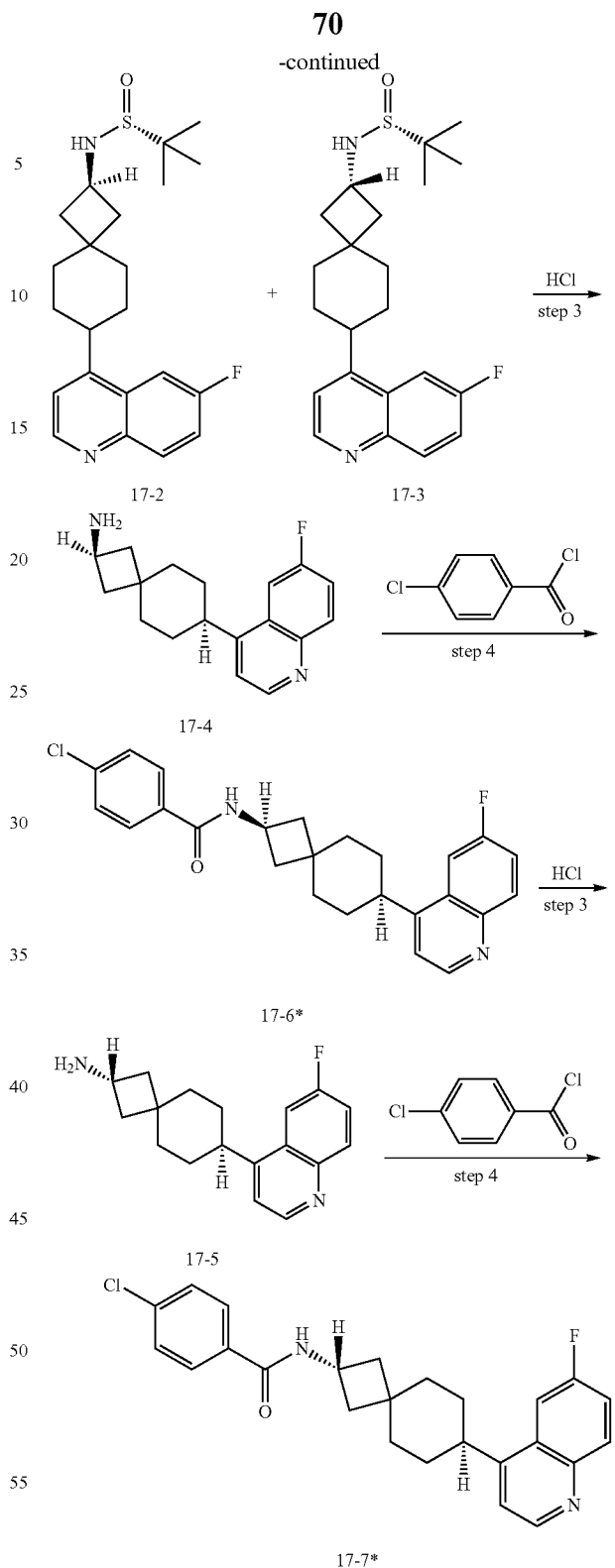

*The configurations were arbitrarily assigned and not determined

Step 1

To a solution of 200 mg (0.706 mmol) of compound 16-3 in 10 mL of THF were added 128 mg (1.1 mmol) of (R)-2-methylpropane-2-sulfinamide and 800 mg (2.8 mmol) of Ti(Oi-Pr)₄ dropwise with stirring. The mixture was irradiated in microwave at 100° C. for 4 h. It was concentrated;

the residue was diluted with 15 mL of ethyl acetate and 0.8 mL of water. The solids were filtered out; the filtrate was concentrated to give compound 17-1. LC-MS: m/e=387 [M+H]⁺.

Step 2:

To a solution of 60 mg (0.16 mmol) of compound 17-1 in 3 mL of THF was added 0.19 mL (1.1 mmol) of DIBAL dropwise at −78° C. The solution was stirred at −40° C. for 2 h and then quenched by addition of 15 mL of saturated NH₄Cl solution. It was extracted with 3 portions of 10 mL ethyl acetate. The organic layers were combined and concentrated to give a residue, which was purified by Prep-HPLC (Column, C18 silica gel; mobile phase, acetonitrile/water=30; Detector, UV220) to give compound 17-2, LC-MS: m/e=389 [M+H]⁺ and 17-3, LC-MS: m/e=389 [M+H]⁺.

Step 3:

To a solution of 25 mg (0.064 mmol) of compound 17-2 in 1 mL of methanol was added 0.25 mL of 4 N HCl in dioxane. The solution was stirred at RT for 2 h and concentrated to give compound 17-4 as HCl salt. LC-MS: m/e=285 [M+H]⁺.

Compound 17-3 was converted to compound 17-5 HCl salt similarly. LC-MS: m/e=285 [M+H]⁺.

Step 4:

To a solution of 23 mg (0.07 mmol) of compound 17-4 HCl salt in 2 mL of THF was added 36 mg (0.35 mmol) of triethylamine and 18 mg (0.11 mmol) of 4-chlorobenzoyl chloride. The solution was stirred at RT for 2 h. The reaction was then quenched by addition of 15 mL of saturated NaHCO₃ and extracted with three 10 mL portions of ethyl acetate. The organic layers were combined and dried under anhydrous Na₂SO₄ and concentrated. The residue was purified by Prep-HPLC (Column, XBridge Prep OBD C18 Column, 19*250 mm, 5 μm; mobile phase, Water (0.1% TFA) and ACN (57% PhaseB up to 76% in 8 min); Detector, UV) to give compound 17-6. LC-MS: m/e=423 [M+H]⁺.

Compound 17-5 HCl salt was converted to compound 17-7 similarly. LC-MS: m/e=423 [M+H]⁺.

The two amide compounds listed in Table 7 were prepared from intermediate 17-4 using the procedure described in Method 1, step 9.

TABLE 7

Compound structures, their identification numbers and LCMS data

| Compound Structure | LCMS [M + H]⁺ |
|---|---|
| 17-8 | 414 |
| 17-9 | 390 |

Method 18

Example 18: Synthesis of 4-chloro-N-(7-(6-fluoro-quinolin-4-yl)-7-azaspiro[3.5]nonan-2-yl)benzamide (Compound 18-5)

Scheme 18

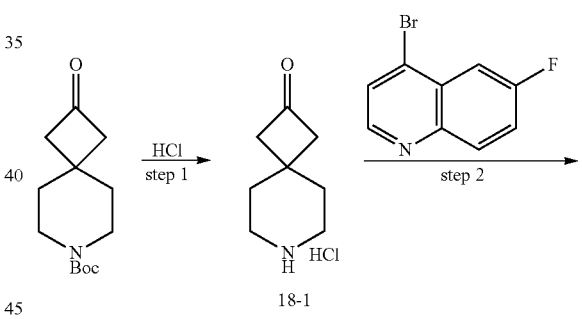

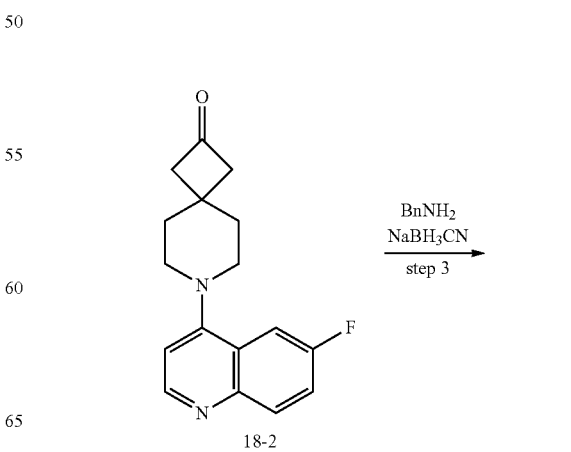

-continued

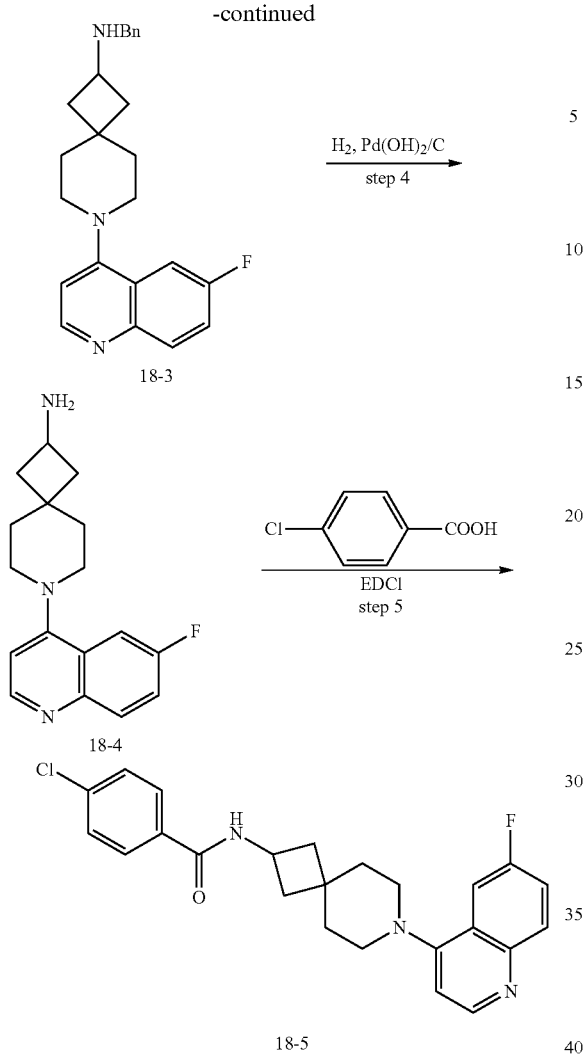

Step 1

A solution of 600 mg (2.51 mmol) tert-butyl 2-oxo-7-azaspiro[3.5]nonane-7-carboxylate in 5 mL 4 N HCl in 1,4-dioxane was stirred at RT for 2 h. The mixture was concentrated to afford compound 18-1 HCl salt, which was used in the next step directly without further purification.

Step 2:

Compound 18-1 was converted to compound 18-2 using the procedure described in Method 12, step 1. LC-MS: m/e=285 [M+H]$^+$.

Step 3:

Compound 18-2 was converted to compound 18-3 using the procedure described in Method 14, step 5. LC-MS: m/e=376 [M+H]$^+$.

Step 4:

Compound 18-3 was converted to compound 18-4 using the procedure described in Method 14, step 6. LC-MS: m/e=286 [M+H]$^+$.

Step 5:

Compound 18-4 was converted to compound 18-5 using the procedure described in Method 1, step 9. LC-MS: m/e=424 [M+H]$^+$.

Method 19

Example 19: Synthesis of N-(4-chlorophenyl)-7-(6-fluoroquinolin-4-yl)-7-azaspiro[3.5]nonane-2-carboxamide (Compound 19-3)

Scheme 19

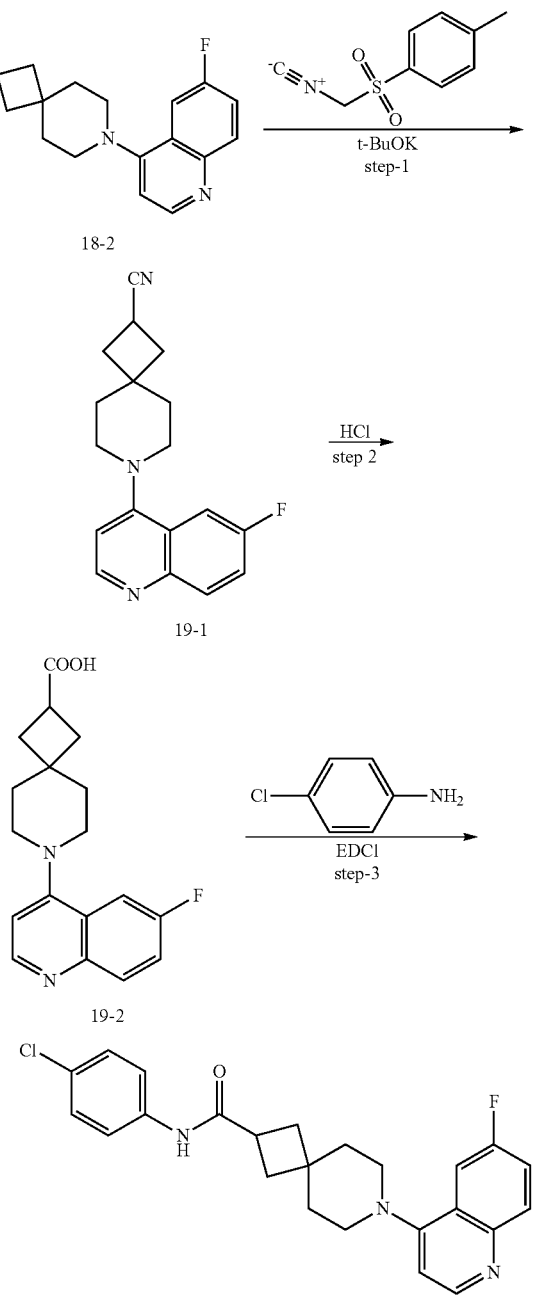

Step 1

Compound 18-2 was converted to compound 19-1 using the procedure described in Method 15, step 1. LC-MS: m/e=296 [M+H]$^+$.

75

Step 2:

Compound 18-2 was converted to compound 19-1 using the procedure described in Method 15, step 2. LC-MS: m/e=315 [M+H]+.

Step 3:

Compound 18-2 was converted to compound 19-1 using the procedure described in Method 2, step 1. LC-MS: m/e=424 [M+H]+.

Method 20

Example 20: Synthesis of N-(4-chlorophenyl)-7-(1,6-naphthyridin-4-yl)spiro[3.5]nonane-2-carboxamide (Compounds 20-8 and 20-9)

76

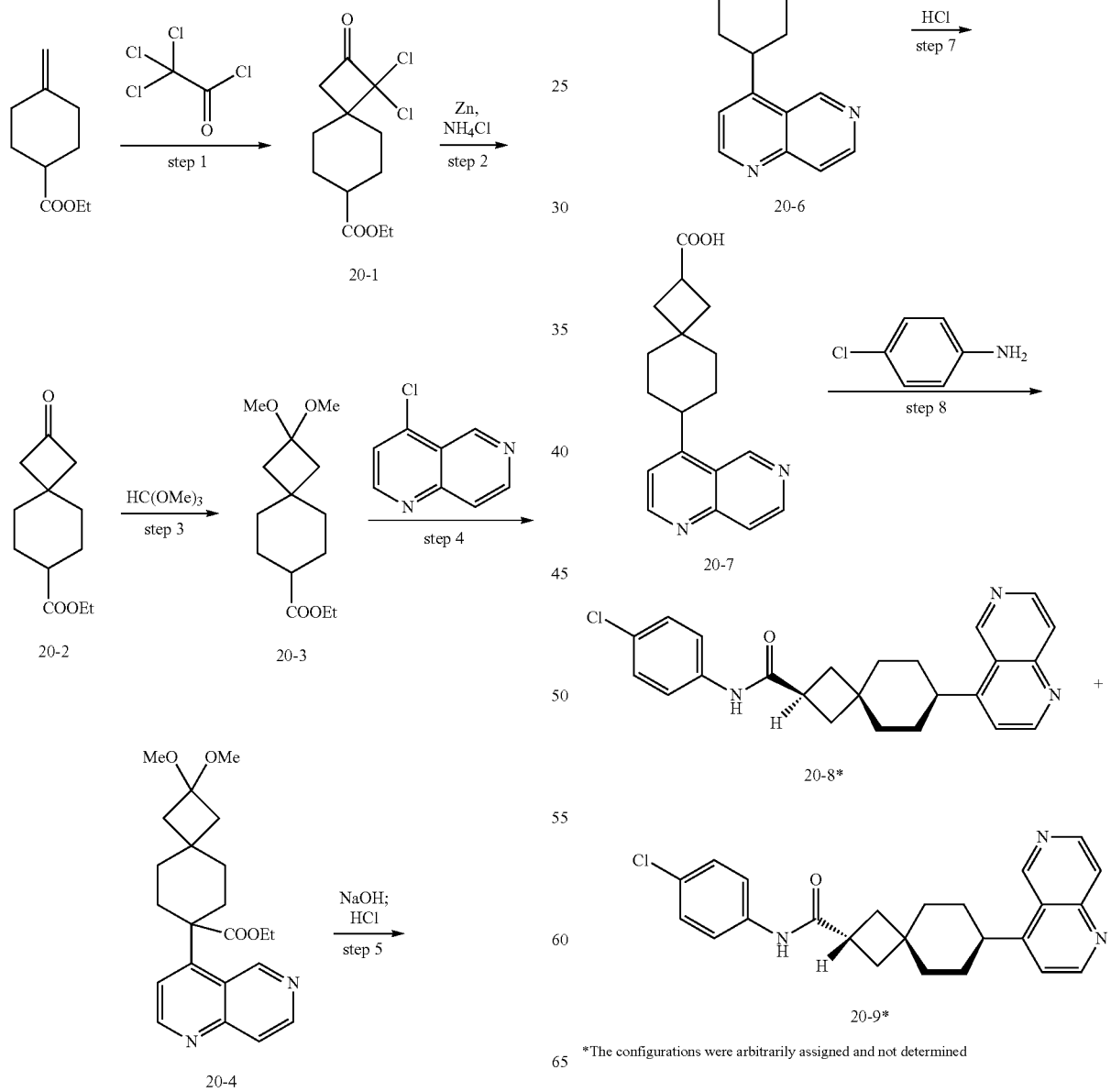

*The configurations were arbitrarily assigned and not determined

77

Step 1

Compound 20-1 was prepared from ethyl 4-methylidene-cyclohexane-1-carboxylate using the procedure described in Method 16, step 2.

Step 2:

Compound 20-1 was converted to compound 20-2 using the procedure described in Method 16, step 3. $^1$H NMR (400 MHz, DMSO-d6) δ 4.05 (q, J=7.1 Hz, 2H), 2.73 (s, 4H), 1.80 (ddd, J=12.9, 6.1, 2.5 Hz, 2H), 1.75-1.65 (m, 2H), 1.63-1.51 (m, 2H), 1.51-1.32 (m, 2H), 1.18 (t, J=7.1 Hz, 3H).

Step 3:

To a solution of 500 mg (2.4 mmol) of compound 20-2 in 10 mL of DCM and 10 mL of MeOH were added 2.5 g (24 mmol) of trimethoxymethane and 41 mg (0.24 mmol) of toluenesulfonic acid. The resulting mixture was stirred at RT overnight under nitrogen atmosphere. The mixture was concentrated under vacuum to afford a residue, which was purified by silica gel column chromatography eluting with 3% of ethyl acetate in petroleum ether to afford compound 20-3. $^1$H NMR (400 MHz, DMSO-d6) δ 4.04 (q, J=7.1 Hz, 2H), 3.02 (s, 6H), 2.23 (dd, J=9.1, 5.4 Hz, 1H), 1.84-1.77 (m, 4H), 1.76-1.55 (m, 4H), 1.43-1.28 (m, 4H), 1.17 (t, J=7.1 Hz, 3H).

Step 4:

Compound 20-3 was converted to compound 20-4 using the procedure described in Method 7, step 1. LC-MS: m/e=385 [M+H]$^+$.

Step 5:

Compound 20-4 was converted to compound 20-5 using the procedure described in Method 7, step 2. LC-MS: m/e=267 [M+H]$^+$.

Step 6:

Compound 20-5 was converted to compound 20-6 using the procedure described in Method 15, step 1. LC-MS: m/e=278 [M+H]$^+$.

Step 7:

Compound 20-6 was converted to compound 20-7 using the procedure described in Method 15, step 2. LC-MS: m/e=297 [M+H]$^+$.

Step 8:

Following the procedure described in Method 1, step 9, compound 20-7 was converted to the racemic amide, which was resolved by Chiral-HPLC (Column, CHIRALPAK IG, 2*25 mm, 5 μm; mobile phase A: Hex (8 mM NH$_3$.MeOH)—HPLC mobile phase B: EtOH; Flow rate: 18 mL/min; Gradient: 50 B to 50 B in 12 min; UV detection: 220/254 nm) to give compound 20-8, (peak 1), LC-MS: m/e=406 [M+H]$^+$ and compound 20-9, (peak 2), LC-MS: m/e=406 [M+H]$^+$.

78

Method 21

Example 21: Synthesis of N-7-(1,6-naphthyridin-4-yl)spiro[3.5]nonan-2-yl)-4-chlorobenzamide (Compounds 21-4 and 21-5)

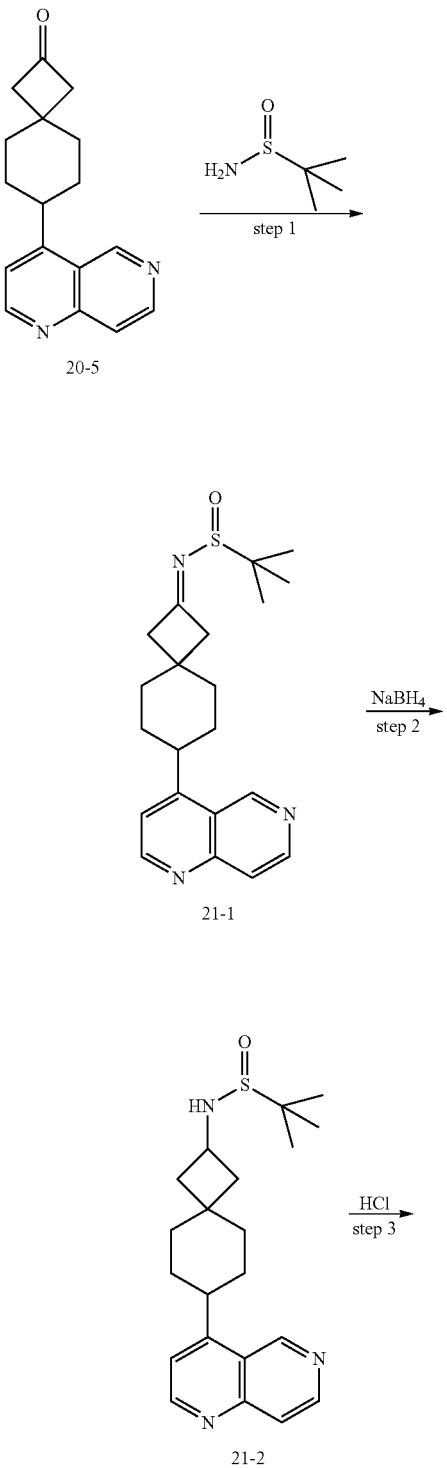

79
-continued

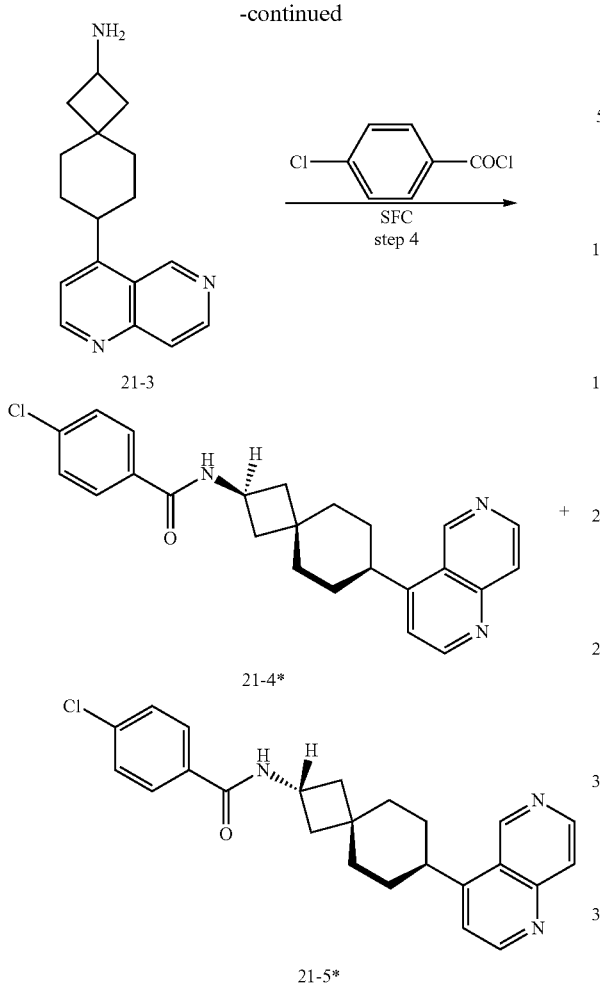

21-3

21-4*

21-5*

*The configurations were arbitrarily assigned and not determined

Step 1

Compound 20-5 was converted to compound 21-1 using the procedure described in Method 17, step 1. LC-MS: m/e=370 [M+H]$^+$.

Step 2:

To a stirred solution of 350 mg (0.95 mmol) of compound 21-1 in 5 mL of MeOH was added 43 mg (1.1 mmol) of NaBH$_4$ at 0° C. The mixture was stirred at 0° C. for 30 min under nitrogen atmosphere and quenched with water at 0° C. The mixture was acidified to pH 8 with 2 M HCl and extracted with three 20 mL portions of ethyl acetate. The combined organic extracts were washed with 10 mL of brine and dried over anhydrous Na$_2$SO$_4$. After filtration, the filtrate was concentrated under reduced pressure to afford compound 21-2. LC-MS: m/e=372 [M+H]$^+$.

Step 3:

Compound 21-2 was converted to compound 21-3 using the procedure described in Method 17, step 3. LC-MS: m/e=268 [M+H]$^+$.

Step 4:

Following procedure described in Method 17, step 4, compound 21-3 was first converted to its racemic amide, which was resolved by SFC to give compound 21-4, LC-MS: m/e=406 [M+H]$^+$ and compound 21-5, LC-MS: m/e=406 [M+H]$^+$.

80

Method 22

Example 22: Synthesis of N-(7-(1,6-naphthyridin-4-yl)-7-azaspiro[3.5]nonan-2-yl)-4-chlorobenzamide (Compound 22-5)

Scheme 22

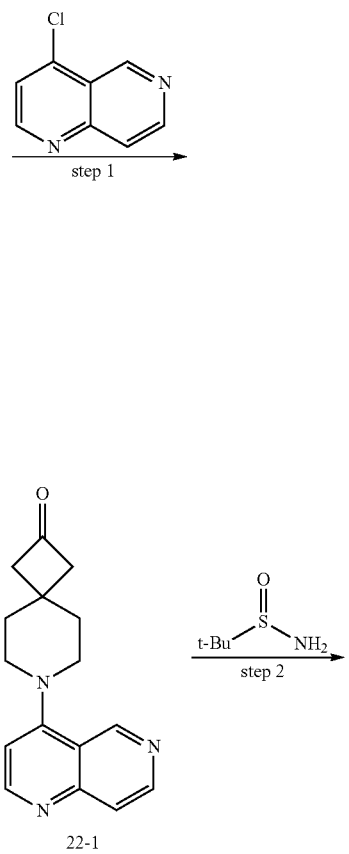

22-1

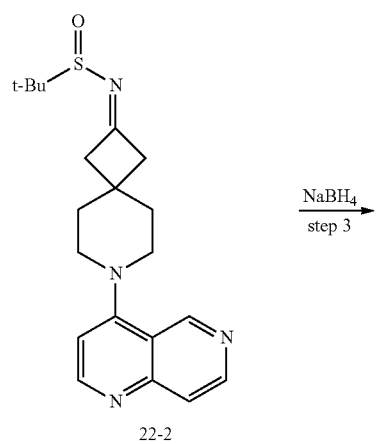

22-2

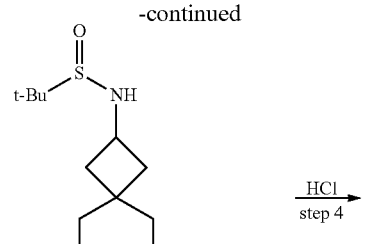

22-3

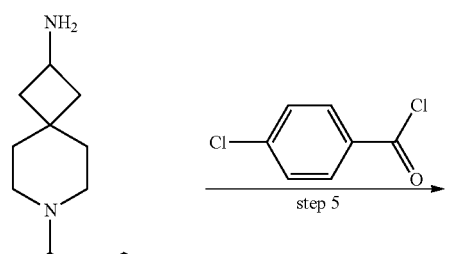

22-4

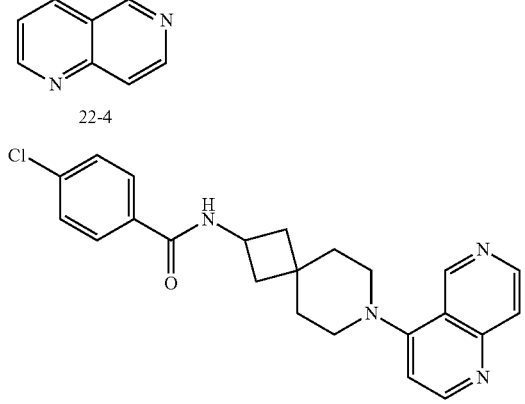

22-5

Step 1

To a stirred solution of 320 mg (1.82 mmol) of compound 18-1 hydrochloride and 790 mg (6.12 mmol) of DIEA in 10 mL of NMP was added 200 mg (1.22 mmol) of 4-chloro-1,6-naphthyridine. The mixture was stirred at for 4 h under nitrogen atmosphere. The mixture was diluted with 10 mL of water and extracted with three 20 mL portions of ethyl acetate. The combined organic extracts were washed with 20 mL of brine and dried over anhydrous $Na_2SO_4$. After filtration, the filtrate was concentrated to afford a residue, which was purified by chromatography on silica gel column eluting with 0 to 6% gradient of methanol in dichloromethane to afford a residue, which was purified by C18 silica gel eluting with 0 to 40% gradient of acetonitrile in water (0.05% $NH_4HCO_3$) to afford compound 22-1. LC-MS: m/e=268 [M+H]$^+$.

Step 2:

Compound 22-1 was converted to compound 22-2 using the procedure described in Method 17, step 1. LC-MS: m/e=371 [M+H]$^+$.

Step 3:

Compound 22-2 was converted to compound 22-3 using the procedure described in Method 21, step 2. LC-MS: m/e=373 [M+H]$^+$.

Step 4:

Compound 22-3 was converted to compound 22-4 using the procedure described in Method 17, step 3. LC-MS: m/e=269 [M+H]$^+$.

Step 5:

Following procedure described in Method 17, step 4, compound 22-4 was first converted to its racemic amide, which was resolved by SFC to give compound 22-5, LC-MS: m/e=407 [M+H]$^+$.

Method 23

Example 23: Synthesis of 4-chloro-N-(1-(4-(6-fluoroquinolin-4-yl)cyclohexyl)cyclopropyl)-benzamide (Compounds 23-5A and 23-5B)

Scheme 23

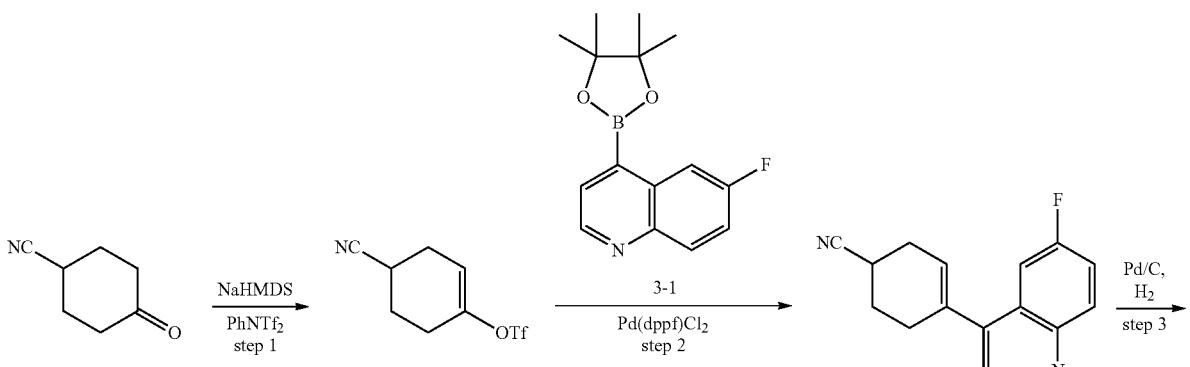

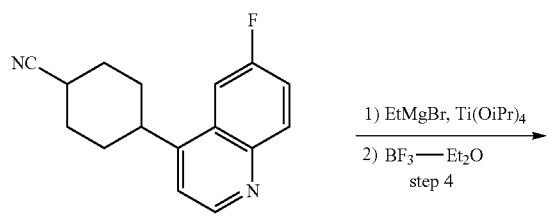

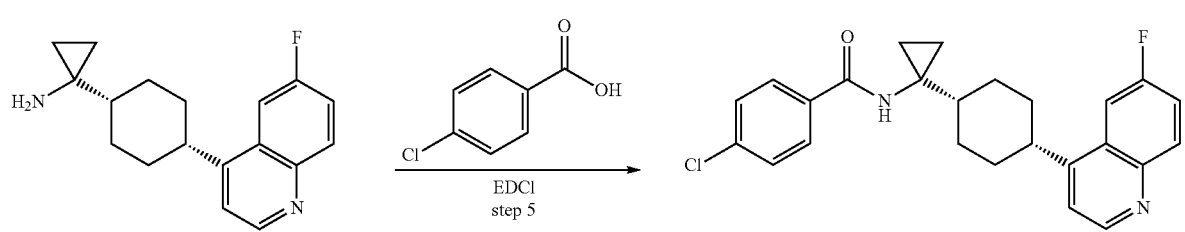

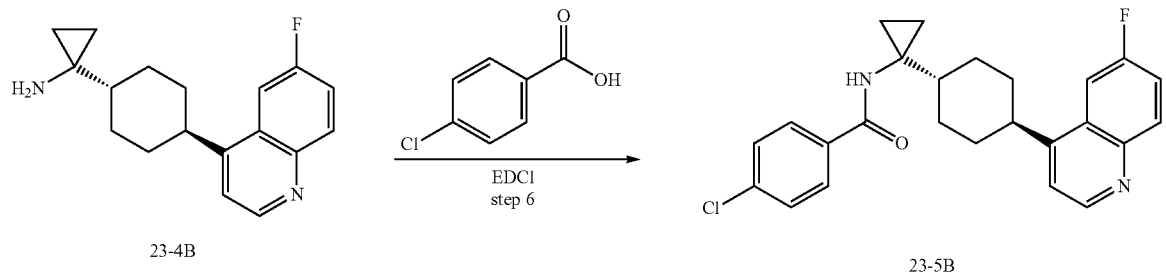

Step 1: Synthesis of 4-cyanocyclohex-1-en-1-yl trifluoromethanesulfonate

Compound 23-1 was prepared from 4-oxocyclohexane-1-carbonitrile using the procedure described in Method 1, step 1.

Step 2:

To a stirred solution of 2.01 g (7.88 mmol) of compound 23-1 in 40 mL of dioxane were added 2.6 g (9.45 mmol) of intermediate 1 and 3.3 g (23.6 mmol) of potassium carbonate in 8 mL of $H_2O$ and 0.6 g (0.79 mmol) of Pd(dppf)$Cl_2$ under nitrogen atmosphere. The mixture was stirred at 100° C. for 1.5 h, and then cooled to room temperature. It was diluted with 200 mL of $H_2O$, and extracted with three 150 mL portions of ethyl acetate. The combined organic extracts were washed with brine, dried over anhydrous $Na_2SO_4$, and filtered. The filtrate was concentrated to afford a residue, which was purified by chromatography on silica gel column eluting with 0 to 50% gradient of ethyl acetate in petroleum ether to give compound 23-2. LC-MS: m/e=253 $[M+H]^+$.

Step 3:

Following the procedure described in Method 1, step 4, compound 23-3 was prepared from compound 23-2. LC-MS: m/e=255 $[M+H]^+$.

Step 4:

To a stirred solution of 0.30 g (1.18 mmol) of compound 23-3 and 0.37 g (1.3 mmol) of Ti(OiPr)$_4$ in 10 mL of DCM was added 0.87 mL (2.60 mmol) of EtMgBr (3 M in $Et_2O$) dropwise at 0° C. under argon atmosphere. The mixture was stirred at room temperature for 2 h under argon atmosphere. To the above mixture was added 0.33 g (2.36 mmol) of $BF_3.Et_2O$ dropwise at room temperature. The mixture was stirred at room temperature for additional 1.5 h, quenched with 3 mL of 1N HCl solution, and then basified to pH 9 with 10% NaOH. The mixture was extracted with two 150 mL portions of DCM; the combined organic extracts were dried over anhydrous $Na_2SO_4$. After filtration, the filtrate was concentrated to afford a residue, which was purified by Prep-TLC eluting with 2% MeOH in DCM to afford compound 23-4A and compound 23-4B. LC-MS for compound 1-4A: m/e=285 $[M+H]^+$. LC-MS for compound 23-4B: m/e=285 $[M+H]^+$.

Step 5:

Following the procedure described in Method 2, step 1, compound 23-5A was prepared from compound 23-4A. LC-MS: m/e=423 $[M+H]^+$.

Step 6:

Following the procedure described in Method 2, step 1, compound 23-5B was prepared from compound 23-4B similarly. LC-MS: m/e=423 $[M+H]^+$.

Method 24

Example 24: Synthesis of N-(4-chlorophenyl)-1-(4-(6-fluoroquinolin-4-yl)cyclohexyl)cyclopropyl-1-carboxamide (Compounds 2-10A and 2-10B)

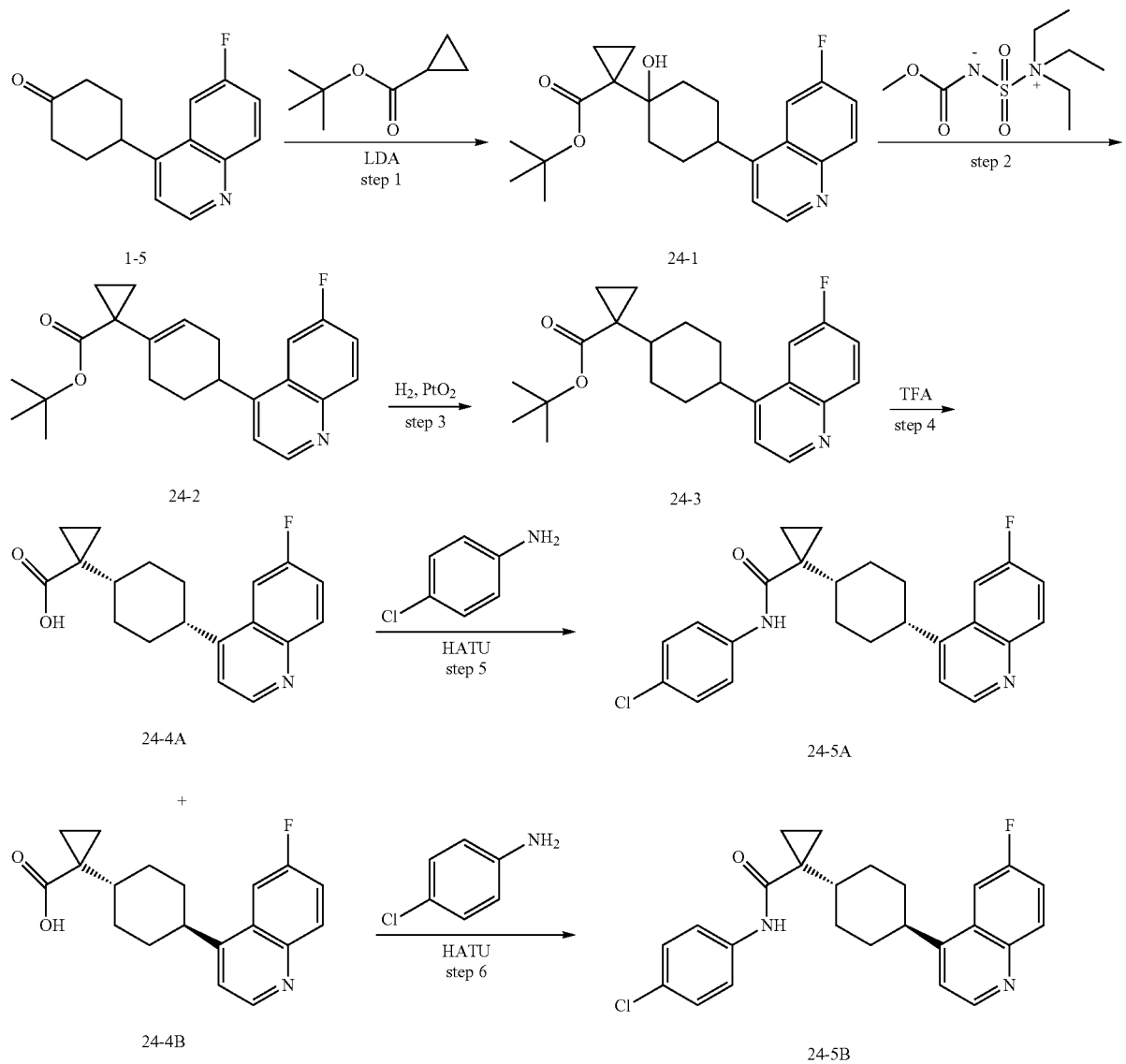

Scheme 24

Step 1

To a stirred solution of 3.2 g (22.6 mmol) of tert-butyl cyclopropanecarboxylate in 15 mL of THF was added 12.44 mL (2 M in THF, 24.9 mmol) of LDA dropwise at −78° C. under argon atmosphere. The mixture was stirred at −78° C. for 1.5 h under argon atmosphere. To the above mixture was added 2.75 g (11.3 mmol) of compound 2-5 in 15 mL of THF dropwise over 15 min at −78° C. The mixture was stirred at −78° C. for additional 5 h, quenched by addition of 30 mL of saturated NH$_4$Cl (aq.) at 0° C., and extracted with three 50 mL portions of ethyl acetate. The combined organic extracts were washed with brine, and dried over anhydrous Na$_2$SO$_4$. After filtration, the filtrate was concentrated under reduced pressure to afford a residue, which was purified by silica gel column chromatography eluting with hexane/EtOAc (20:1) to afford compound 24-1. LC-MS: m/e=386 [M+H]$^+$.

Step 2:

To a stirred solution of 1.3 g (3.5 mmol) of compound 24-1 in 10 mL of toluene was added 1.7 g (7.0 mmol) of (methoxycarbonyl)[(trimethylazaniumyl)sulfonyl]azanide at room temperature. The mixture was stirred at 100° C. overnight under nitrogen atmosphere and then quenched by addition of 7 mL of water at room temperature. The mixture was extracted with four 15 mL portions of ethyl acetate; the combined organic layers were washed with brine and dried over anhydrous Na$_2$SO$_4$. After filtration, the filtrate was concentrated under reduced pressure to afford a residue, which was purified by silica gel column chromatography eluting with 10% EtOAc in hexanes to afford compound 24-2. LC-MS: m/e=368 [M+H]⁺.

Step 3:

To a stirred solution of 0.72 g (1.95 mmol) of compound 24-2 in 8 mL of EtOAc were added 0.72 g (3.2 mmol) of PtO₂ at room temperature. The mixture was stirred at 35° C. for 4 h under hydrogen atmosphere and then filtered. The filter cake was washed with three 5 mL portions of ethyl acetate; the combined filtrates were concentrated under reduced pressure to give crude compound 24-3, which was directly used for the next step without further purification. LC-MS: m/e=370 [M+H]⁺.

Step 4:

To a stirred solution of 0.69 g of crude compound 24-3 in 3.5 mL of DCM was added 3.5 mL of TFA at room temperature. The mixture was stirred at 60° C. overnight and concentrated under reduced pressure to afford a residue, which was purified by Prep-HPLC [Column: XBridge Prep OBD C18 Column 30*150 mm 5 μm; Mobile Phase A: Water (10 mM NH₄HCO₃), Mobile Phase B: CAN; Flow rate: 60 mL/min; Gradient: 24% B to 24% B in 11 min; 220 nm, Detector, 220 nm UV] to give compound 24-4A and isomer 24-4B. LC-MS for 24-4A: m/e=314 [M+H]⁺. LC-MS for 24-4B: m/e=314 [M+H]⁺.

Step 5:

Following the procedure described in Method 1, step 9, compound 24-5A was prepared from compound 24-4A similarly. LC-MS: m/e=423 [M+H]⁺.

Step 6:

Following the procedure described in Method 1, step 9, compound 24-5B was prepared from compound 24-4B similarly. LC-MS: m/e=423 [M+H]⁺.

Method 25

Example 25: Alternative synthesis of N-(4-chlorophenyl)-1-(4-(6-fluoroquinolin-4-yl)cyclohexyl)cyclopropyl-1-carboxamide (Compounds 24-5A and 24-5B)

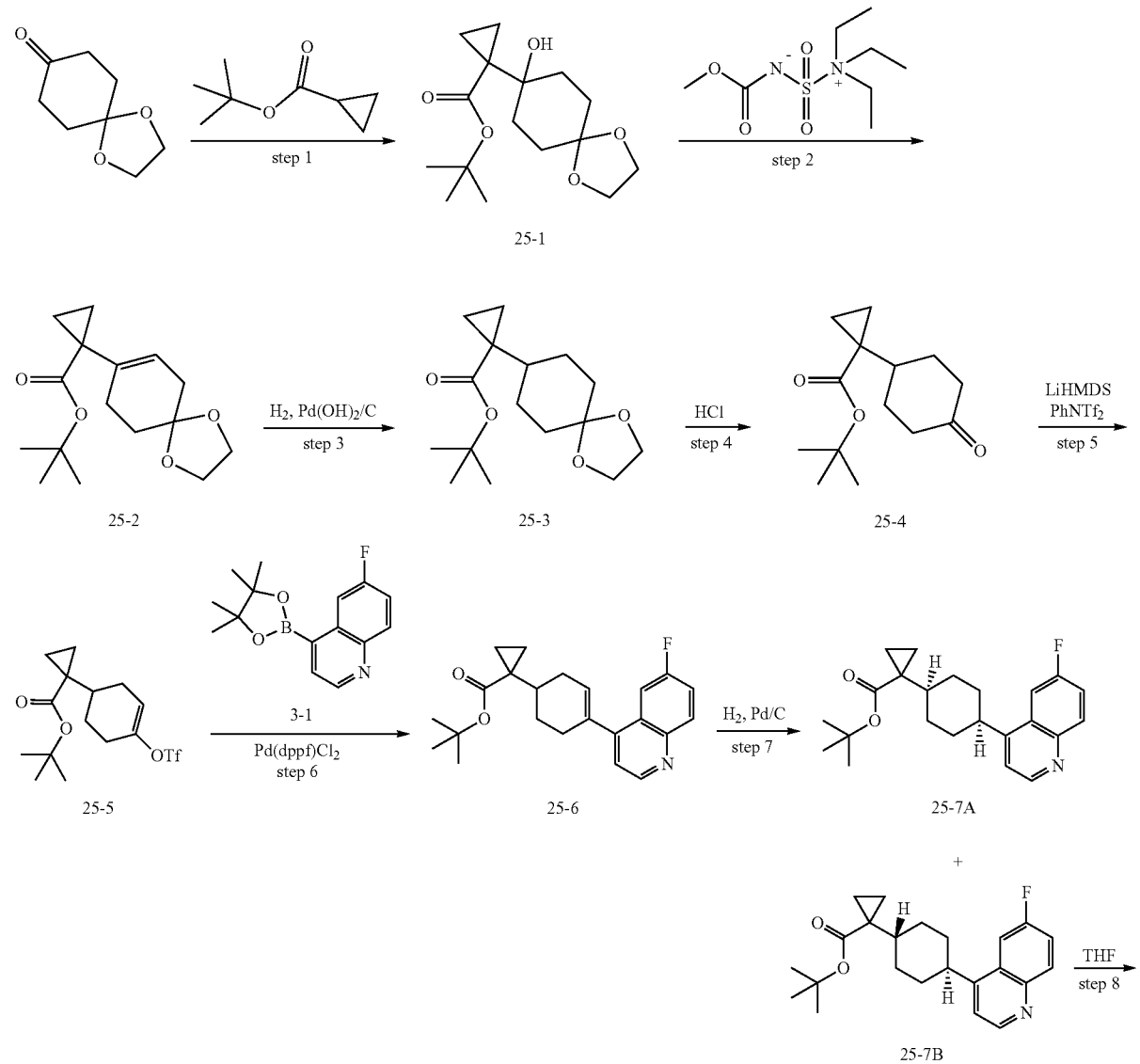

Scheme 25

-continued

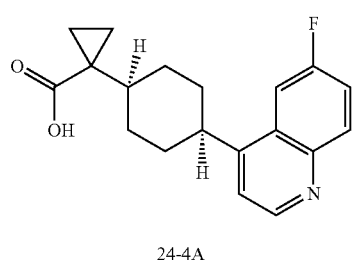

24-4A i. (COCl)$_2$
ii. <image content: 4-chloroaniline> NH$_2$ step 9

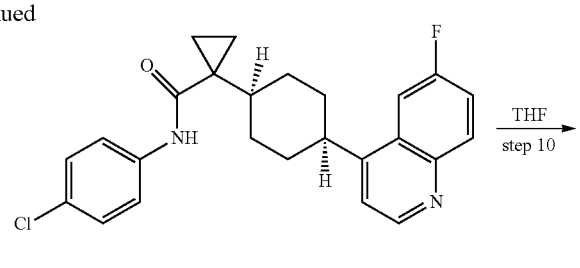

24-5A

THF
step 10

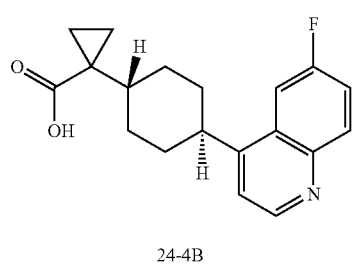

24-4B i. (COCl)$_2$
ii. <image content: 4-chloroaniline> NH$_2$ step 11

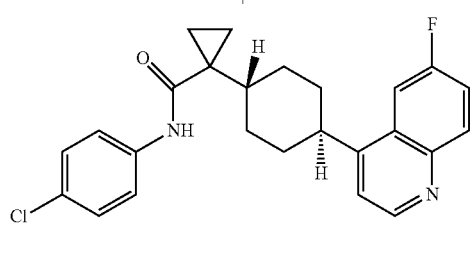

24-5B

Step 1

To a cooled solution of 3.0 mL (21.2 mmol) of diisopropylamine in 30 mL of THF was added a solution of 7.8 mL of n-BuLi (2.5 M in hexane) dropwise at 0° C. under Ar atmosphere. The mixture was stirred at 0° C. for 1 h. To the above mixture was added a solution of 2.5 g (17.6 mmol) of tert-butyl cyclopropanecarboxylate in 10 mL of THF dropwise over 10 min at −78° C. The mixture was stirred for additional 1 h at −78° C. under Ar atmosphere. To the above mixture was added a solution of 4.1 g (26.3 mmol) of 1,4-dioxaspiro[4.5]decan-8-one in 10 mL of THF dropwise at −78° C. The mixture was stirred for additional 40 min at −78° C. for additional 40 min and at RT overnight. The reaction was quenched by addition of 30 mL of saturated NH$_4$Cl at 0° C. and extracted with three 20 mL portions of ethyl acetate. The combined organic layers were washed with brine and dried over anhydrous Na$_2$SO$_4$. After filtration, the filtrate was concentrated to give a residue, which was purified by silica gel column chromatography eluting with 10% ethyl acetate in petroleum ether to give compound 25-1. LC-MS: m/e=225 [M−74+H]$^+$.

Step 2:

Compound 25-2 was prepared from compound 25-1 following the procedure describe in Method 24, step 2. LC-MS: m/e=298 [M+H$_2$O]$^+$.

Step 3:

Compound 25-3 was prepared from compound 25-2 following the procedure describe in Method 14, step 6. LC-MS: m/e=227 [M−56+H]$^+$.

Step 4:

To a stirred solution of 300 mg of compound 25-3 in 3 mL of t-BuOH was added 2 mL 6 N HCl dropwise at RT. The mixture was stirred at RT for 2 h and diluted with 3 mL of H$_2$O. The mixture was extracted with three 10 mL portions of DCM. The combined organic layers were washed with brine and dried over anhydrous Na$_2$SO$_4$. After filtration, the filtrate was concentrated to give a residue, which was purified by silica gel column chromatography eluting with PE/EA (150:1) to afford compound 25-4. LC-MS: m/e=183 [M−56+H]$^+$.

Step 5:

Compound 25-5 was prepared from compound 25-4 following the procedure describe in Method 1, step 1. LC-MS: m/e=297 [M−74+H]$^+$.

Step 6:

Compound 25-6 was prepared from compound 25-5 following the procedure describe in Method 1, step 2. LC-MS: m/e=368 [M+H]$^+$.

Step 7:

Following the procedure describe in Method 1, step 4, compound 25-6 was converted to compound 26-7A and compound 25-7B. LC-MS: m/e=370 [M+H]$^+$.

Step 8:

Following the procedure describe in Method 24, step 4, compound 25-7A was converted to compound 24-4A, LC-MS: m/e=314 [M+H]$^+$.

Step 9:

Following the procedure describe in Method 25, steps 7 and 8, compound 24-4A was converted to compound 24-5A, LC-MS: m/e=423 [M+H]$^+$.

Step 10:

Following the procedure describe in Method 24, step 4, compound 25-7B was converted to compound 24-4B, LC-MS: m/e=314 [M+H]$^+$.

Step 11

Following the procedure describe in Method 25, steps 7 and 8, compound 24-4B was converted to compound 24-5B, LC-MS: m/e=423 [M+H]$^+$.

Method 26

Example 26: Synthesis of N-(4-chlorophenyl)-1-[1-(6-fluoroquinolin-4-yl)piperidin-4-yl]cyclopropane-1-carboxamide (Compound 26-8)

Scheme 26

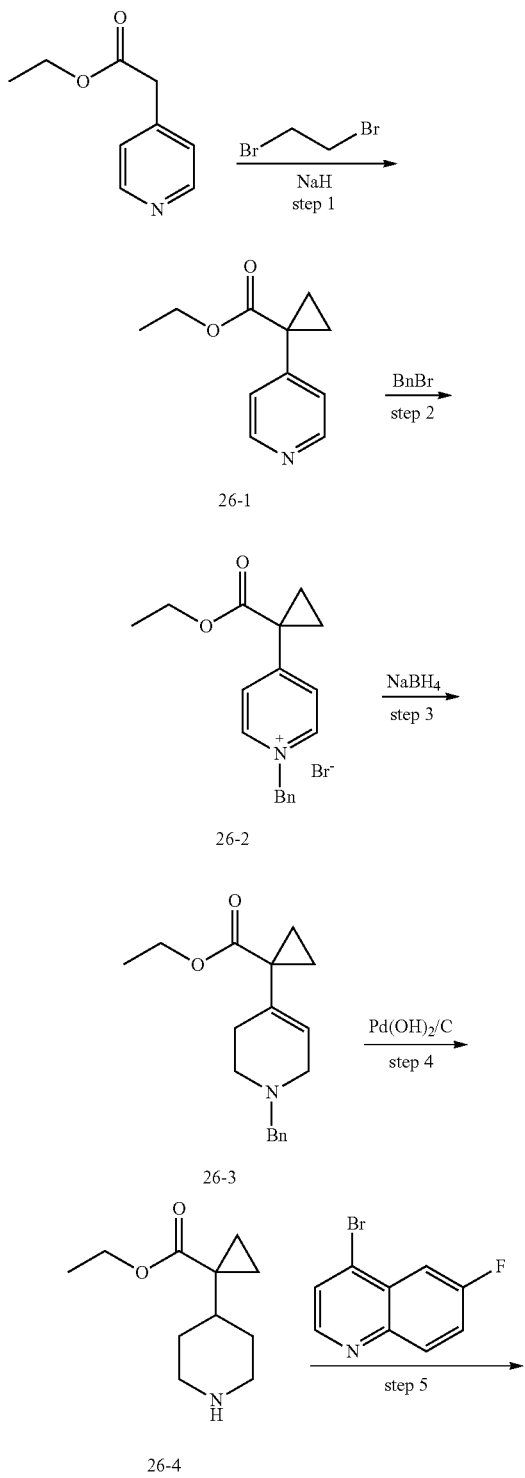

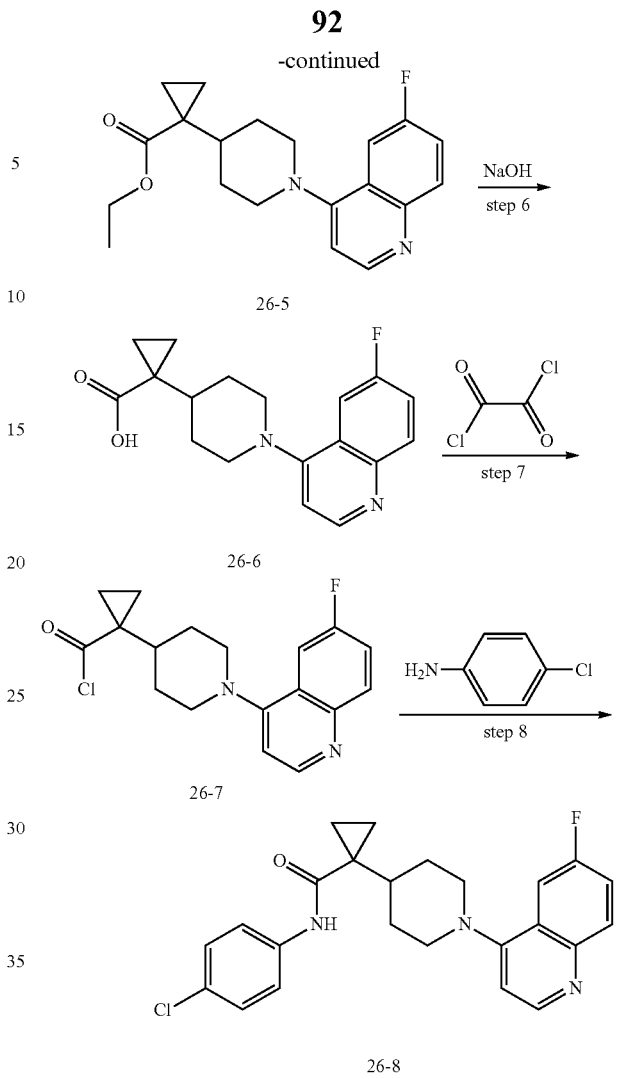

Step 1

To a solution of 2.0 g (12.1 mmol) of ethyl 2-(pyridin-4-yl)acetate in 30 mL of THF were added 6 mL of DMF, 4.5 g (24.2 mmol) of 1,2-dibromoethane and 0.90 g (36.3 mmol) of NaH. The solution was stirred at 35° C. for 2 h and quenched by addition of saturated NH$_4$Cl; the solution was extracted with four 50 mL portions of ethyl acetate. The organic layers were combined and dried over anhydrous Na$_2$SO$_4$. It was filtered and the filtrate was concentrated to afford compound 26-1. LC-MS: m/e=192 [M+H]$^+$.

Step 2:

To a solution of 2.0 g (10.5 mmol) of compound 26-1 in 30 mL of ACN was added 2.7 g (15.7 mmol) of BnBr. The solution was stirred at 40° C. for 2 h and concentrated. Addition of EtOAc resulted in compound 26-2. LC-MS: m/e=282 [M+H]$^+$.

Step 3:

To a solution of 4.0 g (11 mmol) of compound 26-2 in 50 mL of methanol was added 0.6 g (16.6 mmol) of sodium borohydride. The solution was stirred at RT for 20 min and quenched by addition of 80 mL of water. It was extracted with three 50 mL portions of ethyl acetate. The organic layers were combined and concentrated to give a residue, which was purified by Prep-HPLC (Column, C18 silica gel; mobile phase, ACN/H$_2$O 40%; Detector, UV 200 nm) to give compound 26-3. LC-MS: m/e=286 [M+H]$^+$.

Step 4:

Compound 26-4 was prepared from compound 26-3 using the procedure described in method 14, step 6. LC-MS: m/e=198 [M+H]+.

Step 5:

Compound 26-5 was prepared from compound 26-4 using the procedure described in method 22, step 1. LC-MS: m/e=343 [M+H]+.

Step 6:

Compound 26-6 was prepared from compound 26-5 using the procedure described in Method 1, step 8. LC-MS: m/e=315 [M+H]+.

Step 7:

To a solution of compound 26-6 (100 mg, 0.32 mmol) in DCM (8 mL) was added oxalic dichloride (121.1 mg, 0.95 mmol) and DMF (0.1 mL, 1.29 mmol). The resulting solution was stirred for 30 min at room temperature. The resulting mixture was concentrated under vacuum to afford compound 26-7.

Step 8:

To a solution of 100 mg (0.30 mmol) of compound 26-7 in 5 mL of DCE were added 185 mg (0.90 mmol) of 2,6-di-tert-butyl-4-methylpyridine and 58 mg (0.45 mmol) of 4-chloroaniline. The solution was stirred at RT for 30 min and quenched by addition of 30 mL of water. It was extracted with three 20 mL portions of ethyl acetate; the combined organic layers were concentrated to give a residue, which was purified by Prep-HPLC (Column, XBridge Prep OBD C18 Column, 30×150 mm 5 μm; mobile phase, Water (10 mM NH4HCO3) and ACN (47% Phase B up to 60% in 8 min); Detector, UV) to give compound 26-8. LC-MS: m/e=424 [M+H]+.

Method 27

Example 27: Synthesis of 4-chloro-N-[1-[1-(6-fluoroquinolin-4-yl)piperidin-4-yl]cyclopropyl]benzamide (Compound 27-3)

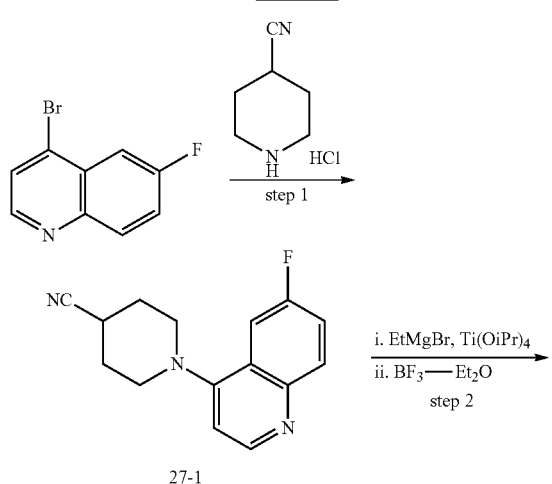

Step 1

Compound 27-1 was prepared from 4-bromo-6-fluoroquinoline following the procedure described in Method 12, step 1. LC-MS: m/e=256 [M+H]+.

Step 2:

Compound 27-2 was prepared from compound 27-1 following the procedure described in Method 23, step 4. LC-MS: m/e=286 [M+H]+.

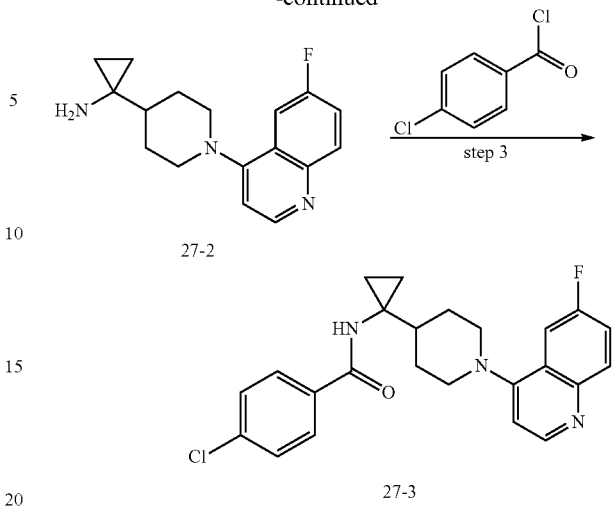

Step 3:

Compound 27-3 was prepared from compound 27-2 following the procedure described in Method 17, step 4. LC-MS: m/e=424 [M+H]+.

Method 28

Example 28: Synthesis of 1-(4-(1,6-naphthyridin-4-yl)cyclohexyl)-N-(4-chlorophenyl)cyclopropane-1-carboxamide (Compound 28-5)

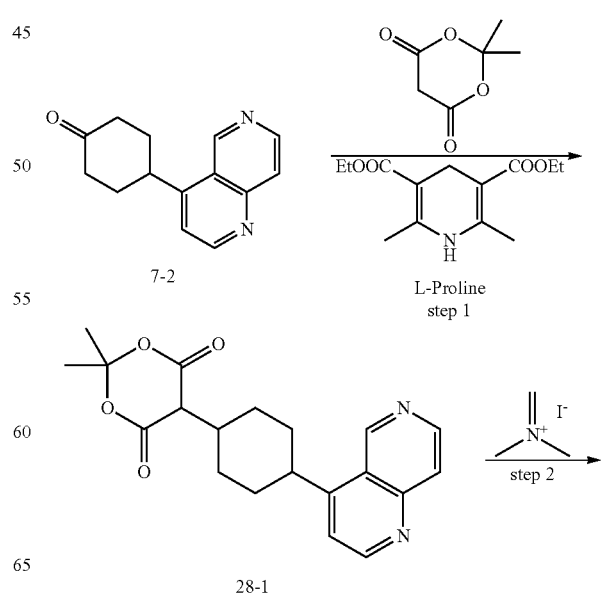

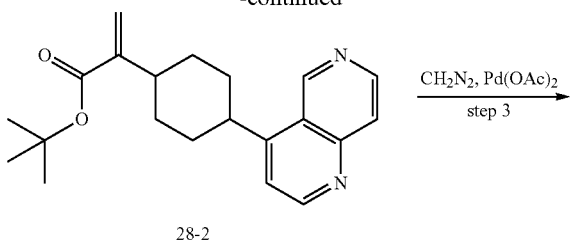

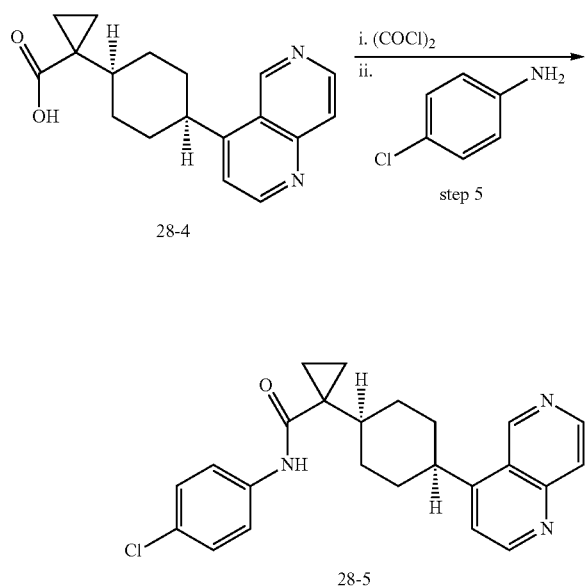

Step 1
To a stirred solution of 2.0 g (8.8 mmol) of compound 7-2 and 1.53 g (10.6 mmol) of 2,2-dimethyl-1,3-dioxane-4,6-dione in 30 mL THF was added 0.40 g (3.5 mmol) of L-Proline at RT. The mixture was stirred at 30° C. for 3 h under argon atmosphere. To the above mixture was added 0.22 g (8.84 mmol) of 3,5-diethyl 2,6-dimethyl-1,4-dihydropyridine-3,5-dicarboxylate at 30° C. The mixture was stirred at 30° C. overnight and concentrated to give a residue, which was purified by silica gel column chromatography eluting with 0 to 10% gradient of MeOH in ethyl acetate to afford compound 28-1. LC-MS: m/e=355 [M+H]$^+$.

Step 2:
To a stirred solution of 1.7 g (4.8 mmol) of compound 28-1 in 110 mL t-BuOH was added 2.66 g (14.4 mmol) of dimethyl(methylidene)azanium iodide at RT. The mixture was stirred overnight at 70° C. under argon atmosphere and then concentrated. The residue was purified by silica gel column chromatography eluting with 0 to 20% gradient of ethyl acetate in petroleum ether to afford compound 28-2. LC-MS: m/e=339 [M+H]$^+$.

Step 3:
To a stirred solution of 680.0 mg (2.0 mmol) of compound 28-2 and 90 mg (0.40 mmol) of palladium(II) acetate in THF was added 845 mg (20.0 mmol) of diazomethane dropwise at 0° C. under nitrogen atmosphere. The mixture was stirred at RT for 1 h under nitrogen atmosphere and then concentrated. The residue was purified by Prep-HPLC (Column, XBridge Shield RP18 OBD Column, 5 μm, 19*150 mm; mobile phase A: Water (10 mM NH$_4$HCO$_3$+0.1% NH$_3$.H$_2$O) and mobile phase B: ACN, flow rate: 25 ml/min; Gradient: 48% B to 56% B in 11 min; 220 nm) to obtain compound 28-3. LC-MS: m/e=353 [M+H]$^+$.

Step 4:
To a stirred solution of 40 mg (0.11 mmol) of compound 28-3 in 2.0 mL DCM was added 2 mL 4 N HCl in dioxane at RT. The mixture was stirred at RT overnight and then concentrated under reduced pressure to obtain product 28-4. LC-MS: m/e=297 [M+H]$^+$.

Step 5:
Compound 28-5 was prepared from compound 28-4 following the procedures described in Method 25, steps 7 and 8. LC-MS: m/e=406 [M+H]$^+$.

Method 29

Example 29: Synthesis of 1-(4-(1,6-naphthyridin-4-yl)cyclohexyl)-N-(4-chlorophenyl) cyclopropane-1-carboxamide (29-6)

Scheme 29

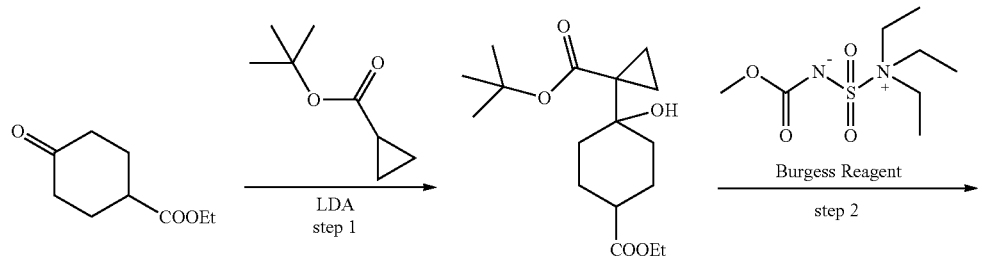

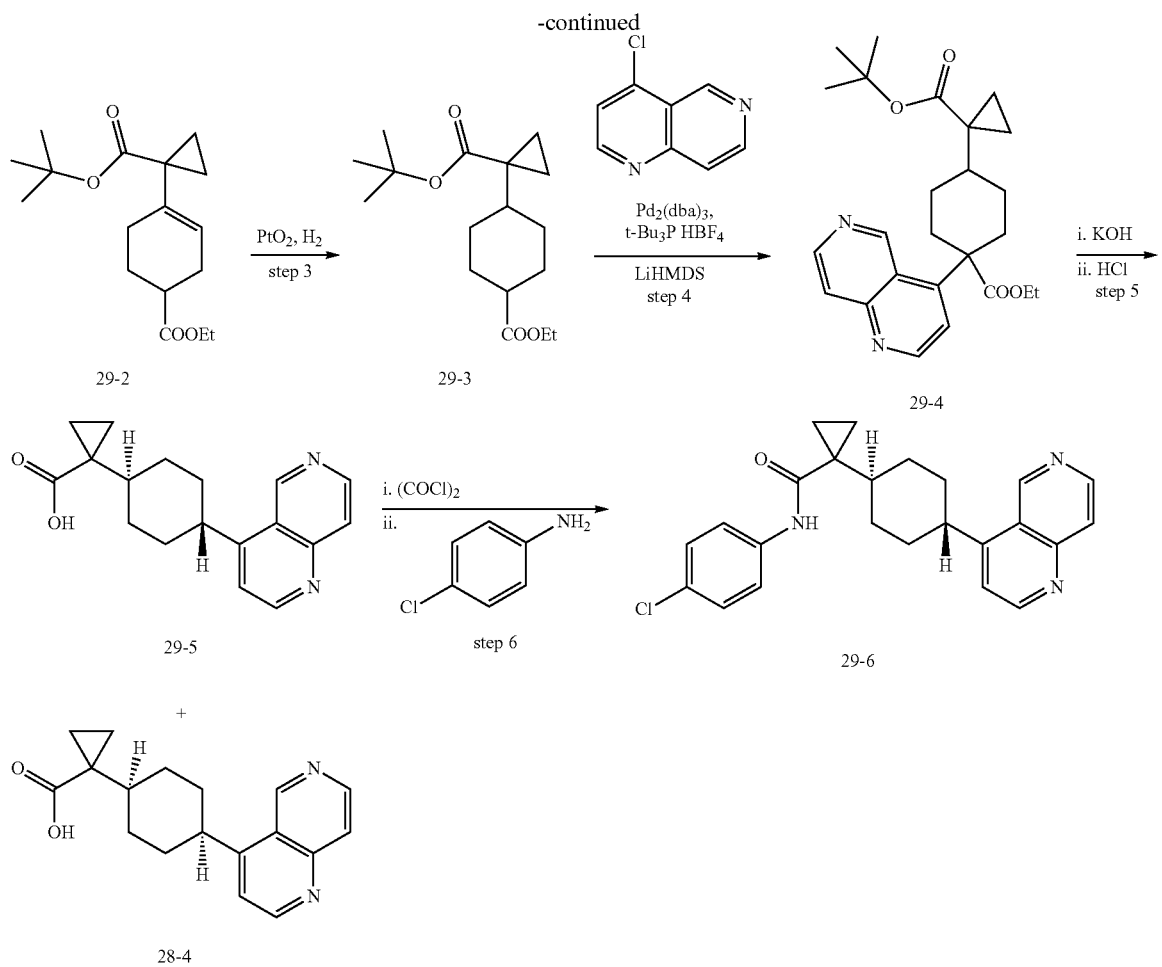

Step 1

Compound 29-1 was prepared from ethyl 4-oxocyclohexane-1-carboxylate following the procedure described in Method 24, step 1. LC-MS: m/e=239 [M-tBuO+H]$^+$.

Step 2:

Compound 29-2 was prepared from compound 29-1 following the procedure described in Method 24, step 2. LC-MS: m/e=239 [M-tBu+H]$^+$.

Step 3:

Compound 29-3 was prepared from compound 29-2 following the procedure described in Method 24, step 3. LC-MS: m/e=241 [M-tBu+H]$^+$.

Step 4:

Compound 29-4 was prepared from compound 29-3 following the procedure described in Method 7, step 1. LC-MS: m/e=425 [M+H]$^+$.

Step 5:

Following similar procedures described in Method 7, step 2, using KOH instead of NaOH, compound 29-4 was converted to a mixture of compound 29-5 and compound 28-4. LC-MS: m/e=297 [M+H]$^+$.

Step 6:

Following similar procedures described in Method 25, steps 7 and 8, compound 29-5 was converted to a mixture of compound 29-6. LC-MS: m/e=406 [M+H]$^+$.

Synthesis of Intermediates
1. Synthesis of Intermediate 1

Scheme 30

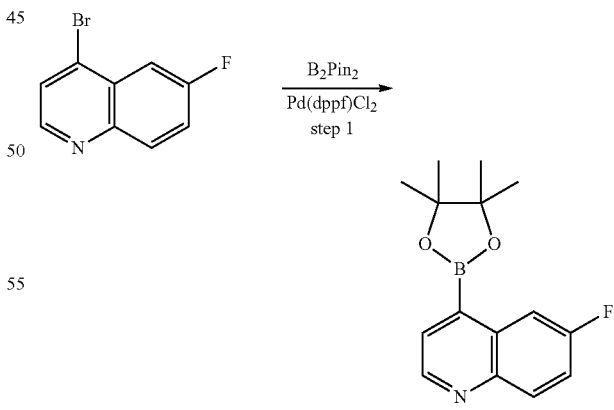

Step 1

To a solution of 5.0 g (22.1 mmol) of 4-bromo-6-fluoroquinoline and 6.5 g (66.2 mmol) of KOAc in 200 mL of dioxane were added 13.5 g (53.2 mmol) of 4,4,5,5-tetramethyl-2-(tetramethyl-1,3,2-dioxaborolan-2-yl)-1,3,2-dioxaborolane and 0.8 g (1.09 mmol) of Pd(dppf)Cl$_2$ at room temperature. The mixture was stirred at 90° C. for 2.5 h under nitrogen atmosphere and then concentrated under reduced pressure to afford a residue, which was purified by chromatography on silica gel column eluting with 0 to 30% gradient of ethyl acetate in petroleum ether to afford intermediate 1. LC-MS: m/e=274 [M+H]$^+$.

LC-MS Conditions Used in the Experimental Procedures Described Above:

Condition A: Shimadzu LC20AD/LCMS2020; Column: Shim-pack XR-ODS (50*3.0 mm) 2.2 μm; Mobile phase: A: 0.05% trifluoroacetic acid in water, B: 0.05% trifluoroacetic acid in acetonitrile; Gradient: 95:5 to 0:100 (A:B) over 1.1 min, 0:100 (A:B) for 0.55 min, Flow Rate: 1.2 mL/min; UV detection: 190-400 nm.

Condition B: Shimadzu LC30AD/LCMS2020, Column: COTRECS-C18 (50*2.1 mm) 2.7 μm; Mobile phase: A: 0.1% formic acid in water, B: 0.1% formic acid in acetonitrile; Gradient: 90:10 to 0:100 (A:B) over 1.1 min, 0:100 (A:B) for 0.50 min, Flow Rate: 1.0 mL/min. UV detection: 190-400 nm.

Condition C: Shimadzu LC30AD/LCMS2020, Column: Ascentis Express (50*3.0 mm) 2.7 μm; Mobile phase: A: 0.05% trifluoroacetic acid in water, B: 0.05% trifluoroacetic acid in acetonitrile; Gradient: 95:5 to 0:100 (A:B) over 1.2 min, 0:100 (A:B) for 0.50 min, Flow Rate: 1.5 mL/min. UV detection: 190-400 nm.

Condition D: Shimadzu LC20ADXR/LCMS2020, Column: Poroshell HPH-C18 (50*3.0 mm) 2.7 μm; Mobile phase: A: 5 mM ammonium bicarbonate in water, B: acetonitrile; Gradient: 90:10 to 5:95 (A:B) over 1.2 min, 5:95 (A:B) for 0.50 min, Flow Rate: 1.2 mL/min. UV detection: 190-400 nm.

Condition E: Shimadzu LC20ADXR/LCMS2020, Column: Kinextex EVO C18 (50*3.0 mm) 2.6 μm; Mobile phase: A: 5 mM ammonium bicarbonate in water, B: acetonitrile; Gradient: 90:10 to 5:95 (A:B) over 1.2 min, 5:95 (A:B) for 0.50 min, Flow Rate: 1.2 mL/min. UV detection: 190-400 nm.

Condition F: Shimadzu LC20ADXR/LCMS2020, Column: Kinextex XB-C18 (50*3.0 mm) 2.6 μm; Mobile phase: A: 0.1% formic acid in water, B: 0.1% formic acid in acetonitrile; Gradient: 90:10 to 0:100 (A:B) over 1.1 min, 0:100 (A:B) for 0.50 min, Flow Rate: 1.5 mL/min. UV detection: 190-400 nm.

Condition G: Shimadzu LC20ADXR/LCMS2020, Column: Kinetex EVO C18, 3.0*50 mm, 2.6 μm; Mobile Phase A: 0.04% NH$_4$OH, Mobile Phase B: ACN; Gradient: 90:10 to 5:95(A:B) in 2.1 min, 5:95 (A:B) for 0.6 min, Flow Rate: 1.2 mL/min. UV detection: 254 nm Condition H: Shimadzu LC20ADXR/LCMS2020, Column: Kinetex EVO C18, 3.0*50 mm, 2.6 μm; Mobile Phase A: 0.04% NH$_4$OH, Mobile Phase B: ACN; Gradient: 90:10 to 5:95 (A:B) in 2.1 min, 5:95 (A:B) for 0.6 min, Flow rate: 1.2 mL/min. UV detection: 254 nm Condition I: Shimadzu LC20ADXR/LCMS2020, COR-TECS C18+100 A (50*2.1 mm) 2.7 μm; Mobile phase: A: 0.1% FA in water, B: 0.1% FA in acetonitrile; Gradient. Column: 90:10 to 0:100 (A:B) over 2 min, 0:100 (A:B) for 0.6 min. Flow Rate: 1.2 mL/min. UV detection: 190-400 nm Condition J: Shimadzu LC20ADXR/LCMS2020, Column: Poroshell HPLC18 (50*3.0 mm) 2.7 μm; Mobile phase: A: 0.04% NH$_4$OH in water, B: acetonitrile; Gradient: 90:10 to 30:70 (A:B) over 3.6 min, 30:70 to 5:95 (A:B) for 0.4 min, 5:95 (A:B) for 0.8 min. Flow Rate: 1.2 mL/min. UV detection: 190-400 nm.

Assays

Protocols that May be Used to Determine the Recited Potency for the Compounds of the Disclosure are Described Below.

Hela cells were seeded into 96-well cell culture plates at 10 K cells per well. The cell plates were allowed to stand inside a biological hood at ambient temperature for 20 minutes and incubate in an incubator at ambient temperature overnight. The compounds were serially diluted (half-log) in 100% DMSO for descending doses. Solutions each containing 2 μL of a compound or DMSO (for a control well) were transferred to a 96-well plate and the plate was sealed. A high control and a low control were used for the assay. High control is Hela cells with IFNγ treatment (final DMSO at 0.1%). Low control is Hela cells without IFNγ treatment (final DMSO at 0.1%). The treatment medium was prepared as the following: a) for low control wells: DMEM medium containing 10% FBS, 1% PS and 200 μM Trp; b) for high control wells and compound test wells: DMEM medium containing 10% FBS, 1% PS, 200 μM Trp and 25 ng/ml IFNγ. 78 μL of freshly prepared treatment medium was added to and mixed with the compound in each well of the plate.

An 8 μL of the diluted compound solutions were then transferred into the wells of another 96-well plate with each well containing 192 μL of treatment medium. The cell culture medium was discarded and 100 μL of treatment medium each containing a compound or DMSO was added to each well of the cell plates. The cell plates were incubated in an incubator at ambient temperature for 48 hours. After incubation, 50 μL of supernatant from each well was transferred to a 96-well assay plate. 200 μL of acetonitrile was added to each well of the assay plate and mixed thoroughly. The assay plates were centrifuged at 4000 rpm at 4° C. for 20 minutes. From each well, a 40 μL of supernatant was transferred to another 96-well plate. To each well of the final plate was added 360 μL of water and mixed thoroughly. The sample in each well was analyzed on RapidFire/MS/MS for N-formylkynurenine concentration and IC$_{50}$ was calculated using conventional curve-fitting method. The testing results for representative compounds are summarized in Table 8, wherein A represents the IC$_{50}$ value of <100 nM; B represents the IC$_{50}$ value of 100-1000 nM; and C represents the IC$_{50}$ value of >1000 nM. IC$_{50}$ values were calculated using Prism 5 (GraphPad).

TABLE 8

Human IDO Inhibitory Activity of Representative Examples

| Compound | h-IDO (HeLa) IC$_{50}$ (nM) | Compound | h-IDO (HeLa) IC$_{50}$ (nM) |
|---|---|---|---|
| INCB 024360* | A (16.4 nM) | | |
| 1-9 | A | 1-10 | A |
| 1-11 | C | 1-12 | A |
| 1-13 | B | 1-14 | A |
| 1-15 | B | 1-16 | B |
| 1-17 | C | 1-18 | C |
| 1-19 | A | 1-20 | C |
| 1-21 | C | 1-22 | B |
| 1-23 | A | 2-1 | A |
| 2-2 | C | 2-3 | B |
| 2-4 | B | 2-5 | A |
| 2-6 | A | 3-2 | C |
| 3-3 | B | 4-4 | A |
| 4-5 | A | 4-6 | A |
| 4-7 | A | 4-8 | A |
| 4-9 | A | 5-4 | B |

TABLE 8-continued

Human IDO Inhibitory Activity of Representative Examples

| Compound | h-IDO (HeLa) IC$_{50}$ (nM) | Compound | h-IDO (HeLa) IC$_{50}$ (nM) |
|---|---|---|---|
| 6-9 | A | 7-6 | A |
| 7-7 | C | 8-4A | A |
| 8-4B | A | 8-4C | A |
| 8-4D | B | 8-4E | B |
| 8-4F | A | 9-4 | A |
| 9-5 | C | 10-4 | B |
| 11-5 | A | 11-6 | A |
| 12-6 | A | 12-7 | C |
| 13-3 | B | 14-7 | C |
| 15-3 | C | 16-7 | A |
| 16-8 | C | 17-6 | A |
| 17-7 | B | 17-8 | A |
| 17-9 | B | 18-5 | A |
| 19-3 | B | 20-8 | A |
| 20-9 | C | 21-4 | A |
| 21-5 | C | 22-5 | C |
| 23-5A | A | 23-5B | A |
| 24-5A | A | 24-5B | A |
| 26-8 | A | 27-3 | B |
| 28-5 | A | 29-6 | A |

*INCB 024360 is a reference compound for comparison: CAS No. [1240669-58-8].

Unless otherwise indicated, all numbers expressing quantities of ingredients, properties such as molecular weight, reaction conditions, and etc. used in herein are to be understood as being modified in all instances by the term "about." Each numerical parameter should at least be construed in light of the number of reported significant digits and by applying ordinary rounding techniques. Accordingly, unless indicated to the contrary, the numerical parameters may be modified according to the desired properties sought to be achieved, and should, therefore, be considered as part of the disclosure. At the very least, the examples shown herein are for illustration only, not as an attempt to limit the scope of the disclosure.

The terms "a," "an," "the" and similar referents used in the context of describing embodiments of the present disclosure (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein is intended merely to better illustrate embodiments of the present disclosure and does not pose a limitation on the scope of any claim. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments are described herein, including the best mode known to the inventors for carrying out the embodiments. Of course, variations on these described embodiments will become apparent to those of ordinary skill in the art upon reading the foregoing description. The inventor expects skilled artisans to employ such variations as appropriate, and the inventors intend for the embodiments of the present disclosure to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by a formula:

E-D-L-A or a pharmaceutically acceptable salt thereof;
wherein A is an optionally substituted phenyl, optionally substituted pyridinyl, or optionally substituted piperidinyl which attaches at a ring atom;
D is optionally substituted spiro[2.5]octanyl or optionally substituted 6-azaspiro[2.5]octanyl, which attaches at the 1 and 6 positions; spiro[3.5]nonanyl or 7-azaspiro[3.5]nonanyl, which attaches at the 1 and 7 or 2 and 7 positions; spiro[4.5]decanyl or 8-azaspiro[4.5]decanyl, which attaches at the 1 and 8 positions, (1$\lambda^3$-cyclopropyl)-4$\lambda^3$-cyclohexane, or 4-(1$\lambda^3$-cyclopropyl)-1$\lambda^3$-piperidine;
E is optionally substituted $C_{10}$ aryl or optionally substituted 10-membered $C_{4-9}$ heteroaryl; and
L is $(CH_2)_{0-1}$—NHC(O)—, $(CH_2)_{0-1}$—C(O)NH—, or C(O), wherein a C atom or an N atom of L directly attaches to D at position 1, or at position 1 or 2 when D is spiro[3.5]nonanyl or 7-azaspiro[3.5]nonanyl.

2. The compound of claim 1, wherein A is optionally substituted phenyl.

3. The compound of claim 1, wherein L is $(CH_2)_{0-1}$—NHC(O)— or $(CH_2)_{0-1}$—C(O)NH—.

4. The compound of claim 3, further represented by a formula:

E-D-NHC(O)-A.

5. The compound of claim 3, further represented by a formula:

E-D-C(O)NH-A.

6. The compound of claim 1, wherein D is optionally substituted spiro[2.5]octanyl.

7. The compound of claim 1, wherein D is optionally substituted 6-azaspiro[2.5]octanyl.

8. The compound of claim 1, wherein D is optionally substituted spiro[3,5]nonanyl, which attaches at the 1 or 2 position.

9. The compound of claim 1, wherein D is optionally substituted 7-azaspiro[3,5]nonanyl, which attaches at the 1 or 2 position.

10. The compound of claim 1, wherein E is optionally substituted quinolin-4-yl.

11. The compound of claim 1, wherein E is optionally substituted 1,6-naphthyridin-4-yl.

12. The compound of claim 1, further represented by a formula:

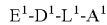

E$^1$-D$^1$-L$^1$-A$^1$ or a pharmaceutically acceptable salt thereof;
wherein A$^1$ is optionally substituted phenyl, optionally substituted pyridinyl, or optionally substituted piperidinyl which attaches at a ring atom;
D$^1$ is optionally substituted (1λ$^3$-cyclopropyl)-4λ$^3$-cyclohexane, or 4-(1λ$^3$-cyclopropyl)-1λ$^3$-piperidine;
E$^1$ is optionally substituted C$_{10}$ aryl or optionally substituted 10-membered C$_{4-9}$ heteroaryl; and
L$^1$ is —C(O)—NH— or —NH—C(O)—, wherein L$^1$ is directly attached to the cyclopropyl ring of D$^1$.

13. The compound of claim 12, wherein A$^1$ is an optionally substituted phenyl.

14. The compound of claim 12, further represented by a formula:

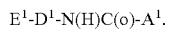

E$^1$-D$^1$-N(H)C(o)-A$^1$.

15. The compound of claim 12, further represented by a formula:

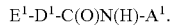

E$^1$-D$^1$-C(O)N(H)-A$^1$.

16. The compound of claim 12, wherein E$^1$ is optionally substituted quinolin-4-yl.

17. The compound of claim 12, wherein E$^1$ is optionally substituted 1,6-naphthyridin-4-yl.

18. A compound, wherein the compound is: optionally substituted (1S,3s,6R)—N-phenyl-6 (quinolin-4-yl)spiro[2.5]octane-1-carboxamide (C-1-9), (1S,3s,6R)—N-phenyl-6-(quinolin-4 yl)spiro[2.5]octane-1-carboxamide (C-1-10), (1R,3s,6S)—N-phenyl-6-(quinolin-4-yl)spiro[2.5]octane-1-carboxamide (C-1-11), (1S,3s,6R)—N-phenyl-6-(quinolin-4-yl)spiro[2.5]octane-1-carboxamide (C-1-12), (1S,3s,6R)—N-phenyl-6-(quinolin-4-yl)spiro[2.5]octane-1-carboxamide (C-1-13), (1S,3s,6R)—N-phenyl-6-(quinolin-4-yl)spiro[2.5]octane-1-carboxamide (C-1-14), (1S,3s,6R)—N-phenyl-6-(quinolin-4-yl)spiro[2.5]octane-1-carboxamide (C-1-15), (1S,3s,6R)—N-phenyl-6-(quinolin-4-yl)spiro[2.5]octane-1-carboxamide (C-16), (1S,3s,6R)—N-phenyl-6-(quinolin-4-yl)spiro[2.5]octane-1-carboxamide (C-1-17), (1S,3s,6R)—N-(piperidin-1-yl)-6-(quinolin-4-yl)-spiro[2.5]octane-1-carboxamide (C-1-18), (1S,3s,6R)—N-phenyl-6-(quinolin-4-yl)spiro[2.5]octane-1-carboxamide (C-1-19), piperidin-1-yl((1S,3s,6R)-6-(quinolin-4-yl)-spiro[2.5]octan-1-yl)methanone (C-1-20), (1S,3s,6R)—N-benzyl-6-(quinolin-4-yl)-spiro[2.5]octane-1-carboxamide (C-1-21), (1S,3s,6R)—N-phenyl-6-(quinolin-4-yl)spiro[2.5]octane-1-carboxamide (C-1-22), (1S,3s,6R)—N-(pyridin-3-yl)-6-(quinolin-4-yl)-spiro[2.5]octane-1-carboxamide (C-1-23), (1S,3s,6R)—N-phenyl-6-(quinolin-4-yl)spiro[2.5]octane-1-carboxamide (C-2-1), (1S,3s,6R)—N-phenyl-6-(quinolin-4-yl)spiro[2.5]octane-1-carboxamide (C-2-2), (1S,3s,6R)—N-(pyridin-2-yl)-6-(quinolin-4-yl)-spiro[2.5]octane-1-carboxamide (C-2-3), (1S,3s,6R)—N-phenyl-6-(quinolin-4-yl)spiro[2.5]octane-1-carboxamide (C-2-4), (1S,3s,6R)—N-phenyl-6-(quinolin-4-yl)spiro[2.5]octane-1-carboxamide (C-2-5), (1S,3s,6R)—N-(pyridin-2-yl)-6-(quinolin-4-yl)spiro[2.5]octane-1-carboxamide (C-2-6), (1S,3s,6R)—N-(pyridin-2-yl)-6-(quinolin-4-yl)spiro[2.5]octane-1-carboxamide (C-3-2), (1S,3s,6R)—N-(pyridin-2-yl)-6-(quinolin-4-yl)spiro[2.5]octane-1-carboxamide (C-3-3), (1S,3s,6R)—N-phenyl-6-(quinolin-4-yl)spiro[2.5]octane-1-carboxamide (C-4-4), (1S,3s,6R)—N-phenyl-6-(quinolin-4-yl)-spiro[2.5]octane-1-carboxamide (C-4-5), (1S,3s,6R)—N-phenyl-6-(quinolin-4-yl)-spiro[2.5]octane-1-carboxamide (C-4-6), (1S,3s,6R)—N-phenyl-6-(quinolin-4-yl)-spiro[2.5]octane-1-carboxamide (C-4-7), (1S,3s,6R)—N-phenyl-6-(quinolin-4-yl)spiro[2.5]octane-1-carboxamide (C-4-8), (1S,3s,6R)—N-phenyl-6-(quinolin-4-yl)spiro[2.5] octane-1-carboxamide (C-4-9), (1R,3r,6R)—N-phenyl-6-(quinolin-4-yl)spiro[2.5]octane-1-carboxamide (C-5-4), (1S,3s,6R)-6-(1,6-naphthyridin-4-yl)-N-phenylspiro[2.5] octane-1-carboxamide (C-6-9), (1S,3s,6R)-6-(1,6-naphthyridin-4-yl)-N-phenylspiro[2.5]octane-1-carboxamide (C-7-6), (1R,3s,6S)-6-(1,6-naphthyridin-4-yl)-N-phenyl-spiro[2.5]octane-1-carboxamide (C-7-7), (1S,3s,6R)—N-phenyl-6-(quinolin-4-yl)spiro[2.5]octane-1-carboxamide (C-8-4A), (1S,3s,6R)—N-phenyl-6-(quinolin-4-yl)spiro[2.5]octane-1-carboxamide (C-8-4B), (1S,3s,6R)—N-phenyl-6-(quinolin-4-yl)spiro[2.5]octane-1-carboxamide (C-8-4C), (1S,3s,6R)—N-phenyl-6-(quinolin-4-yl)spiro[2.5]octane-1-carboxamide (C-8-4D), (1S,3s,6R)—N-phenyl-6-(quinazolin-4-yl)spiro[2.5]octane-1-carboxamide (C-8-4E), (1S,3s,6R)-6-(1,6-naphthyridin-4-yl)-N-phenylspiro[2.5]octane-1-carboxamide (C-8-4F), N-((1S,3s,6R)-6-(quinolin-4-yl)-spiro[2.5]octan-1-yl)benzamide (C-9-3), N-((1S,3s,6R)-6-(quinolin-4-yl)-spiro[2.5]octan-1-yl)benzamide (C-9-4), N-((1R,3s,6S)-6-(quinolin-4-yl)-spiro[2.5]octan-1-yl)benzamide (C-9-5), N-((1S,3s,6R)-6-(quinolin-4-yl)spiro[2.5]octan-1-yl)benzamide (C-9-6), N-((1S,3s,6R)-6-(quinolin-4-yl)spiro[2.5]octan-1-yl)benzamide (C-9-7), N-((1S,3s,6R)-6-(quinolin-4-yl)-spiro[2.5]octan-1-yl)benzamide (C-9-8), N-((1S,3s,6R)-6-(quinolin-4-yl)-spiro[2.5]octan-1-yl)benzamide (C-9-9), (1R,3s,6S)-1-fluoro-N-phenyl-6-(quinolin-4-yl)spiro[2.5]octane-1-carboxamide (C-10-4), (1S,3s,6R)-1-methyl-N-phenyl-6-(quinolin-4-yl)spiro[2.5]octane-1-carboxamide (C-11-5), (1R,3r,6R)-1-methyl-N-phenyl-6-(quinolin-4-yl)spiro[2.5]octane-1-carboxamide (C-11-6), N-phenyl-6-(quinolin-4-yl)-6-azaspiro[2.5]-octane-1-carboxamide (C-12-5), (S)—N-phenyl-6-(quinolin-4-yl)-6-azaspiro[2.5]-octane-1-carboxamide (C-12-6), (R)—N-phenyl-6-(quinolin-4-yl)-6-azaspiro[2.5]-octane-1-carboxamide (C-12-7), N-(6-(quinolin-4-yl)-6-azaspiro[2.5]-octan-1-yl)benzamide (C-13-3), N-(7-(quinolin-4-yl)spiro[3.5]nonan-1-yl)benzamide (C-14-7), N-phenyl-7-(quinolin-4-yl)spiro[3.5]nonane-1-carboxamide (C-15-3), N-phenyl-7-(quinolin-4-yl)spiro[3.5]nonane-2-carboxamide (C-16-6), (2S,4s,7S)—N-phenyl-7-(quinolin-4-yl)spiro[3.5]nonane-2-carboxamide (C-16-7), (2R,4r,7R)—N-phenyl-7-(quinolin-4-yl)spiro[3.5]nonane-2-carboxamide (C-16-8), N-(7-(quinolin-4-yl)spiro[3.5] nonan-2-yl)benzamide (C-17-6), N-(7-(quinolin-4-yl)spiro[3.5]nonan-2-yl)benzamide (C-17-7), N-(7-(quinolin-4-yl)spiro[3.5]nonan-2-yl)benzamide (C-17-8), N-(7-(quinolin-4-yl)spiro[3.5]nonan-2-yl)isonicotinamide (C-17-9), N-(7-(quinolin-4-yl)-7-azaspiro[3.5]nonan-2-yl)benzamide (C-18-5), N-phenyl-7-(quinolin-4-yl)-7-azaspiro[3.5]-nonane-2-carboxamide (C-19-3), (2S,4s,7S)-7-(1,6-naphthyridin-4-yl)-N-phenyl-spiro[3.5]nonane-2-carboxamide (C-20-8), (2R,4r,7R)-7-(1,6-naphthyridin-4-yl)-N-phenyl-spiro[3.5]nonane-2-carboxamide (C-20-9), N-((2S,4s,7S)-7-(1,6-naphthyridin-4-yl)-spiro[3.5]nonan-2-yl)benzamide (C-21-4), N-((2R,4r,7R)-7-(1,6-naphthyridin-4-yl)-spiro[3.5]nonan-2-yl)benzamide (C-21-5), N-(7-(1,6-naphthyridin-4-yl)-7-azaspiro[3.5]-nonan-2-yl)benzamide (C-22-5), N-(1-((1s,4s)-4-(quinolin-4-yl)cyclohexyl)cyclopropyl)benzamide (C-23-5A), N-(1-((1r,4r)-4-(quinolin-4-yl)cyclohexyl)cyclopropyl)benzamide (C-23-5B), N-phenyl-1-((1s,4s)-4-(quinolin-4-yl)cyclohexyl)-cyclopropane-1-carboxamide (C-24-5A), N-phenyl-1-((1r,4r)-4-(quinolin-4-yl)cyclohexyl)-cyclopropane-1-carboxamide (C-24-5B), N-phenyl-1-(1-(quinolin-4-yl)piperidin-4-yl)-cyclopropane- 1-carboxamide (C-26-8), N-(1-(1-(quinolin-4-yl)piperidin-4-yl)cyclopropyl)benzamide (C-27-3), 1-((1s,4s)-4-(1,6-naphthyridin-4-yl)cyclohexyl)-N-phenylcyclopropane-1-carboxamide (C-28-5), 1-((1r,4r)-4-(1,6-naphthyridin-4-yl)cyclohexyl)-N-phenylcyclopropane-1-carboxamide (C-29-6), or a salt of any of these compounds.

19. The compound of claim 12, wherein the compound is a cis-isomer.

20. The compound of claim 12, wherein the compound is a trans-isomer.

21. The compound of claim 1, wherein the compound is deuterated.

22. The compound of claim 18, wherein the compound is:

1-9
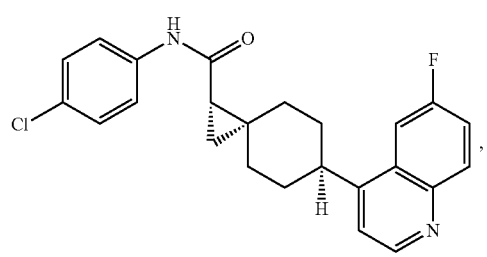

1-10
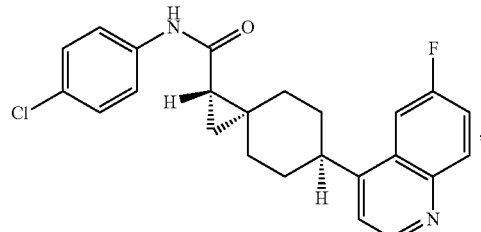

1-11
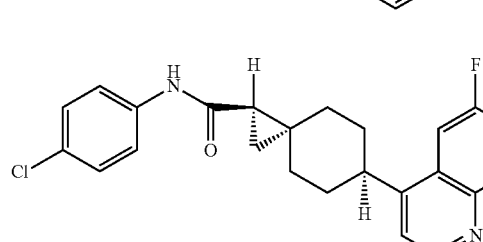

1-12
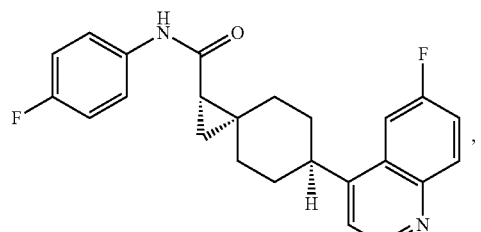

1-13
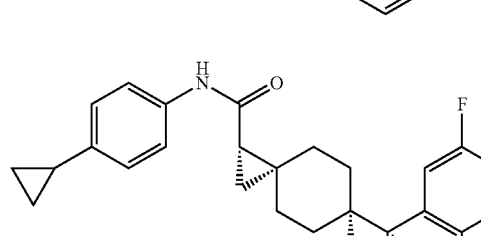

1-14
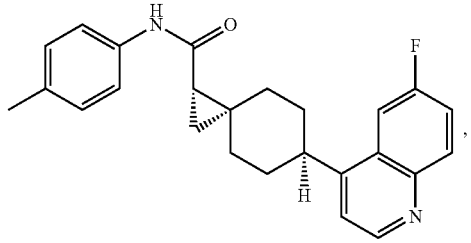

1-15
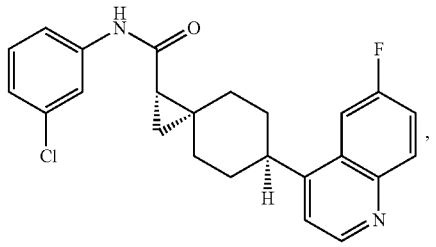

1-16
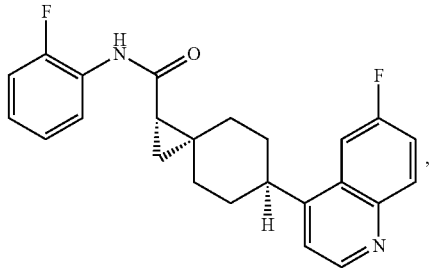

1-17
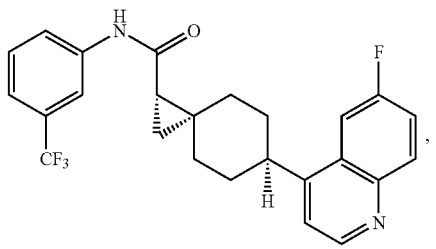

1-18
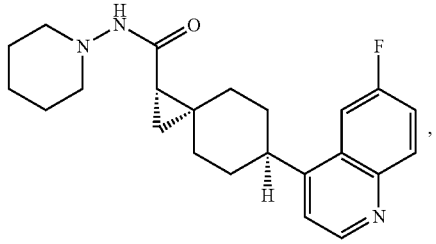

1-19
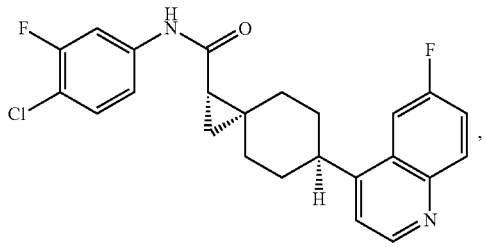

1-20
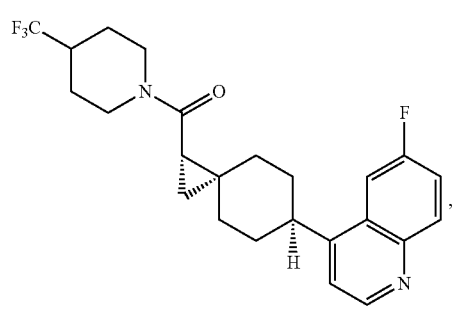
1-21
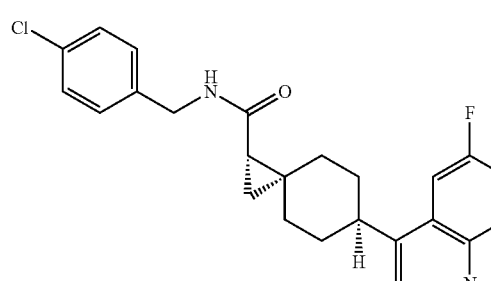
1-22
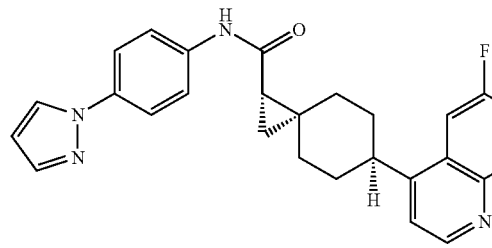
1-23
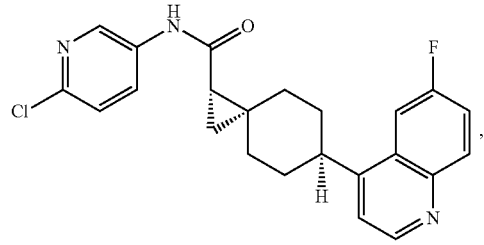
2-1
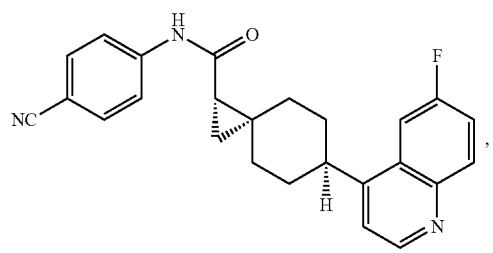
2-2
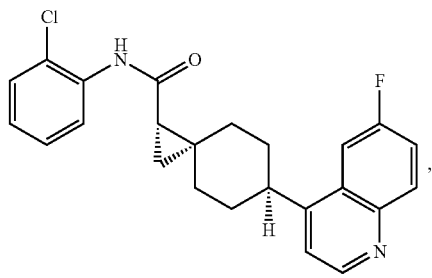
2-3
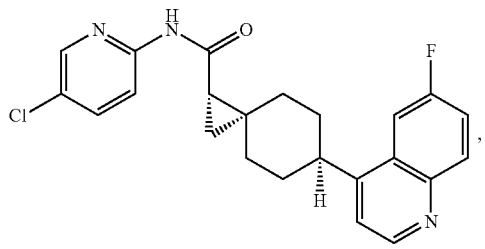
2-4
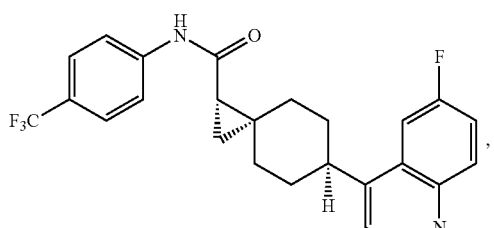
2-5
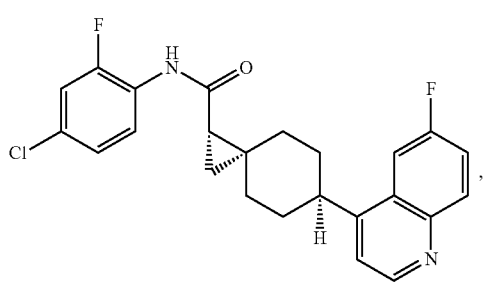
2-6
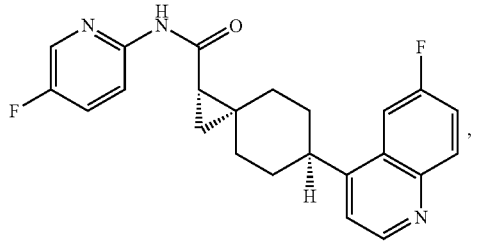
3-2
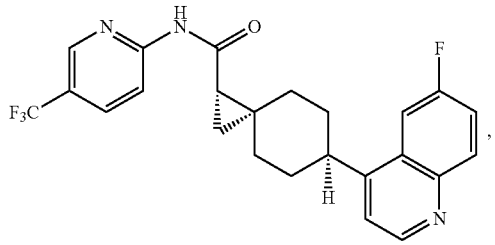

3-3
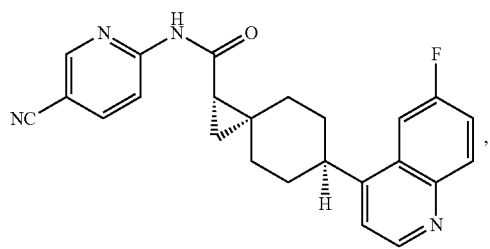
4-4
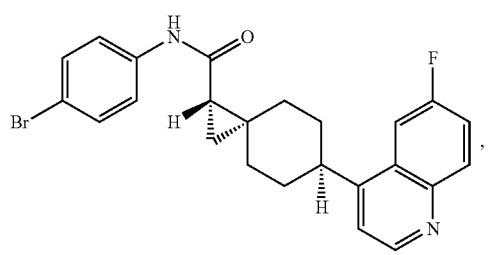
4-5
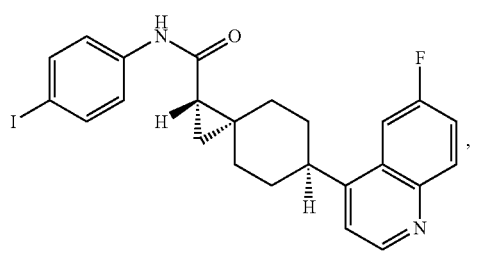
4-6
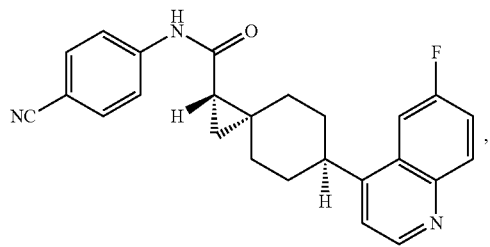
4-7
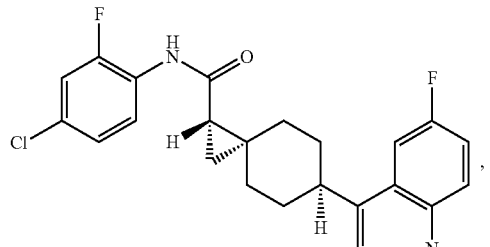
4-8
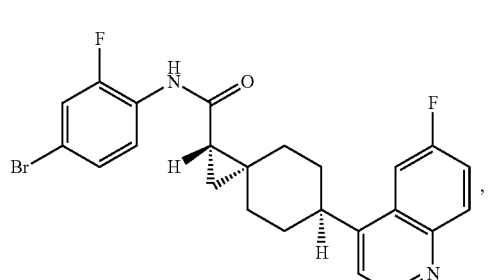
4-9
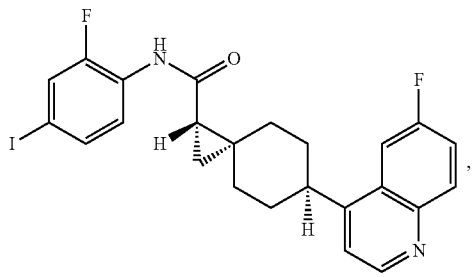
5-4
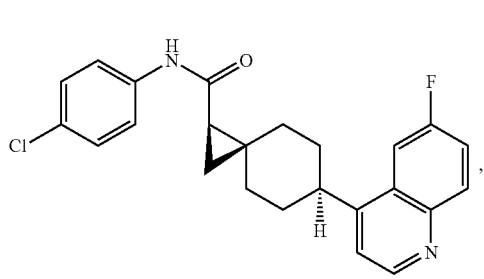
6-9
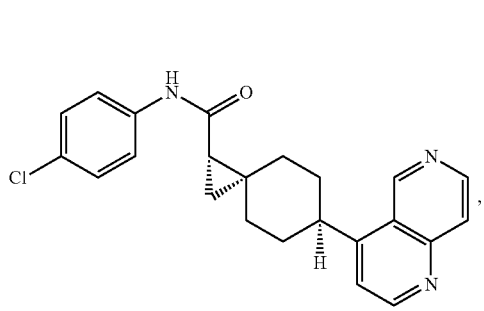
7-6
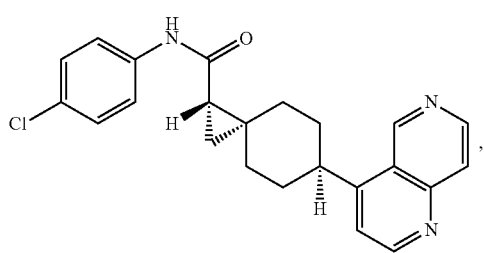
7-7
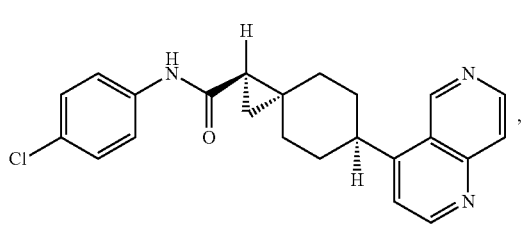
8-4A
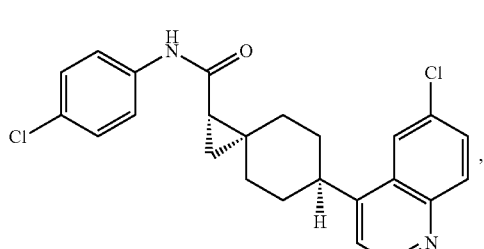

8-4B
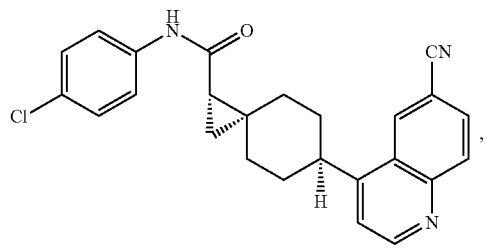
8-4C
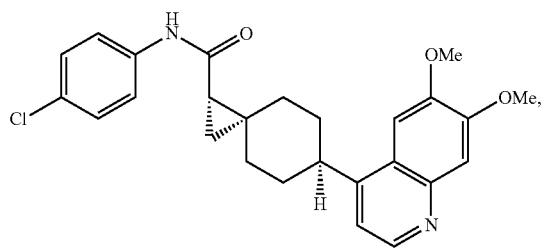
8-4D
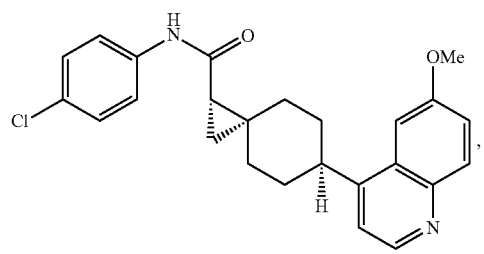
8-4E
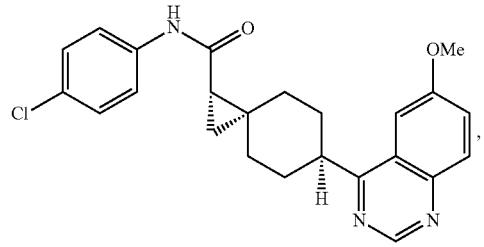
8-4F
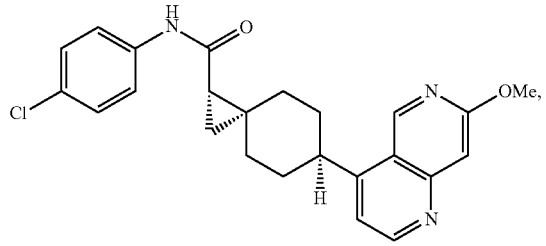
9-3
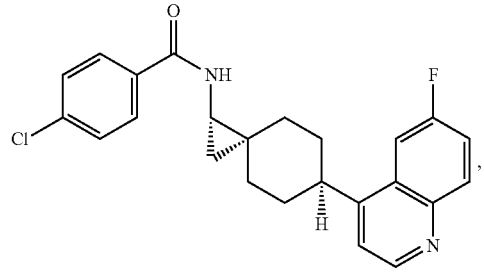
9-4
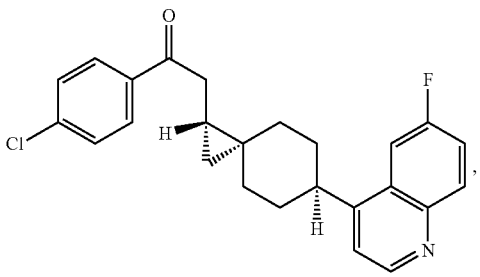
9-5
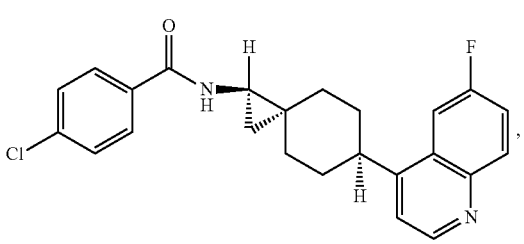
9-6
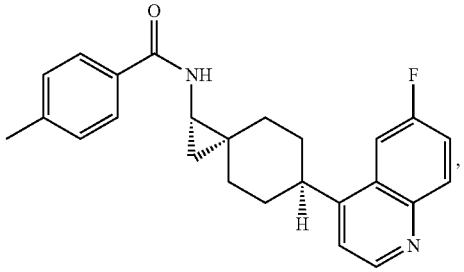
9-7
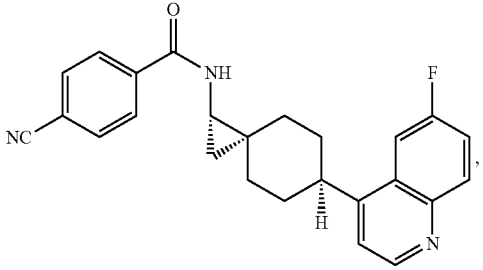
9-8
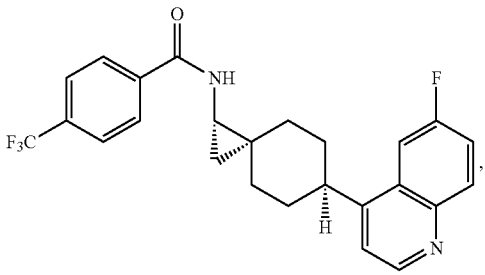

9-9
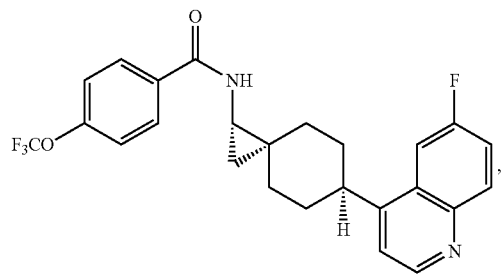
10-4
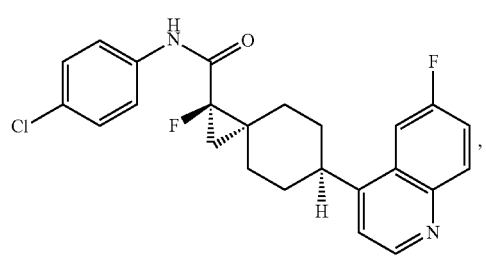
11-5
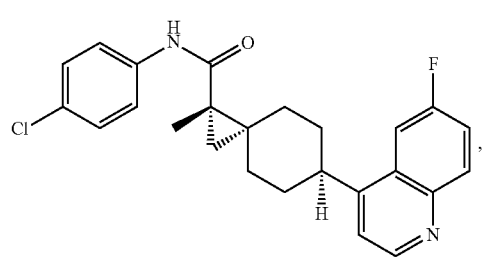
11-6
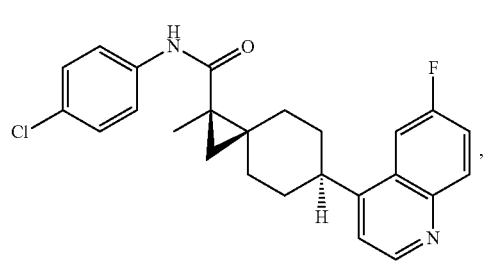
12-5
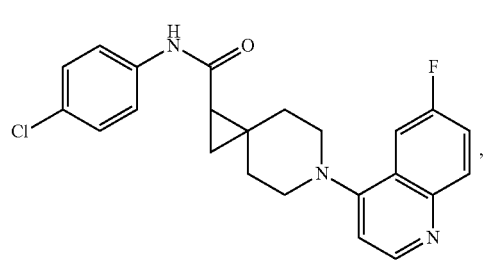
12-6
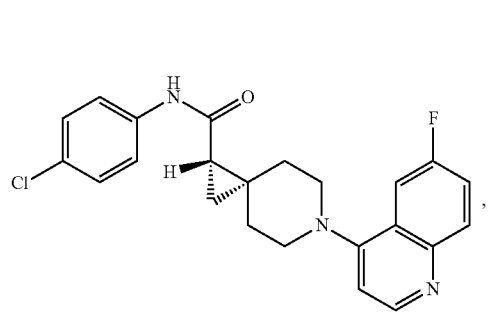
12-7
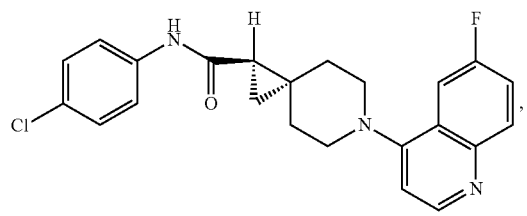
13-3
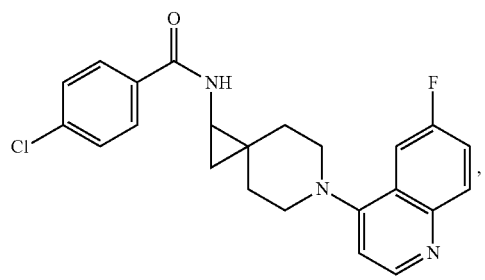
14-7
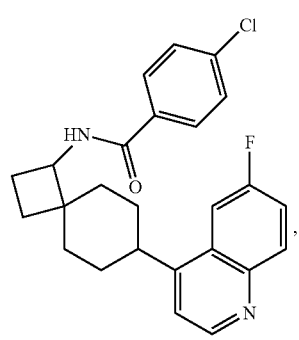
15-3
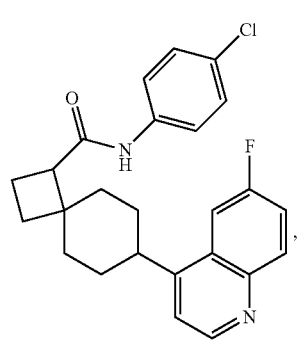
16-6
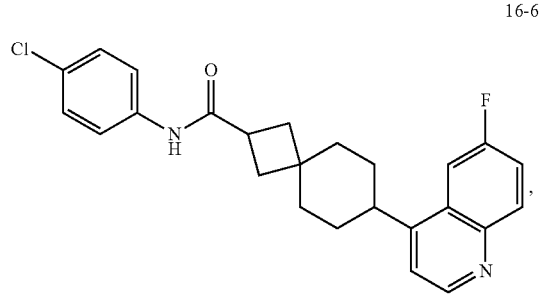

16-7
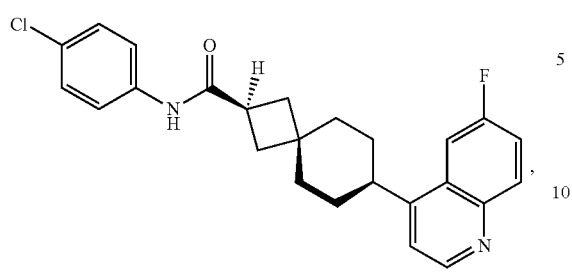
16-8
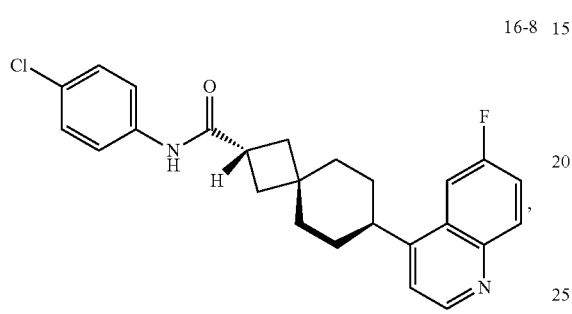
17-6
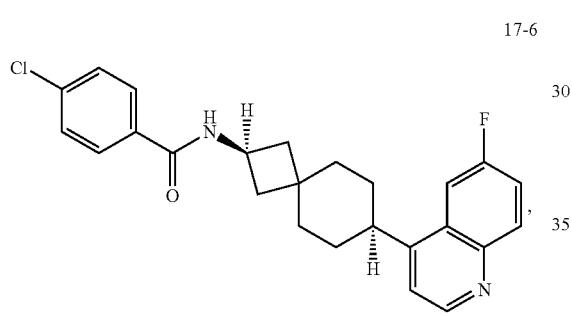
17-7
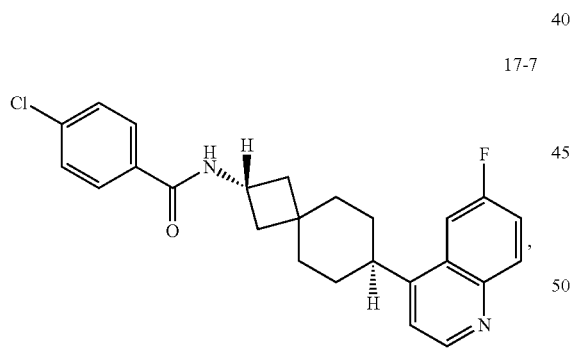
17-8
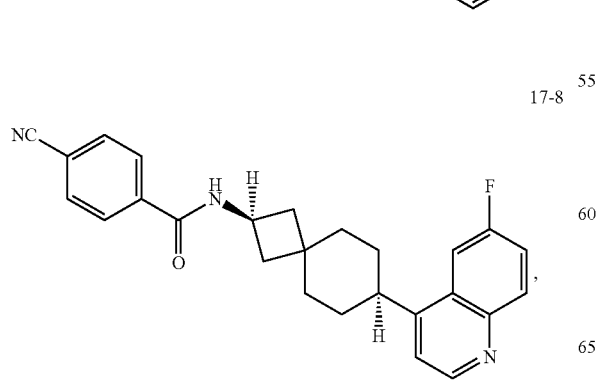
17-9
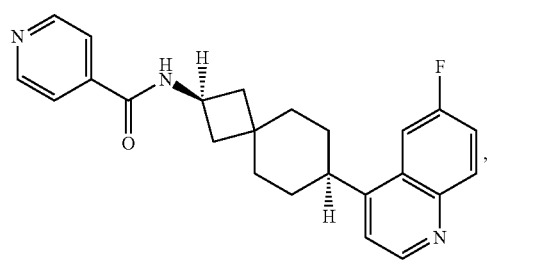
18-5
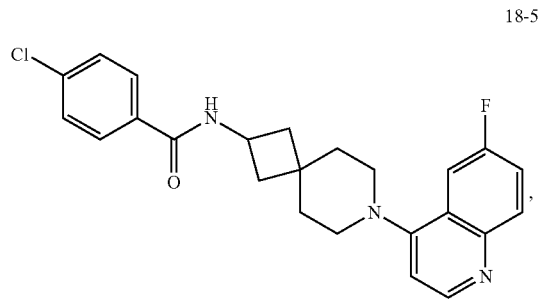
19-3
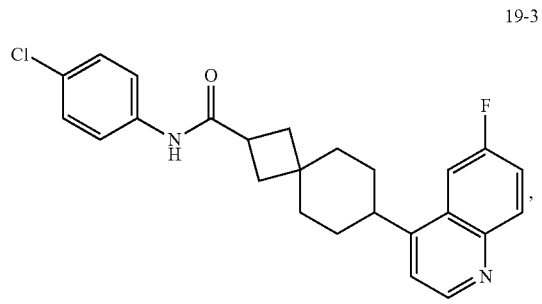
20-8
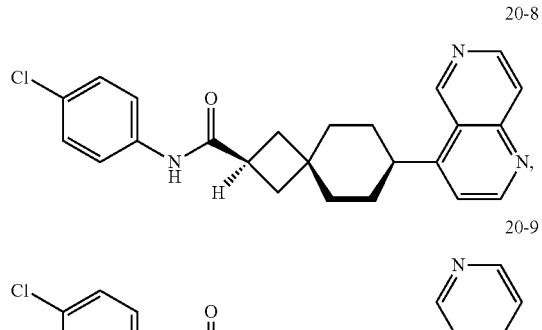
20-9
21-4
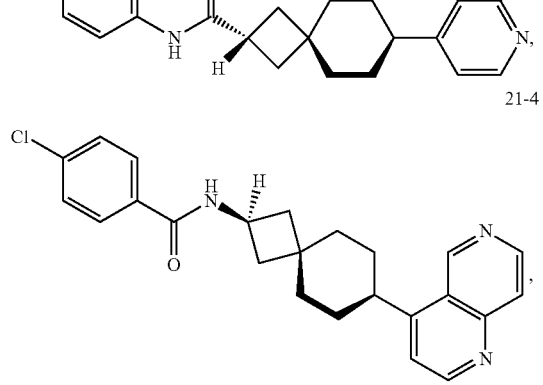

21-5
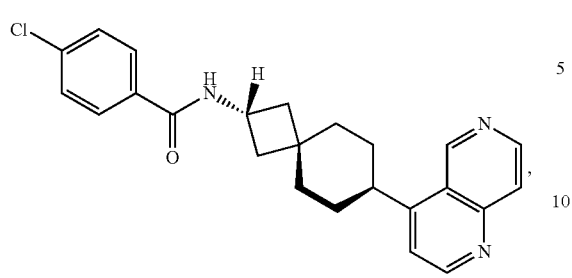
22-5
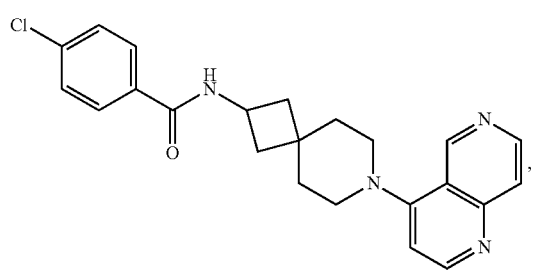
23-5A
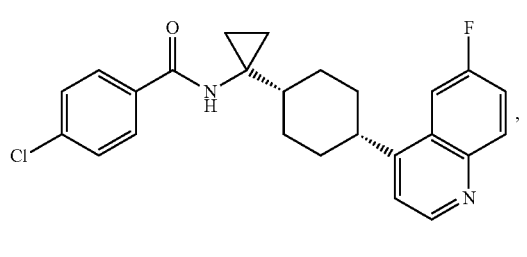
23-5B
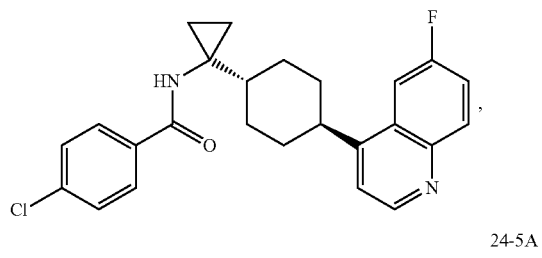
24-5A
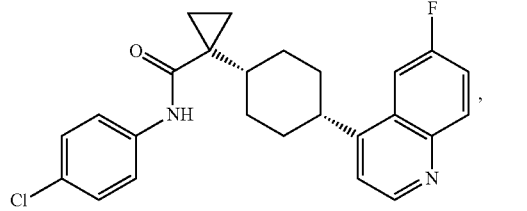
24-5B
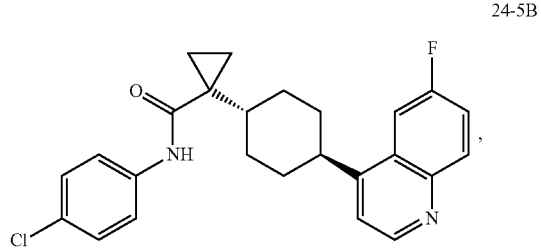
26-8
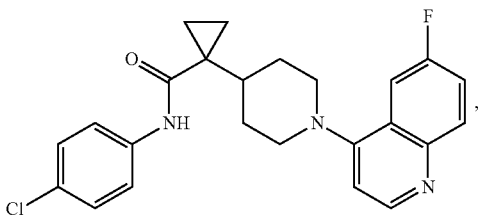
27-3
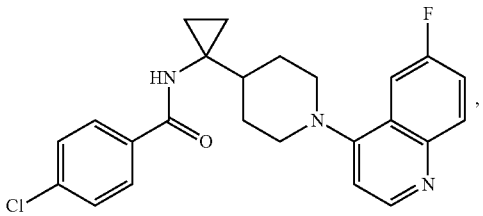
28-6
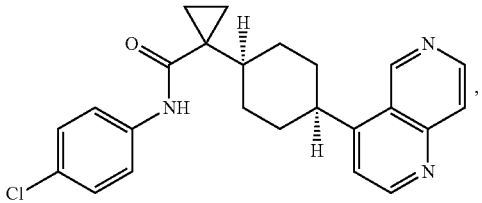
29-6
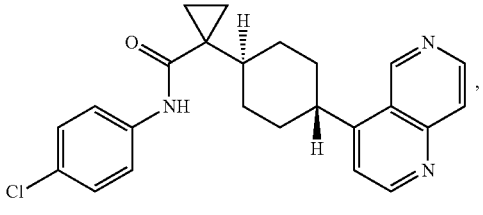
or a pharmaceutically acceptable salt of any of these compounds.
23. The compound of claim 22, or a pharmaceutically acceptable salt thereof, wherein the compound is:
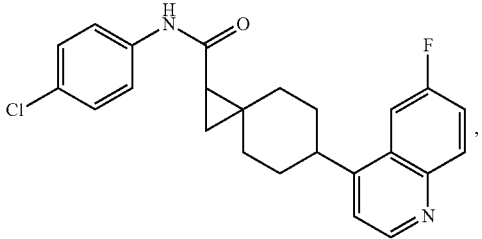
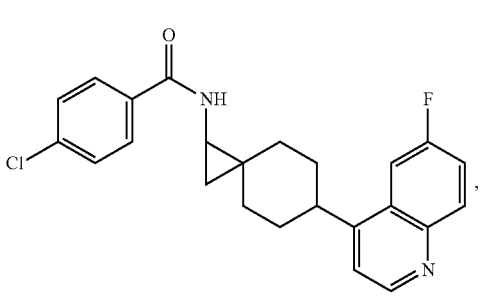

119
-continued
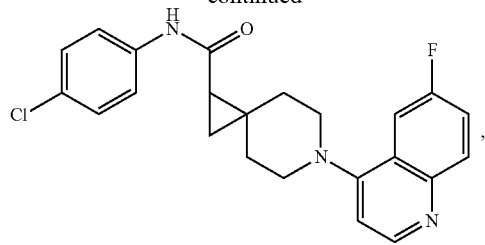
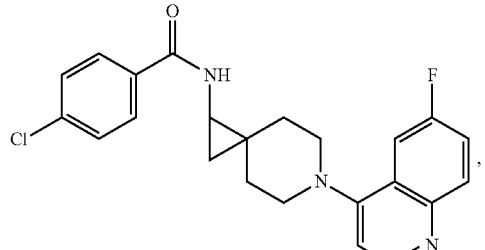
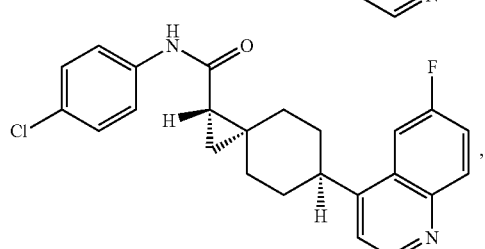
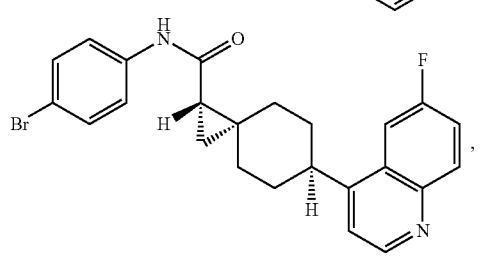
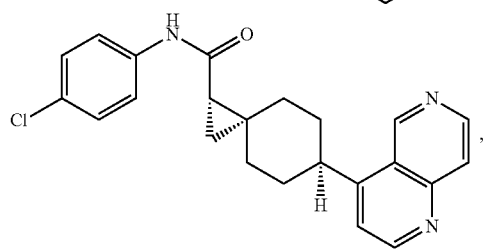
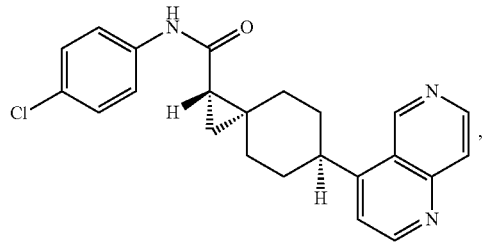
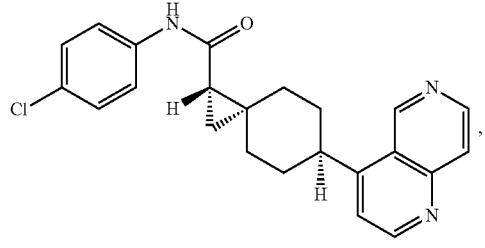
120
-continued
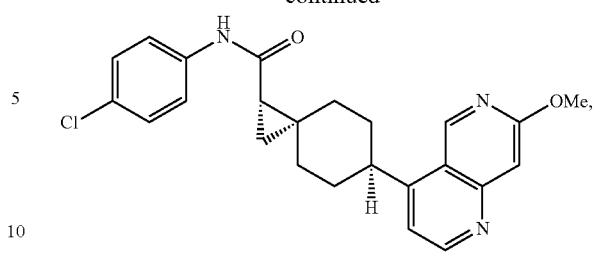
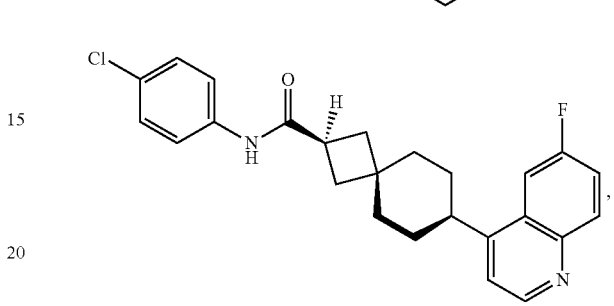
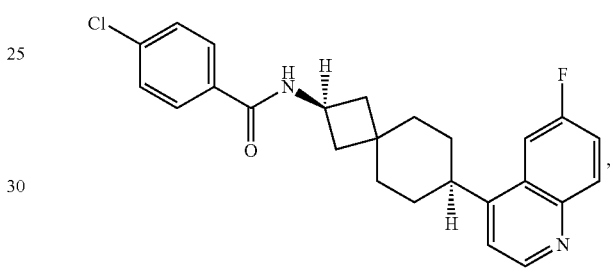
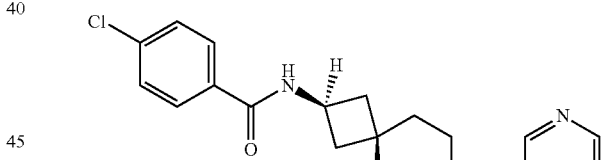
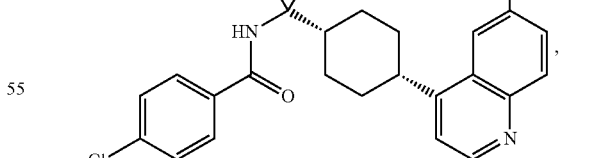
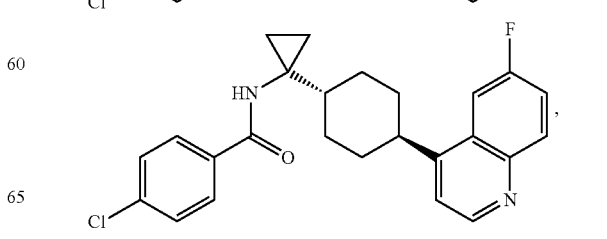

-continued
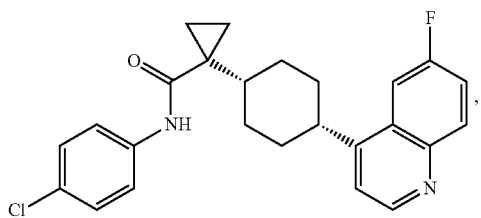
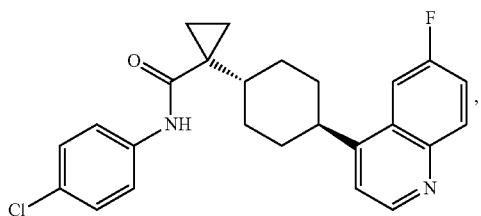
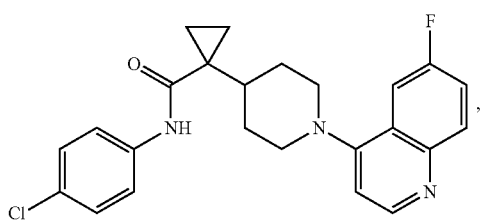
-continued
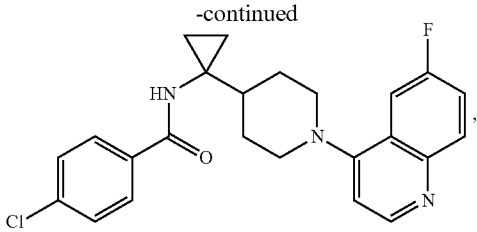
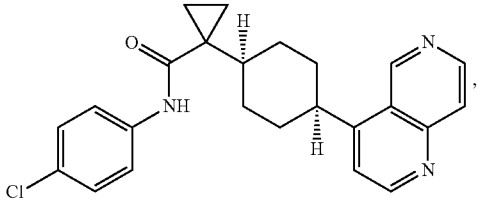
, or
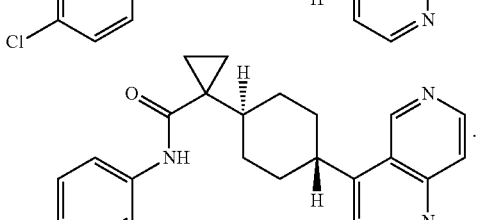
.
24. A method of treating cancer comprising administering a compound of claim 1 to a patient in need thereof.
25. A pharmaceutical composition comprising a therapeutically effective amount of a compound of claim 1 in combination with at least one pharmaceutically acceptable carrier.
* * * * *